(12) United States Patent
Hong et al.

(10) Patent No.: US 9,316,654 B2
(45) Date of Patent: Apr. 19, 2016

(54) TAZ/WWTR1 FOR DIAGNOSIS AND TREATMENT OF CANCER

(71) Applicant: **AGENCY FOR SCIENCE, TECHNOLOGY AND RESEARCH (A*STAR)**, Singapore (SG)

(72) Inventors: Wanjin Hong, Singapore (SG); Siew Wee Chan, Singapore (SG)

(73) Assignee: **Agency For Science, Technology and Research (A*STAR)**, Singapore (SG)

(*) Notice: Subject to any disclaimer, the term of this patent is extended or adjusted under 35 U.S.C. 154(b) by 0 days.

(21) Appl. No.: 13/919,129

(22) Filed: Jun. 17, 2013

(65) Prior Publication Data

US 2013/0338028 A1 Dec. 19, 2013

Related U.S. Application Data

(62) Division of application No. 12/680,982, filed as application No. PCT/SG2008/000387 on Oct. 6, 2008, now Pat. No. 8,486,903.

(60) Provisional application No. 60/977,509, filed on Oct. 4, 2007, provisional application No. 61/124,119, filed on Apr. 14, 2008.

(51) Int. Cl.

| | |
|---|---|
| *G01N 33/574* | (2006.01) |
| *A61K 39/395* | (2006.01) |
| *G01N 33/68* | (2006.01) |
| *C07K 16/18* | (2006.01) |
| *C12N 5/09* | (2010.01) |
| *C12N 15/113* | (2010.01) |

(52) U.S. Cl.
CPC ............ *G01N 33/6893* (2013.01); *C07K 16/18* (2013.01); *C12N 5/0693* (2013.01); *C12N 15/113* (2013.01); *G01N 33/57415* (2013.01); *C12N 2310/111* (2013.01); *C12N 2310/14* (2013.01); *C12N 2503/02* (2013.01)

(58) Field of Classification Search
None
See application file for complete search history.

(56) References Cited

U.S. PATENT DOCUMENTS

| | | | |
|---|---|---|---|
| 2003/0157481 A1 | 8/2003 | Benjamin et al. | |
| 2006/0056948 A1 | 3/2006 | Hossain et al. | |
| 2007/0099209 A1 | 5/2007 | Clarke et al. | |
| 2007/0269432 A1* | 11/2007 | Nakamura et al. | ......... 424/138.1 |

FOREIGN PATENT DOCUMENTS

| | | |
|---|---|---|
| AU | 2005248147 | 12/2005 |
| WO | 2006/008526 A2 | 1/2006 |

OTHER PUBLICATIONS

Nagaraja et al (Oncogene, 2006, 25:2328-2338, published online Nov. 28, 2005).*
Turashvili et al (BMC Cancer, Mar. 27, 2007, 7:55, internet pp. 1-20).*
ADAPT website, Paterson Institute of Cancer Research, probesets for "WWTR1", printed Mar. 14, 2014.*
ADAPT website, Paterson Institute of Cancer Research, probesets for "IGFBP3", printed Mar. 15, 2014.*
NCBI *Homo sapiens* transcriptional co-activator with PDZ-binding motif (TAZ)"NM_015472" Version 4, printed Mar. 14, 2014.*
NCBI *Homo sapiens* transcriptional co-activator with PDZ-binding motif (TAZ)"NM_015472" Version 1, printed Mar. 15, 2014.*
HUGO Gene Nomenclature Committee for TAZ, printed Mar. 15, 2014.*
HUGO Gene Nomenclature Committee for WWTR1, printed Mar. 15, 2014.*
2014 Procedure for Subject Matter Eligibility Analysis of Claims Reciting or Involving Laws of Nature/Natural Principles, Natural Phenomena, and/or Natural Products, Mar. 4, 2014.*
Tordai et al (Cancer Research, May 1, 2007, 67: abstract 1978).*
Hong et al., Science, 309:1074-1078 (2005). "TAZ, a transcriptional modulator of mesenchymal stem cell differentiation."
Kanai et al., The EMBO Journal, 19:6778-6791 (2000). "TAZ a novel transcriptional co-activator regulated by interactions with 14-3-3 and PDZ domain proteins."
Devi, Cancer Gene Therapy, 13:819-829 (2006).
Sibley et al., Molecular Therapy, 18:466-476 (2010).
Chan et al., "YAP, TAZ, and Yorkie: a conserved family of signal-responsive transcriptional coregulators in animal development and human disease", Biochemistry and Cell Biology. Biochimie et Biologie Cellulaire, NCR Research, 87(1):77-91 (2009).
Chan et al., "The Hippo pathway in biological control and cancer development", Journal of Cellular Physiology 226(4):928-939 (2011).
Hornung et al., "Sequence-specific potent induction of IFN-alpha by short interfering RNA in plasmacytoid dendritic cells through TLR7", Nat Med 11(3):263-270 (2005).
Navarro et al., "Tamoxifen aziridine binding to cytosolic proteins from human breast specimens is negatively associated with estrogen receptors, progesterone receptors, pS2, and cathepsin-D", Breast and Cancer Research and Treatment, 50(2):155-166 (1998).
Parry et al., "Cycloheximide treatment modifies the pattern of "metastasis" following intravenous injection of Ehrlich ascites tumour cells", Gan 72(3):464-467 (1981).

(Continued)

*Primary Examiner* — Laura B Goddard
(74) *Attorney, Agent, or Firm* — Nixon Peabody LLP; Mark J. FitzGerald

(57) ABSTRACT

We provide an anti-TAZ agent for the treatment, prophylaxis or alleviation of cancer. We further provide a kit for detecting breast cancer in an individual or susceptibility of the individual to breast cancer comprising means for detection of TAZ expression in the individual or a sample taken from him or her as well as a method of detecting a cancer cell, the method comprising detecting modulation of expression, amount or activity of TAZ in the cell.

1 Claim, 36 Drawing Sheets

(56) References Cited

OTHER PUBLICATIONS

Ponting et al., "ZZ and TAZ: new putative zinc fingers in dystrophin and other proteins", Trends in Biochemical Sciences 21(1):11-13 (1996).

Tordai et al. "Screening for expression of novel marker proteins for triple negative breast cancer in breast cancer cell lines", Proceedings of the Annual Meeting of the American Association for Cancer Research, 48:471 (2007).

Wang et al., "YAP, TAZ, and Yorkie: a conserved family of signal-responsive transcriptional coregulators in animal development and human disease", Biochemistry and Cell Biology. Biochimie Et Biologie Cellulaire, NCR Research Press, 87(1):77-91 (2009).

* cited by examiner

MCF7-KD-715          MCF7-KD-652

| Hs578T-KD-715 | Hs578T-KD-652 | |
|---|---|---|
|  |  | 0h |
|  |  | 6h |
|  |  | 12h |

MCF7-KD-715

MCF7-KD-652

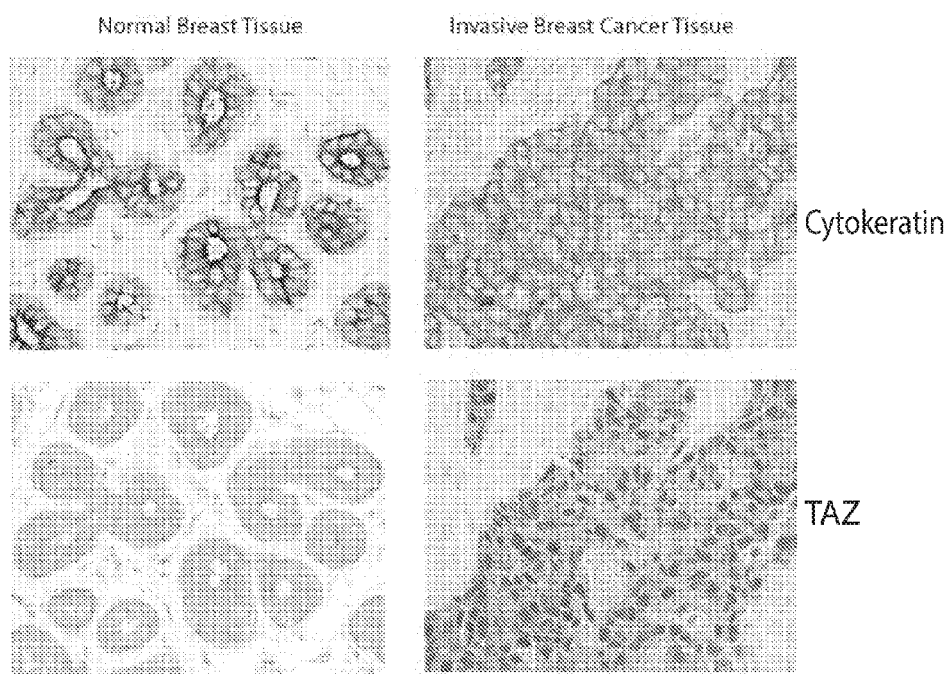

MCF7-KD-715 +Control  MCF7-KD-715 +Flag-mTAZ

MCF7-KD-652 +Control MCF7-KD-652 +Flag-mTAZ

TAZ-S89A

TEAD-binding mutant (M9)

TEAD-binding mutant (M9)

TAZ-S89A

SEQUENCE LISTING

<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
gatgaatccg gcctcggcgc c                                          21

<210> SEQ ID NO 2

-continued

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agaggtactt cctcaatca                                                19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aggtacttcc tcaatcaca                                                19

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5

<210> SEQ ID NO 5
<211> LENGTH: 70
<212> TYPE: PRT
<213> ORGANISM: Homo sapiens

<400> SEQUENCE: 5

Asn Gln Pro Leu Asn His Met Asn Leu His Pro Ala Val Ser Ser Thr
1               5                   10                  15

Pro Val Pro Gln Arg Ser Met Ala Val Ser Gln Pro Asn Leu Val Met
            20                  25                  30

Asn His Gln His Gln Gln Gln Met Ala Pro Ser Thr Leu Ser Gln Gln
        35                  40                  45

Asn His Pro Thr Gln Asn Pro Pro Ala Gly Leu Met Ser Met Pro Asn
    50                  55                  60

Ala Leu Thr Thr Gln Gln
65                  70

<210> SEQ ID NO 6
<211> LENGTH: 54
<212> TYPE: PRT
<213> ORGANISM: Homo sapiens

<400> SEQUENCE: 6

Leu Glu Ala Leu Phe Asn Ser Val Met Asn Pro Lys Pro Ser Ser Trp
1               5                   10                  15

Arg Lys Lys Ile Leu Pro Glu Ser Phe Phe Lys Glu Pro Asp Ser Gly
            20                  25                  30

Ser His Ser Arg Gln Ser Ser Thr Asp Ser Ser Gly Gly His Pro Gly
        35                  40                  45

Pro Arg Leu Ala Gly Gly
```

```
<210> SEQ ID NO 7
<211> LENGTH: 6
<212> TYPE: PRT
<213> ORGANISM: Unknown
<220> FEATURE:
<223> OTHER INFORMATION: Description of Unknown: Phosphoserine-binding
      motif

<400> SEQUENCE: 7

Arg Ser His Ser Ser Pro
1               5

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cagcctctga atcatatga                                                19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aacaaacgtt gacttagga                                                19
```

TAZ/WWTR1 FOR DIAGNOSIS AND TREATMENT OF CANCER

CROSS-REFERENCE TO RELATED APPLICATIONS

This application is a divisional of U.S. patent application Ser. No. 12/680,982 filed on Mar. 31, 2010, now U.S. Pat. No. 8,486,903, which issued on Jul. 16, 2013, which is a 35 U.S.C. §371 National Phase Entry Application of International Application No. PCT/SG2008/000387 filed on Oct. 6, 2008, which designated the U.S., and which claims benefit under 35 U.S.C. §119(e) of U.S. Provisional Application No. 60/977,509 filed on Oct. 4, 2007, and U.S. Provisional Application No. 61/124,119 filed on Apr. 14, 2008, the contents of each of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jun. 17, 2013, is named 049595-067711_SequenceListing.txt and is 3,131 bytes in size.

FIELD

The present invention relates to the fields of medicine, cell biology, molecular biology and genetics. This invention relates to the field of medicine. In particular, it relates to treatment and diagnosis of diseases, in particular breast cancer, as well as compositions for such use.

BACKGROUND

TAZ, also known as WWTR1, is a 14-3-3 binding protein with a PDZ binding motif. TAZ/WWTR1 is known to modulate mesenchymal stem cell differentiation TAZ/WWTR1 was first cloned by Kanai et al. (2000). Kanai showed that TAZ RNA is most highly expressed in human kidney, followed by heart, placenta and lung. Expression was detected in all tissues tested except thymus and peripheral blood leukocytes. Northern blot analysis of mouse tissues showed transcripts expressed at highest levels in kidney, lung, liver, and heart and also in testis. Western blot analysis revealed expression of TAZ in several epithelial and fibroblast cell lines, but not in Jurkat T cells.

Mesenchymal stem cells are a pluripotent cell type that can differentiate into several distinct lineages. Two key transcription factors, RUNX2 (OMIM reference 600211) and peroxisome proliferator-activated receptor-gamma (PPARG; OMIM reference 601487), drive mesenchymal stem cells to differentiate into either osteoblasts or adipocytes, respectively. Hong et al. (2005) found that TAZ/WWTR1 coactivates RUNX2-dependent gene transcription while repressing PPARG-dependent gene transcription.

By modulating Taz expression in model cell lines, mouse embryonic fibroblasts, and primary mesenchymal stem cells in culture and in zebrafish in vivo, Hong et al. (2005) observed alterations in osteogenic versus adipogenic potential. Hong et al. (2005) concluded that TAZ functions as a molecular rheostat that modulates mesenchymal stem cell differentiation.

Murakami (2005) show that TAZ acts as a potent TBX5 coactivator that physically associates with TBX5 and histone acetyltransferase (HAT) proteins and mediates TBX5-dependent gene activation. Murakami (2005) suggest that TAZ plays important roles in the control of TBX5-dependent genes during cardiac and limb development.

Hossain (2007) show that WWTR1 is critical for the integrity of renal cilia and its absence in mice leads to the development of renal cysts. Hossain (2007) concludes that Wwtr1 may represent a candidate gene for polycystic kidney disease in humans.

In the Western world and the developed countries of Asia, breast carcinoma is the second leading cause of cancer-related death in women (Polyak, 2001). Breast cancer tops the cancer list for women in Singapore, with 700-800 new cases being diagnosed each year (Singapore Cancer Registry Report, 2000). In the USA, 180,000 women are diagnosed annually with new cases of breast cancer (Polyak, 2001). Despite better diagnosis and routine screening around a quarter of the cases will die from their disease.

Accordingly, there is a need for improved breast cancer detection and therapy.

SUMMARY

According to a 1st aspect of the present invention, we provide an anti-TAZ agent for the treatment, prophylaxis or alleviation of cancer.

The anti-TAZ agent may be capable of down-regulating any combination of the expression, amount or activity of a TAZ sequence shown as GenBank accession number NP_056287, or a sequence which has at least 90% sequence identity to that sequence.

The cancer may comprise breast cancer. The cancer may comprise an invasive or metastatic cancer such as Invasive Ductal Carcinoma (IDC). The anti-TAZ agent may down-regulate TAZ by RNA interference, such as by comprising a Small Interfering RNA (siRNA) or Short Hairpin RNA (shRNA).

The anti-TAZ agent may comprise shRNA 1 (sense oligonucleotide sequence 5'-GATGAATCCGGCCTCGGCGCC-3' (SEQ ID NO: 1)), shRNA 650 (sense oligonucleotide sequence 5'-AGAGGTACTTCCTCAATCA-3' (SEQ ID NO: 2)) or shRNA 652 (sense oligonucleotide sequence 5'-AGGTACTTCCTCAATCACA-3' (SEQ ID NO: 3)).

The anti-TAZ agent may comprise an anti-TAZ antibody, for example selected from the group consisting of: rabbit anti-TAZ antibody against amino acids 160-229 of TAZ, rabbit anti-TAZ antibody (catalogue number 2149S, Cell Signaling Technology, Danvers, Mass., USA), rabbit polyclonal anti-TAZ antibody (catalogue number NB110-58359SS, Novus Biological, Littleton, Colo., USA), Mouse Monoclonal anti-TAZ [1B10] (catalogue number H00006901-M12, Novus Biological, Littleton, Colo., USA), Rabbit anti-Human TAZ Polyclonal Antibody (catalogue number LS-B94, LifeSpan Biosciences, Inc., Seattle, Wash., USA) or p-TAZ (Ser 89)-R (catalogue number sc-17610-R, Santa Cruz Biotechnology, Santa Cruz, Calif., USA).

There is provided, according to a 2$^{nd}$ aspect of the present invention, a nucleic acid comprising shRNA 650 (sense oligonucleotide sequence 5'-AGAGGTACTTCCTCAATCA-3' (SEQ ID NO: 2)), shRNA 652 (sense oligonucleotide sequence 5'-AGGTACTTCCTCAATCACA-3' (SEQ ID NO: 3)), 5'-AGAGGTACTTCCTCAATCA-3' (SEQ ID NO: 2), 5'-AGGTACTTCCTCAATCACA-3' (SEQ ID NO: 3), or a complement thereof, or a nucleic acid capable of specifically hybridising to any such sequence.

We provide, according to a 3rd aspect of the present invention, a rabbit anti-TAZ antibody against amino acids 160-229 of TAZ, optionally in combination with a polypeptide comprising a YAP sequence (GenBank Accession Number:

NP_006097) or a sequence having at least 90% sequence identity to that sequence, such as GST-YAP.

As a 4th aspect of the present invention, there is provided an MCF10A-TAZ, MCF7-KD-1, MCF7-KD-650, MCF7-KD-652 or Hs578T-KD-652 cell or cell line, for example for use as a model for cancer, such as invasive breast cancer.

We provide, according to a 5th aspect of the present invention, a kit for detecting breast cancer in an individual or susceptibility of the individual to breast cancer comprising means for detection of TAZ expression in the individual or a sample taken from him or her.

The means for detection may be selected from the group consisting of: a TAZ polynucleotide or a fragment thereof; a complementary nucleotide sequence to TAZ nucleic acid or a fragment thereof; a TAZ polypeptide or a fragment thereof, or an anti-TAZ antibody for example comprising an antibody against amino acids 160-229 of TAZ, and optionally instructions for use. The kit may further comprise an anti-TAZ agent according to the 1st aspect of the invention. The kit may further comprise a therapeutic drug for treatment, prophylaxis or alleviation of breast cancer, such as comprising Tamoxifen or Herceptin.

The present invention, in a 6th aspect, provides a method of detecting a cancer cell, the method comprising detecting modulation of expression, amount or activity of TAZ in the cell. The cancer may comprise breast cancer, such as invasive or metastatic cancer such as Invasive Ductal Carcinoma (IDC). The expression of TAZ may be compared to the expression, amount or activity of TAZ in a control cell known to be non-cancerous.

The method may comprise detecting up-regulation of TAZ expression, amount or activity in the cell. The method may comprise detecting a TAZ nucleic acid, such as by means of a probe comprising at least a portion of a nucleic acid having a sequence shown as GenBank accession number NM_015472 or a sequence having at least 90% sequence identity to such a sequence. The method may comprise detecting a TAZ polypeptide. The TAZ polypeptide may be detected by means of an anti-TAZ antibody set out above.

The method may comprise detecting expression of one or more proteins selected from the group consisting of: IGFBP3, ADAMTS1, CTGF, Cyr61, FSTL1, FN1, FBN1, FBN2AXL, ITGB2, CRIM1 and Alcam.

The method may further comprise histological grading, for example using the Elston-Ellis modified Scarff, Bloom, Richardson grading system (Nottingham Grading System (NGS)).

A method of determining the proliferative state of a cell, or determining the likelihood that a cell will become invasive or aggressive, the method comprising detecting modulation of expression, amount or activity of TAZ in the cell.

In a 7th aspect of the present invention, there is provided a method of predicting a survival rate of an individual with cancer, the method comprising detecting modulation of expression of TAZ in a cell of the individual According to an 8th aspect of the present invention, we provide a method of choosing a therapy for an individual with cancer, the method comprising detecting modulation of expression of TAZ in a cell of the individual choosing an appropriate therapy based on the aggressiveness of the cancer.

We provide, according to a 9th aspect of the invention, a method of determining the likelihood of success of a particular therapy in an individual with a cancer, the method comprising comparing the therapy with a therapy determined by a method as set out above.

There is provided, in accordance with a 10th aspect of the present invention, a method of manipulating a cancer cell, the method comprising modulating the expression, amount or activity of TAZ in the cell.

The cancer may comprise breast cancer, such as invasive or metastatic cancer such as Invasive Ductal Carcinoma (IDC). The cancer cell may become non-cancerous or the invasive or metastatic cancer cell becomes non-invasive or non-metastatic as a result of the manipulation. The method may comprise down-regulating TAZ expression, amount or activity in the cell. The method may comprise exposing the cell to an siRNA or shRNA capable of specifically binding to TAZ. The shRNA may comprise an shRNA set out above. The method may comprise exposing the cell to an anti-TAZ antibody.

As an 11th aspect of the invention, we provide a method of manipulating a cell, the method comprising the steps of: (a) detecting increased TAZ expression, amount or activity in a cell; and (b) reducing the level of TAZ in the cell.

A method of modulating the expression of TAZ, the method comprising targeting a TAZ target site selected from KD-1 (5'-GATGAATCCGGCCTCGGCGCC-3' (SEQ ID NO: 1)), KD-650 (5'-AGAGGTACTTCCTCAATCA-3' (SEQ ID NO: 2)) or KD-652 (5'-AGGTACTTCCTCAAT-CACA-3' (SEQ ID NO: 3)).

We provide, according to a 12th aspect of the invention, there is provided a method of identifying a molecule capable of binding to a TAZ polypeptide, the method comprising: (a) contacting a TAZ polypeptide with a candidate molecule and determining whether the candidate molecule binds to the TAZ polypeptide; or (b) a method of identifying a modulator of TAZ, the method comprising contacting a cell with a candidate molecule and detecting elevated or reduced expression, amount or activity of TAZ in or of the cell.

According to a 13th aspect of the present invention, we provide a method of identifying a modulator of a TAZ polypeptide, the method comprising allowing TAZ to bind to a TEAD polypeptide comprising TEAD1, TEAD2, TEAD3 or TEAD4 and detecting modulation of such binding by the presence of a candidate molecule.

There is provided, according to a 14th aspect of the present invention, a method of identifying a molecule suitable for the treatment, prophylaxis or alleviation of cancer, the method comprising determining if a candidate molecule is an agonist or antagonist of TAZ1/WWTR or a sequence having at least 90% sequence identity thereto.

We provide, according to a 15th aspect of the present invention, use of a TAZ or a sequence having at least 90% sequence identity thereto in a method of identifying a molecule suitable for the treatment, prophylaxis or alleviation of cancer. A candidate molecule may be exposed to a TAZ polypeptide or a cell expressing a TAZ polypeptide in order to determine if the candidate molecule is an agonist or antagonist thereof.

We provide, according to a $16^{th}$ aspect of the present invention, use of a TAZ polynucleotide or a sequence having at least 90% sequence identity thereto for the identification of a molecule suitable for the treatment, prophylaxis or alleviation of cancer.

We provide, according to a 17th aspect of the present invention, a method of identifying an agonist or antagonist of a TAZ or a sequence having at least 90% sequence identity thereto, the method comprising administering a candidate molecule to an animal and determining whether the animal exhibits increased or decreased expression, amount or activity of TAZ.

We provide, according to a 18th aspect of the present invention, an expression vector comprising a nucleic acid as set out above, such as a retroviral vector. We provide, according to a 19th aspect of the present invention, a host cell comprising a nucleic acid as set out above or an expression vector as set out above. We provide, according to a 20th aspect of the present invention, a non-human animal comprising a host cell as set out above.

We provide, according to a 21st aspect of the present invention, a method of treatment, prophylaxis or alleviation of a cancer in an individual, the method comprising modulating the expression, amount or activity of a TAZ in a cell of an individual. The expression, amount or activity of TAZ may be decreased in a breast cell of the individual.

We provide, according to a 22nd aspect of the present invention, a method of diagnosis of a cancer or susceptibility to cancer in an individual, the method comprising detecting modulation of expression, amount or activity of TAZ in a cell of the individual.

We provide, according to a 23rd aspect of the present invention, a method of prognosis of an individual with cancer, the method comprising detecting modulation of expression, amount or activity of TAZ in a cell of the individual.

We provide, according to a 24th aspect of the present invention, a method of determining whether a tumour in an individual is, or is likely to be, an invasive or metastatic tumour, the method comprising detecting modulation of expression, amount or activity of TAZ in a tumour cell of the individual.

We provide, according to a 25th aspect of the present invention, a method of treatment, prophylaxis or alleviation of cancer in an individual, the method comprising detecting modulation of expression, amount or activity of TAZ in a cell of the individual and administering an appropriate therapy to the individual based on the aggressiveness of the tumour. The cancer may comprise breast cancer, such as invasive or metastatic cancer such as Invasive Ductal Carcinoma (IDC). The diagnosis, prognosis or choice of therapy may be further determined by assessing the size of the tumour, or the lymph node stage, or both, optionally together or in combination with other risk factors. The diagnosis, prognosis or choice of therapy may be further determined by assessing the oestrogen receptor (ER) status of the tumour.

We provide, according to a 26th aspect of the present invention, TAZ for use in a method of treatment, prophylaxis or alleviation of a cancer, for example breast cancer, in an individual.

We provide, according to a 27th aspect of the present invention, a molecule, agonist or antagonist of a TAZ polypeptide identified by a method or use as set out above.

We provide, according to a 28$^{th}$ aspect of the present invention, molecule capable of modulating, such as down-regulating, the expression of a TAZ for use in the treatment, prophylaxis or alleviation of cancer.

BRIEF DESCRIPTION OF THE FIGURES

FIG. 1A. Lysates derived from 11 breast cancer cell lines are analyzed by western blot using anti-TAZ antibodies which also reacted well with YAP (upper panels) or anti-YAP antibodies (lower panels). The levels of actin as detected by anti-actin antibodies are used as loading controls.

FIG. 1B. The expression levels of TAZ and YAP are quantified in three independent experiments and the averages are presented as arbitrary units relative to actin.

FIG. 2A. the levels of TAZ in MCF10A cells transduced with retrovirus expressing EGFP (lane 1), TAZ (lane 2) or Flag-TAZ (lane 3) are assessed by western blot. The levels of TAZ in Hs578T (lane 4) and BT-549 (lane 5) cells are assessed as comparisons.

FIG. 2B. wound-healing migration assay for MCF10A cells expressing EGFP (left panels) and MCF10A cells expressing TAZ (right panels). The healing of wounds by migrated cells at time 0, 14 hr and 24 hr is imaged. MCF10A cells expressing TAZ have more motile and spindle-shaped fibroblast-like appearance and migrate faster than MCF10A cells expressing EGFP.

FIG. 2C. The migration (top panel) and invasion (bottom panel) of MCF10A cells expressing EGFP and TAZ are assessed by transwell assays. Columns, mean of three independent experiments; bars, SEM.

FIG. 3A. The expression levels of TAZ in MCF7 (top panel) and Hs578T (bottom panel) cells transduced with the vector (lane1) and various shRNAs (lane 2-6) targeting different sites of TAZ mRNA are assessed by western blot. shRNA-652 is most potent in suppressing TAZ expression in both MCF7 and Hs578T cells.

FIG. 3B. TAZ knockdown in MCF7 cells results in clusters of more densely-packed and compact sheets of cells. When plated at low to medium densities, both MCF7-KD-715 cells and MCF7-KD-652 cells grew as clusters of cells. However, the cell density of the clusters is obviously enhanced in the MCF7-KD-652 cells (panel b) as compared to MCF7-KD-715 cells (panel a). Scanning electron microscopy revealed that the space between cells is reduced in MCF7-KD-652 cells (panel d) as compared to MCF7-KD-715 cells (panel c). This resulted in the appearance of more tightly aligned/packed and compact epithelia when TAZ expression is knocked-down.

FIG. 3C. TAZ knockdown in Hs578T cells suppresses cell migration. Wound-healing migration assay for Hs578T-KD-715 (left panels) and Hs578T-KD-652 (right panels) cells is performed. The healing of wounds by migrated cells at time 0, 6 hr and 12 hr is imaged. Hs578T-KD-652 cells with TAZ knockdown have much reduced motility as compared to Hs578T-KD-715 cells which have similar migration as parental and vector-transduced Hs578T cells. FIG. 3D, the migration (top panel) and invasion (bottom panel) of Hs578T-KD-715 and Hs578T-KD-652 cells are assessed by transwell assays. Columns, mean of three independent experiments; bars, SEM.

FIG. 4A. Soft-agar growth of MCF7-KD-715 (upper panel) and MCF7-KD-652 (lower panel) cells is assessed and photographed.

FIG. 4B. The appearance of live colonies in soft-agar of MCF7-KD-715 (top panel) and MCF7-KD-652 (bottom panel) cells is photographed at higher amplification.

FIG. 4C. Tumor formation of MCF7-KD-715 (right side) and MCF7-KD-652 (left side) cells in the thigh (top panel) or the fat pad (bottom panel) of nude mice are assessed and photographed.

FIG. 5A and FIG. 5B. TAZ is overexpressed in invasive (infiltrating) ductal carcinomas (IDCs).

FIG. 5A. Characterization of rabbit anti-TAZ antibodies. Lysate derived from the indicated cells are analyzed by western blot using affinity-purified rabbit antibodies raised against fragment (amino acids 160-229) of TAZ in the absence (bottom panel) or the presence of 100× of recombinant YAP fragment (amino acids 206-262) corresponding to the TAZ antigen region. Although the antibodies cross-reacted with YAP (top panel), they recognized specifically TAZ in the presence of excess amount of recombinant YAP fragment.

FIG. 5B. TAZ is overexpressed in invasive ductal carcinomas (IDC). Normal breast tissues (left panels) or breast cancer tissues (IDC) (right panels) are either stained with TAZ antibody (preincubated with 100 folds excess of recombinant YAP fragment) or cytokeratin antibody as a control. TAZ is overexpressed in IDC but not in normal breast tissue.

FIG. 6A. Tumors excised from the fat pad of one pair of mice injected with MCF-KD-715 and MCF7-KD-652 cells, respectively, are pictured.

FIG. 6B. Quantitation of tumor weights. The tumors excised from the fat pad of mice injected with MCF-KD-715 and MCF7-KD-652 cells are weighed and presented. Bars, SEM.

FIG. 8A and FIG. 8B show that TAZ interacts with transcriptional factors (TEAD1, 2, 3 and 4).

DETAILED DESCRIPTION

Figure 1A:
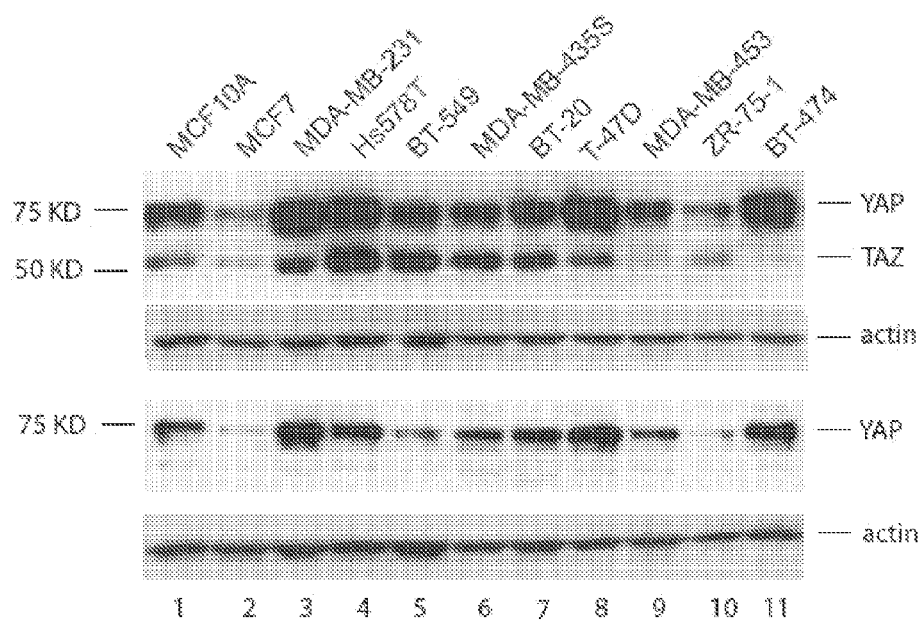
FIG. 1A and FIG. 1B. TAZ is preferentially overexpressed in highly invasive breast cancer cells.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

Use of TAZ in the Treatment and Diagnosis of Breast Cancer

The present invention is based on the demonstration, for the first time, that TAZ plays a role in cancer.

Specifically, we show that TAZ plays a critical role in migration, invasion and tumorigenesis of breast cancer cells. We show in the Examples that TAZ is prominently expressed in human breast cancer cell lines where its expression levels generally correlate with the invasiveness and/or aggressiveness of the cancer cells. High levels of TAZ are detected in highly invasive breast cancer cell lines such as Hs578T, BT549, MDA-MB-453 and MDA-MB231. Lower levels of TAZ are detected in less invasive breast cancer cell lines such as MCF10A, BT20, MCF7, MDA-MB-453, ZR75.1 and BT474.

Accordingly, TAZ may be used as a marker for detection of breast cancer, including basal-like, triple negative and BRCA1-mutated cancer types. The level of TAZ expression may be used as an indicator of cancer, in particular breast cancer such as metastatic, aggressive or invasive breast cancer. The level of TAZ expression may also be used as an indicator of likelihood of such a cancer. We therefore provide for methods of diagnosis or detection of a cancer, particularly breast cancer. We further provide methods of diagnosis and detection of the aggressiveness or invasiveness or the metastatic state, or any combination of these, of such a cancer. The methods may comprise analysis of protein levels (e.g., immunohistochemistry) or RNA levels (e.g., by in situ hybridisation). Such diagnostic and detection methods are described in further detail below.

We show that over-expression of TAZ in immortalized but not transformed MCF10A cells promotes cell proliferation, cell migration and invasion. shRNA mediated knock-down of TAZ in Hs578-t and MCF7 cells suppresses cell migration and invasion. Anchorage-dependent growth in soft-agar and tumorigenesis in vivo of MCF7 cells is suppressed by TAZ knockdown. Culture media harvested from MCF10A cells over-expressing TAZ promotes cell migration. Over-expression of TAZ therefore causes a cancerous phenotype.

Accordingly, we provide for methods of treatment or prophylaxis of an individual suffering from cancer. Restoration of TAZ levels to those in normal tissue may also be used as a means of restoring normal function of breast cells. We therefore provide for the use of TAZ nucleic acids and polypeptides for the treatment of cancers, including breast cancer. Our methods may be used for treatment or prophylaxis of breast cancer or invasive cancer such as invasive breast cancer.

Figure 1B:
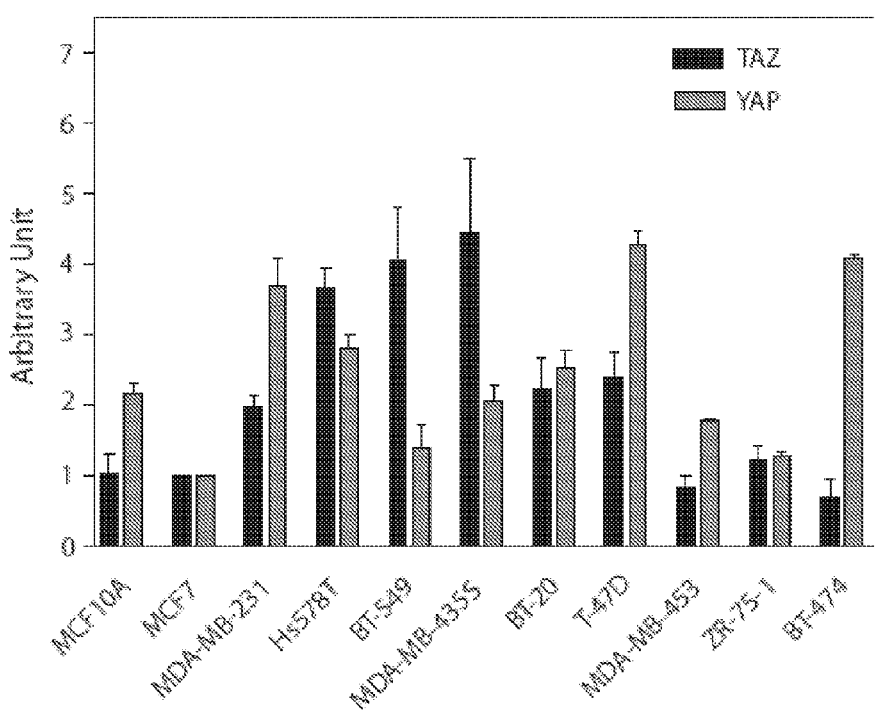

We show in the Examples and FIG. 1 that TAZ is overexpressed in invasive breast cancer lines belonging to the basal-like, triple negative or BRCA1-mutated types. FIG. 1B shows that three (Hs578T, BT-549, and MDA-MB-435S) of the four highly invasive cancer cell lines exhibit high levels of TAZ expression with MDA-MB-231 cells expressing moderate levels.

These four cell lines are shown in Neve et al (2006) to correspond to basal-like or basal B cancer type and represents an invasive breast cancer cell type. This cell type is also referred to as "invasive cell type" or "basal cell type" (BRCA1-mutated is also known as BRCA1-negative). Accordingly, TAZ may be used as a marker for detection of invasive cell type or basal cell type breast cancers.

Unlike ER+ or Her2+ breast cancers, there is no targeted therapy for invasive breast cancers belonging to any of these three breast cancer types. We therefore disclose for the first time a method of treating, in a targeted fashion, an invasive cell type, a basal-like breast cancer, a triple negative breast cancer and a BRCA1-mutated breast cancer type.

We further provide for the use of TAZ in screening for drugs against cancer, particularly breast cancer, more particularly invasive breast cancer. Such screens may involve detecting the modulation of binding between TAZ and TEAD1/2/3/4 by the presence of a candidate molecule.

We provide for a method of identifying a molecule for the treatment or prophylaxis of cancer, including breast cancer such as invasive breast cancer, the method comprising identifying a modulator of an activity or expression of TAZ.

We show in the Examples that TAZ interacts with TEAD1, TEAD2, TEAD3 and TEAD4, and that this interaction is essential for nuclear accumulation of TAZ and oncogenesis.

Accordingly, we provide for a method of identifying a molecule for the treatment or prophylaxis of cancer, including breast cancer such as invasive breast cancer, the method comprising detecting an effect of a candidate molecule on the binding between TAZ and TEAD1, TEAD2, TEAD3 and/or TEAD4. A screen for small molecule inhibitors of TAZ-TEAD binding may be conducted on a library for example.

Alternatively, or in addition, rational design may be employed to produce candidate inhibitors of a TAZ-TEAD interaction. Thus, for example, a peptide from a TAZ binding region of a TEAD (including TEAD1, TEAD2, TEAD3 or TEAD4) may be designed. Similarly, a peptide from a TEAD binding region of a TAZ (including a TEAD1, TEAD2, TEAD3 or TEAD4 binding region) may be designed. Such a peptide could include mutated positions 52 and 53 of TAZ, both of which are shown in the Examples as being important in the binding between TAZ and TEAD.

Putative inhibitors (or candidate inhibitors identified in a screen) may be tested using a number of assays, including a nuclear accumulation assay or a soft agar assay, both of which are described in the Examples.

We further provide for the treatment or prophylaxis of cancer by interfering with or disrupting a TAZ-TEAD interaction. This may be achieved by various means, for example, by introducing a modulator of TAZ, such as a molecule identified from a screen or design described above, to a patient in need thereof.

We show in the Examples that TAZ induces or up-regulates the expression of 8 secreted proteins (IGFBP3, ADAMTS1, CTGF, Cyr61, FSTL1, FN1, FBN1 and FBN2) as well as 4 surface membrane proteins (AXL, ITGB2, CRIM1, and Alcam). Each of these proteins may therefore be used as markers of the oncogenic state. Accordingly, we provide for the detection of a cancer cell or an oncogenic cell or a metastatic cell, the method comprising detecting the expression of a polypeptide selected from the group consisting of: IGFBP3, ADAMTS1, CTGF, Cyr61, FSTL1, FN1, FBN1, FBN2AXL, ITGB2, CRIM1 and Alcam. We also provide for the treatment of cancer, the method comprising modulating the activity or a polypeptide selected from the group consisting of: IGFBP3, ADAMTS1, CTGF, Cyr61, FSTL1, FN1, FBN1, FBN2AXL, ITGB2, CRIM1 and Alcam.

Cells over- and under-expressing TAZ, as well as tissues, organs and organisms comprising these may be used as models for cancer or in screens for anti-cancer agents.

TAZ

TAZ is also referred to as Transcriptional Coactivator with PDZ-Binding Motif or WWTR1. It maps to gene map locus 3q24.

TAZ was first cloned by Kanai et al. (2000) from a HeLa cDNA expression library by screening for 14-3-3-binding proteins (OMIM reference 605066), followed by 5-prime RACE. The deduced protein contains 400 amino acids and has an apparent molecular mass of 45 kD in HeLa cells. It has a putative 14-3-3 protein-binding motif in its N terminus, a central WW domain, and a putative 2-stranded coiled-coil and a PDZ-binding motif in its C terminus.

TAZ shares 91% sequence identity with the mouse Taz protein and 45% identity with YAP (OMIM reference 606608). Northern blot analysis revealed highest expression of a 6-kb transcript in kidney, followed by heart, placenta, and lung. Expression was detected in all tissues tested except thymus and peripheral blood leukocytes. Northern blot analysis of mouse tissues showed a 5.5-kb transcript expressed at highest levels in kidney, lung, liver, and heart; a 2.2-kb transcript was detected in testis. Western blot analysis revealed expression of TAZ in several epithelial and fibroblast cell lines, but not in Jurkat T cells.

Kanai et al. (2000) characterized murine Taz. They found that the interaction of Taz with rat 14-3-3 required Taz phosphorylation on a specific serine residue. Phosphorylation reduced Taz transcriptional coactivation by inducing nuclear export through interaction with 14-3-3. The C-terminal PDZ-binding domain localized Taz to discrete nuclear foci and was required for Taz-stimulated gene transcription. The PDZ-binding domain also mediated Taz interaction with Nherf2 (OMIM reference 606553).

Mesenchymal stem cells are a pluripotent cell type that can differentiate into several distinct lineages. Two key transcription factors, RUNX2 (OMIM reference 600211) and peroxisome proliferator-activated receptor-gamma (PPARG; OMIM reference 601487), drive mesenchymal stem cells to differentiate into either osteoblasts or adipocytes, respectively. Hong et al. (2005) found that TAZ, a 14-3-3-binding protein, coactivates RUNX2-dependent gene transcription while repressing PPARG-dependent gene transcription. By modulating Taz expression in model cell lines, mouse embryonic fibroblasts, and primary mesenchymal stem cells in culture and in zebrafish in vivo, Hong et al. (2005) observed alterations in osteogenic versus adipogenic potential. Hong et al. (2005) concluded that TAZ functions as a molecular rheostat that modulates mesenchymal stem cell differentiation.

Murakami et al. (2005) found that TAZ was a potent TBX5 (OMIM reference 601620) transactivator. TAZ associated with TBX5 and stimulated TBX5-dependent promoters by interacting with the histone acetyltransferases p300 (EP300; OMIM reference 602700) and PCAF (OMIM reference 602303). TBX5 with Holt-Oram syndrome (HOS; OMIM reference 142900)-associated truncation mutations could not be stimulated by TAZ, but TBX5 with HOS-associated point mutations was unimpaired in its ability to respond to TAZ.

By radiation hybrid analysis, Kanai et al. (2000) mapped the TAZ gene to chromosome 3q24.

Where the term "TAZ" is used, this should be taken to refer to any TAZ sequence, including a TAZ protein or a TAZ nucleic acid and any fragment, variant homologue, derivative, variant thereof.

The properties and activities of TAZ are described in this document, for example, in the references.

TAZ Polypeptides

The methods and compositions described here make use of TAZ polypeptides, which are described in detail below.

As used here, the term "TAZ polypeptide" is intended to refer to a sequence having GenBank Accession number NP_056287, NP_598545, NP_001032785, XP_871504, NP_001020040. A "TAZ polypeptide" may comprise or consist of a human TAZ polypeptide, such as the sequence having accession number NP_056287.

Homologues variants and derivatives thereof of any, some or all of these polypeptides are also included. For example, TAZ may include GenBank Accession Number AJ299430.

TAZ polypeptides may be used for a variety of means, for example, administration to an individual suffering from, or suspected to be suffering from, breast cancer, for the treatment thereof. They may also be used for production or screening of anti-TAZ agents such as specific TAZ binding agents, in particular, anti-TAZ antibodies. These are described in further detail below. The expression of TAZ polypeptides may be detected for diagnosis or detection of cancer, in particular breast cancer.

A "polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids.

"Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-inking, cyclization, disulfide bond formation, demethylation, formation of covalent cross-inks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure and Molecular Properties, 2nd Ed., T. E. Creighton, W. H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al., "Analysis for protein modifications and nonprotein cofactors", Meth Enzymol (1990) 182:626-646 and Rattan et al., "Protein Synthesis: Posttranslational Modifications and Aging", Ann NY Acad Sci (1992) 663:48-62.

The term "polypeptide" includes the various synthetic peptide variations known in the art, such as a retroinverso D peptides. The peptide may be an antigenic determinant and/or a T-cell epitope. The peptide may be immunogenic in vivo. The peptide may be capable of inducing neutralizing antibodies in vivo.

As applied to TAZ, the resultant amino acid sequence may have one or more activities, such as biological activities in common with a TAZ polypeptide, for example a human TAZ polypeptide. For example, a TAZ homologue may have a increased expression level in breast cancer cells compared to normal breast cells. In particular, the term "homologue" covers identity with respect to structure and/or function providing the resultant amino acid sequence has TAZ activity. With respect to sequence identity (i.e. similarity), there may be at least 70%, such as at least 75%, such as at least 85%, such as at least 90% sequence identity. There may be at least 95%, such as at least 98%, sequence identity. These terms also encompass polypeptides derived from amino acids which are allelic variations of the TAZ nucleic acid sequence.

Where reference is made to the "activity" or "biological activity" of a polypeptide such as TAZ, these terms are intended to refer to the metabolic or physiological function of TAZ, including similar activities or improved activities or these activities with decreased undesirable side effects. Also included are antigenic and immunogenic activities of the TAZ. Examples of such activities, and methods of assaying and quantifying these activities, are known in the art, and are described in detail elsewhere in this document.

For example, such activities may include any one or more of the following: binding to SLC9A3R2, binding to YWHA, binding to 14-3-3, co-activation of RUNX2-dependent gene transcription, transactivation of TBX5 by TAZ, etc, as described in more detail below.

Other TAZ Polypeptides

TAZ variants, homologues, derivatives and fragments are also of use in the methods and compositions described here.

The terms "variant", "homologue", "derivative" or "fragment" in relation to TAZ include any substitution of, variation of, modification of, replacement of, deletion of or addition of one (or more) amino acid from or to a sequence. Unless the context admits otherwise, references to "TAZ" includes references to such variants, homologues, derivatives and fragments of TAZ.

As used herein a "deletion" is defined as a change in either nucleotide or amino acid sequence in which one or more nucleotides or amino acid residues, respectively, are absent. As used herein an "insertion" or "addition" is that change in a nucleotide or amino acid sequence which has resulted in the addition of one or more nucleotides or amino acid residues, respectively, as compared to the naturally occurring substance. As used herein "substitution" results from the replacement of one or more nucleotides or amino acids by different nucleotides or amino acids, respectively.

TAZ polypeptides as described here may also have deletions, insertions or substitutions of amino acid residues which produce a silent change and result in a functionally equivalent amino acid sequence. Deliberate amino acid substitutions may be made on the basis of similarity in polarity, charge, solubility, hydrophobicity, hydrophilicity, and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the table below. Amino acids in the same block in the second column and in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

TAZ polypeptides may further comprise heterologous amino acid sequences, typically at the N-terminus or C-terminus, such as the N-terminus. Heterologous sequences may include sequences that affect intra or extracellular protein targeting (such as leader sequences). Heterologous sequences may also include sequences that increase the immunogenicity of the TAZ polypeptide and/or which facilitate identification, extraction and/or purification of the polypeptides. Another heterologous sequence that may be used is a polyamino acid sequence such as polyhistidine which may be N-terminal. A polyhistidine sequence of at least 10 amino acids, such as at least 17 amino acids but fewer than 50 amino acids may be employed.

The TAZ polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

TAZ polypeptides as described here are advantageously made by recombinant means, using known techniques. However they may also be made by synthetic means using techniques well known to skilled persons such as solid phase synthesis. Such polypeptides may also be produced as fusion proteins, for example to aid in extraction and purification. Examples of fusion protein partners include glutathione-S-transferase (GST), 6×His (SEQ ID NO: 4), GAL4 (DNA binding and/or transcriptional activation domains) and β-galactosidase. It may also be convenient to include a proteolytic cleavage site between the fusion protein partner and the protein sequence of interest to allow removal of fusion protein sequences, such as a thrombin cleavage site. The fusion protein may be one which does not hinder the function of the protein of interest sequence.

The TAZ polypeptides may be in a substantially isolated form. This term is intended to refer to alteration by the hand of man from the natural state. If an "isolated" composition or substance occurs in nature, it has been changed or removed from its original environment, or both. For example, a polynucleotide, nucleic acid or a polypeptide naturally present in a living animal is not "isolated," but the same polynucleotide, nucleic acid or polypeptide separated from the coexisting materials of its natural state is "isolated", as the term is employed herein.

It will however be understood that the TAZ protein may be mixed with carriers or diluents which will not interfere with the intended purpose of the protein and still be regarded as substantially isolated. A TAZ polypeptide may also be in a substantially purified form, in which case it will generally comprise the protein in a preparation in which more than 90%, for example, 95%, 98% or 99% of the protein in the preparation is a TAZ polypeptide.

By aligning TAZ sequences from different species, it is possible to determine which regions of the amino acid sequence are conserved between different species ("homologous regions"), and which regions vary between the different species ("heterologous regions").

The TAZ polypeptides may therefore comprise a sequence which corresponds to at least part of a homologous region. A homologous region shows a high degree of homology between at least two species. For example, the homologous region may show at least 70%, at least 80%, at least 90% or at least 95% identity at the amino acid level using the tests described above. Peptides which comprise a sequence which corresponds to a homologous region may be used in therapeutic strategies as explained in further detail below. Alternatively, the TAZ peptide may comprise a sequence which corresponds to at least part of a heterologous region. A heterologous region shows a low degree of homology between at least two species.

TAZ Homologues

The TAZ polypeptides disclosed for use include homologous sequences obtained from any source, for example related viral/bacterial proteins, cellular homologues and synthetic peptides, as well as variants or derivatives thereof. Thus polypeptides also include those encoding homologues of TAZ from other species including animals such as mammals (e.g. mice, rats or rabbits), especially primates, more especially humans. More specifically, homologues include human homologues.

In the context of this document, a homologous sequence is taken to include an amino acid sequence which is at least 15, 20, 25, 30, 40, 50, 60, 70, 80 or 90% identical, such as at least 95 or 98% identical at the amino acid level, for example over at least 50 or 100, 200, 300, 400 or 500 amino acids with the sequence of a relevant TAZ sequence.

In particular, homology should typically be considered with respect to those regions of the sequence known to be essential for protein function rather than non-essential neighbouring sequences. This is especially important when considering homologous sequences from distantly related organisms.

Although homology can also be considered in terms of similarity (i.e. amino acid residues having similar chemical properties/functions), in the context of the present document homology may be expressed in terms of sequence identity.

Homology comparisons can be conducted by eye, or more usually, with the aid of readily available sequence comparison programs. These publicly and commercially available computer programs can calculate % identity between two or more sequences.

% identity may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalizing unduly the overall homology score. This is achieved by inserting "gaps" in the sequence alignment to try to maximise local identity or similarity.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, the default values may be used when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Altschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). The GCG Bestfit program may be used.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). The public default values for the GCG package may be used, or in the case of other software, the default matrix, such as BLOSUM62.

Once the software has produced an optimal alignment, it is possible to calculate % homology, such as % sequence identity. The software typically does this as part of the sequence comparison and generates a numerical result.

The terms "variant" or "derivative" in relation to amino acid sequences includes any substitution of, variation of, modification of, replacement of, deletion of or addition of one (or more) amino acids from or to the sequence providing the resultant amino acid sequence retains substantially the same activity as the unmodified sequence, such as having at least the same activity as the TAZ polypeptides.

Polypeptides having the TAZ amino acid sequence disclosed here, or fragments or homologues thereof may be modified for use in the methods and compositions described here. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence. Alternatively, modifications may be made to deliberately inactivate one or more functional domains of the polypeptides described here. Amino acid substitutions may include the use of non-naturally occurring analogues, for example to increase blood plasma half-life of a therapeutically administered polypeptide.

TAZ Fragments

Polypeptides for use in the methods and compositions described here also include fragments of the full length sequence of any of the TAZ polypeptides identified above. Fragments may comprise at least one epitope. Methods of identifying epitopes are well known in the art. Fragments will typically comprise at least 6 amino acids, such as at least 10, 20, 30, 50 or 100 amino acids.

Included are fragments comprising or consisting of, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315 or more residues from a relevant TAZ amino acid sequence.

We further describe peptides comprising a portion of a TAZ polypeptide as described here. Thus, fragments of TAZ and its homologues, variants or derivatives are included. The peptides may be between 2 and 200 amino acids, such as between 4 and 40 amino acids in length. The peptide may be derived from a TAZ polypeptide as disclosed here, for example by digestion with a suitable enzyme, such as trypsin. Alternatively the peptide, fragment, etc may be made by recombinant means, or synthesised synthetically.

A fragment of TAZ may comprise a TAZ fragment of a sequence having accession number NP_056287. A fragment of TAZ may comprise a sequence of TAZ which shares low similarity or identity to YAP (Sudol et al, 1995; GenBank Accession Number: NP_006097). For example a TAZ fragment may comprise amino acid residues 160-229 of TAZ, i.e:

```
                                          (SEQ ID NO: 5)
n qplnhmnlhp aysstpvpqr smavsqpnlv mnhqhqqqma pstlsqqnhp tqnppaglms mpnalttqq
```

Accordingly, such a TAZ fragment may be used to generate probes to preferentially detect TAZ expression, for example, through antibodies generated against such fragments. These antibodies would be expected to bind specifically to TAZ, and are useful in the methods of diagnosis and treatment disclosed here.

Other fragments of TAZ may comprise fragments comprising residue 52 or residue 53 of TAZ, i.e., F52 or F53, or comprising mutations at one or both of these positions. In this regard, the Examples disclose that positions 52 and 53 of TAZ, both of which are occupied by phenylalanine residues, are important in the binding between TAZ and TEAD. They are also shown to be important for nuclear accumulation of TAZ and its oncogenic potential. Accordingly, we disclose fragments of TAZ which comprise a mutation at F52 or a mutation at F53, or both.

Such fragments of TAZ may suitably be provided in the form of peptides, which may be used as anti-TAZ peptides.

Accordingly, we disclose peptides comprising sequences of TAZ which flank either or both of these positions. The peptides may be of any suitable length, such as between 5 to 40 (or more) residues of TAZ sequence. The peptides may comprise, for example, a 5, 10, 15, 20, 25, etc residue long sequence being a subsequence of

```
                                           (SEQ ID NO: 6)
   lealfnsvmn pkpsswrkki lpesffkepd sgshsrqsst dssgghpgpr lag
``` and comprising a mutation at one or both of F52 and F53, highlighted in bold. The mutation could be to any suitable residue, such as alanine.

The peptides may be introduced into a cell, tissue, organ or individual through various means, such as by use of membrane translocation sequences, including for example, the whole sequence or subsequences of the HIV-1-trans-activating protein (Tat), Drosophila Antennapedia homeodomain protein (Antp-HD), Herpes Simplex-1 virus VP22 protein (HSV-VP22), signal-sequence-based peptides, Transportan and Amphiphilic model peptide, among others. These are described in detail in WO 2002/007752.

TAZ and its fragments, homologues, variants and derivatives, may be made by recombinant means. However they may also be made by synthetic means using techniques well known to skilled persons such as solid phase synthesis. The proteins may also be produced as fusion proteins, for example to aid in extraction and purification. Examples of fusion protein partners include glutathione-S-transferase (GST), 6×His (SEQ ID NO: 4), GAL4 (DNA binding and/or transcriptional activation domains) and β-galactosidase. It may also be convenient to include a proteolytic cleavage site between the fusion protein partner and the protein sequence of interest to allow removal of fusion protein sequences. The fusion protein may be one which will not hinder the function of the protein of interest sequence. Proteins may also be obtained by purification of cell extracts from animal cells.

The TAZ polypeptides, variants, homologues, fragments and derivatives disclosed here may be in a substantially isolated form. It will be understood that such polypeptides may be mixed with carriers or diluents which will not interfere with the intended purpose of the protein and still be regarded as substantially isolated. A TAZ variant, homologue, fragment or derivative may also be in a substantially purified form, in which case it will generally comprise the protein in a preparation in which more than 90%, e.g. 95%, 98% or 99% of the protein in the preparation is a protein.

The TAZ polypeptides, variants, homologues, fragments and derivatives disclosed here may be labelled with a revealing label. The revealing label may be any suitable label which allows the polypeptide, etc to be detected. Suitable labels include radioisotopes, e.g. 125I, enzymes, antibodies, polynucleotides and linkers such as biotin. Labelled polypeptides may be used in diagnostic procedures such as immunoassays to determine the amount of a polypeptide in a sample. Polypeptides or labelled polypeptides may also be used in serological or cell-mediated immune assays for the detection of immune reactivity to said polypeptides in animals and humans using standard protocols.

A TAZ polypeptides, variants, homologues, fragments and derivatives disclosed here, optionally labelled, may also be fixed to a solid phase, for example the surface of an immunoassay well or dipstick. Such labelled and/or immobilised polypeptides may be packaged into kits in a suitable container along with suitable reagents, controls, instructions and the like. Such polypeptides and kits may be used in methods of detection of antibodies to the polypeptides or their allelic or species variants by immunoassay.

Immunoassay methods are well known in the art and will generally comprise: (a) providing a polypeptide comprising an epitope bindable by an antibody against said protein; (b) incubating a biological sample with said polypeptide under conditions which allow for the formation of an antibody-antigen complex; and (c) determining whether antibody-antigen complex comprising said polypeptide is formed.

The TAZ polypeptides, variants, homologues, fragments and derivatives disclosed here may be used in in vitro or in vivo cell culture systems to study the role of their corresponding genes and homologues thereof in cell function, including their function in disease. For example, truncated or modified polypeptides may be introduced into a cell to disrupt the normal functions which occur in the cell. The polypeptides may be introduced into the cell by in situ expression of the polypeptide from a recombinant expression vector (see below). The expression vector optionally carries an inducible promoter to control the expression of the polypeptide.

The use of appropriate host cells, such as insect cells or mammalian cells, is expected to provide for such post-translational modifications (e.g. myristolation, glycosylation, truncation, lapidation and tyrosine, serine or threonine phosphorylation) as may be needed to confer optimal biological activity on recombinant expression products. Such cell culture systems in which the TAZ polypeptides, variants, homologues, fragments and derivatives disclosed here are expressed may be used in assay systems to identify candidate substances which interfere with or enhance the functions of the polypeptides in the cell.

TEAD Polypeptides

TEAD1, also known as TEA domain family member 1, has a GenBank Accession Number of NM_021961.4 or NP_068780.1.

TEAD2, also known as TEA domain family member 2, has a GenBank Accession Number of NM_003598.1 or NP_003589.1.

TEAD3, also known as TEA domain family member 3, has a GenBank Accession Number of NM_003214.3 or NP_003205.2.

TEAD 4, also known as TEA domain family member 4, has a number of isoforms. TEAD4 isoform 1 has accession number NM_003213.2 or NP_003204.2. TEAD4 isoform 2 has accession number NM_201441.1 or NP_958849.1. TEAD4 isoform 3 has accession number NM_201443.1 or NP_958851.1.

TAZ Nucleic Acids

The methods and compositions described here may employ, as a means for detecting expression levels of TAZ, TAZ polynucleotides, TAZ nucleotides and TAZ nucleic acids, as well as variants, homologues, derivatives and fragments of any of these. In addition, we disclose particular TAZ fragments useful for the methods of diagnosis described here. The TAZ nucleic acids may also be used for the methods of treatment or prophylaxis described.

The terms "TAZ polynucleotide", "TAZ nucleotide" and "TAZ nucleic acid" may be used interchangeably, and should be understood to specifically include both cDNA and genomic TAZ sequences. These terms are also intended to include a nucleic acid sequence capable of encoding a TAZ polypeptide and/or a fragment, derivative, homologue or variant of this.

Where reference is made to a TAZ nucleic acid, this should be taken as a reference to any member of the TAZ family of nucleic acids. Of particular interest are TAZ nucleic acids selected from the group consisting of: NM_015472, NM_133784, NM_001037696, XM_866411 and NM_001024869.

Also included are any one or more of the nucleic acid sequences set out as "Other TAZ nucleic acid sequences" below.

For example, the TAZ nucleic acid may comprise a human TAZ sequence having GenBank Accession Number NM_015472.

TAZ nucleic acids may be used for a variety of means, for example, administration to an individual suffering from, or suspected to be suffering from, breast cancer, for the treatment thereof. The expression of TAZ nucleic acids may be detected for diagnosis or detection of cancer, in particular breast cancer. TAZ nucleic acids may also be used for the expression or production of TAZ polypeptides.

"Polynucleotide" generally refers to any polyribonucleotide or polydeoxyribonucleotide, which may be unmodified RNA or DNA or modified RNA or DNA. "Polynucleotides" include, without limitation single-and double-stranded DNA, DNA that is a mixture of single-and double-stranded regions, single-and double-stranded RNA, and RNA that is mixture of single-and double-stranded regions, hybrid molecules comprising DNA and RNA that may be single-stranded or, more typically, double-stranded or a mixture of single-and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

It will be understood by the skilled person that numerous nucleotide sequences can encode the same polypeptide as a result of the degeneracy of the genetic code.

As used herein, the term "nucleotide sequence" refers to nucleotide sequences, oligonucleotide sequences, polynucleotide sequences and variants, homologues, fragments and derivatives thereof (such as portions thereof). The nucleotide sequence may be DNA or RNA of genomic or synthetic or recombinant origin which may be double-stranded or single-stranded whether representing the sense or antisense strand or combinations thereof. The term nucleotide sequence may be prepared by use of recombinant DNA techniques (for example, recombinant DNA).

The term "nucleotide sequence" may means DNA.

Other Nucleic Acids

We also provide nucleic acids which are fragments, homologues, variants or derivatives of TAZ nucleic acids. The terms "variant", "homologue", "derivative" or "fragment" in relation to TAZ nucleic acid include any substitution of, variation of, modification of, replacement of, deletion of or addition of one (or more) nucleic acids from or to the sequence of a TAZ nucleotide sequence. Unless the context admits otherwise, references to "TAZ" and "TAZ" include references to such variants, homologues, derivatives and fragments of TAZ.

The resultant nucleotide sequence may encode a polypeptide having any one or more TAZ activity. The term "homologue" may be intended to cover identity with respect to structure and/or function such that the resultant nucleotide sequence encodes a polypeptide which has TAZ activity. For example, a homologue etc of TAZ may have a reduced expression level in breast cancer cells compared to normal breast cells. With respect to sequence identity (i.e. similarity), there may be at least 70%, at least 75%, at least 85% or at least 90% sequence identity. There may be at least 95%, such as at least 98%, sequence identity to a relevant sequence (e.g., a TAZ sequence having GenBank accession number NM_015472). These terms also encompass allelic variations of the sequences.

Variants, Derivatives and Homologues

TAZ nucleic acid variants, fragments, derivatives and homologues may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of this document, it is to be understood that the polynucleotides may be modified by any method available in the art. Such modifications may be carried out in order to enhance the in vivo activity or life span of polynucleotides of interest.

Where the polynucleotide is double-stranded, both strands of the duplex, either individually or in combination, are encompassed by the methods and compositions described here. Where the polynucleotide is single-stranded, it is to be understood that the complementary sequence of that polynucleotide is also included.

The terms "variant", "homologue" or "derivative" in relation to a nucleotide sequence include any substitution of, variation of, modification of, replacement of, deletion of or addition of one (or more) nucleic acid from or to the sequence. Said variant, homologues or derivatives may code for a polypeptide having biological activity. Such fragments, homologues, variants and derivatives of TAZ may comprise modulated activity, as set out above.

As indicated above, with respect to sequence identity, a "homologue" may have at least 5% identity, at least 10% identity, at least 15% identity, at least 20% identity, at least 25% identity, at least 30% identity, at least 35% identity, at least 40% identity, at least 45% identity, at least 50% identity, at least 55% identity, at least 60% identity, at least 65% identity, at least 70% identity, at least 75% identity, at least 80% identity, at least 85% identity, at least 90% identity, or at least 95% identity to the relevant sequence (e.g., a TAZ sequence having GenBank accession number NM_015472).

There may be at least 95% identity, at least 96% identity, at least 97% identity, at least 98% identity or at least 99% identity. Nucleotide identity comparisons may be conducted as described above. A sequence comparison program which may be used is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

Hybridisation

We further describe nucleotide sequences that are capable of hybridising selectively to any of the sequences presented herein, or any variant, fragment or derivative thereof, or to the complement of any of the above. Nucleotide sequences may be at least 15 nucleotides in length, such as at least 20, 30, 40 or 50 nucleotides in length.

The term "hybridization" as used herein shall include "the process by which a strand of nucleic acid joins with a complementary strand through base pairing" as well as the process of amplification as carried out in polymerase chain reaction technologies.

Polynucleotides capable of selectively hybridising to the nucleotide sequences presented herein, or to their complement, may be at least 40% homologous, at least 45% homologous, at least 50% homologous, at least 55% homologous, at least 60% homologous, at least 65% homologous, at least 70% homologous, at least 75% homologous, at least 80% homologous, at least 85% homologous, at least 90% homologous, or at least 95% homologous to the corresponding nucleotide sequences presented herein (e.g., a TAZ sequence having GenBank accession number NM_015472). Such polynucleotides may be generally at least 70%, at least 80 or 90% or at least 95% or 98% homologous to the corresponding nucleotide sequences over a region of at least 20, such as at least 25 or 30, for instance at least 40, 60 or 100 or more contiguous nucleotides.

The term "selectively hybridizable" means that the polynucleotide used as a probe is used under conditions where a target polynucleotide is found to hybridize to the probe at a level significantly above background. The background hybridization may occur because of other polynucleotides present, for example, in the cDNA or genomic DNA library being screening. In this event, background implies a level of signal generated by interaction between the probe and a non-specific DNA member of the library which is less than 10 fold, such as less than 100 fold as intense as the specific interaction observed with the target DNA. The intensity of interaction may be measured, for example, by radiolabelling the probe, e.g. with 32P or 33P or with non-radioactive probes (e.g., fluorescent dyes, biotin or digoxigenin).

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm–5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

We provide nucleotide sequences that may be able to hybridise to the TAZ nucleic acids, fragments, variants, homologues or derivatives under stringent conditions (e.g. 65° C. and 0.1×SSC (1×SSC=0.15 M NaCl, 0.015 M Na$_3$Citrate pH 7.0)).

Generation of Homologues, Variants and Derivatives

Polynucleotides which are not 100% identical to the relevant sequences (e.g., a human TAZ sequence having GenBank accession number NM_015472) but which are also included, as well as homologues, variants and derivatives of TAZ can be obtained in a number of ways. Other variants of the sequences may be obtained for example by probing DNA libraries made from a range of individuals, for example individuals from different populations. For example, TAZ homologues may be identified from other individuals, or other species. Further recombinant TAZ nucleic acids and polypeptides may be produced by identifying corresponding positions in the homologues, and synthesising or producing the molecule as described elsewhere in this document.

In addition, other viral/bacterial, or cellular homologues of TAZ, particularly cellular homologues found in mammalian cells (e.g. rat, mouse, bovine and primate cells), may be obtained and such homologues and fragments thereof in general will be capable of selectively hybridising to human TAZ. Such homologues may be used to design non-human TAZ nucleic acids, fragments, variants and homologues. Mutagenesis may be carried out by means known in the art to produce further variety.

Sequences of TAZ homologues may be obtained by probing cDNA libraries made from or genomic DNA libraries from other animal species, and probing such libraries with probes comprising all or part of any of the TAZ nucleic acids, fragments, variants and homologues, or other fragments of TAZ under conditions of medium to high stringency.

Similar considerations apply to obtaining species homologues and allelic variants of the polypeptide or nucleotide sequences disclosed here.

Variants and strain/species homologues may also be obtained using degenerate PCR which will use primers designed to target sequences within the variants and homologues encoding conserved amino acid sequences within the sequences of the TAZ nucleic acids. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences. It will be appreciated by the skilled person that overall nucleotide homology between sequences from distantly related organisms is likely to be very low and thus in these situations degenerate PCR may be the method of choice rather than screening libraries with labelled fragments the TAZ sequences.

In addition, homologous sequences may be identified by searching nucleotide and/or protein databases using search algorithms such as the BLAST suite of programs.

Alternatively, such polynucleotides may be obtained by site directed mutagenesis of characterised sequences, for example, TAZ nucleic acids, or variants, homologues, derivatives or fragments thereof. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The polynucleotides described here may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 8, 9, 10, or 15, such as at least 20, for example at least 25, 30 or 40 nucleotides in length, and are also encompassed by the term "polynucleotides" as used herein.

Polynucleotides such as a DNA polynucleotides and probes may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Primers comprising fragments of TAZ are particularly useful in the methods of detection of TAZ expression, such as down-regulation of TAZ expression, for example, as associated with breast cancer. Suitable primers for amplification of TAZ may be generated from any suitable stretch of TAZ. Primers which may be used include those capable of amplifying a sequence of TAZ which is specific, i.e., does not have significant homology to YAP for example.

Although TAZ primers may be provided on their own, they are most usefully provided as primer pairs, comprising a forward primer and a reverse primer.

Longer polynucleotides will generally be produced using recombinant means, for example using a PCR (polymerase chain reaction) cloning techniques. This will involve making a pair of primers (e.g. of about 15 to 30 nucleotides), bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector Polynucleotides or primers may carry a revealing label. Suitable labels include radioisotopes such as 32P or 35S, digoxigenin, fluorescent dyes, enzyme labels, or other protein labels such as biotin. Such labels may be added to polynucleotides or primers and may be detected using by techniques known per se. Polynucleotides or primers or fragments thereof labelled or unlabeled may be used by a person skilled in the art in nucleic acid-based tests for detecting or sequencing polynucleotides in the human or animal body.

Such tests for detecting generally comprise bringing a biological sample containing DNA or RNA into contact with a probe comprising a polynucleotide or primer under hybridising conditions and detecting any duplex formed between the probe and nucleic acid in the sample. Such detection may be achieved using techniques such as PCR or by immobilising the probe on a solid support, removing nucleic acid in the sample which is not hybridised to the probe, and then detecting nucleic acid which has hybridised to the probe. Alternatively, the sample nucleic acid may be immobilised on a solid support, and the amount of probe bound to such a support can be detected. Suitable assay methods of this and other formats can be found in for example WO89/03891 and WO90/13667.

Tests for sequencing nucleotides, for example, the TAZ nucleic acids, involve bringing a biological sample containing target DNA or RNA into contact with a probe comprising a polynucleotide or primer under hybridising conditions and determining the sequence by, for example the Sanger dideoxy chain termination method (see Sambrook et al.).

Such a method generally comprises elongating, in the presence of suitable reagents, the primer by synthesis of a strand complementary to the target DNA or RNA and selectively terminating the elongation reaction at one or more of an A, C, G or T/U residue; allowing strand elongation and termination reaction to occur; separating out according to size the elongated products to determine the sequence of the nucleotides at which selective termination has occurred. Suitable reagents include a DNA polymerase enzyme, the deoxynucleotides dATP, dCTP, dGTP and dTTP, a buffer and ATP. Dideoxynucleotides are used for selective termination.

TAZ Control Regions

For some purposes, it may be necessary to utilise or investigate control regions of TAZ. Such control regions include promoters, enhancers and locus control regions. By a control region we mean a nucleic acid sequence or structure which is capable of modulating the expression of a coding sequence which is operatively linked to it.

For example, control regions are useful in generating transgenic animals expressing TAZ. Furthermore, control regions may be used to generate expression constructs for TAZ. This is described in further detail below.

Identification of control regions of TAZ is straightforward, and may be carried out in a number of ways. For example, the coding sequence of TAZ may be obtained from an organism, by screening a cDNA library using a human or mouse TAZ cDNA sequence as a probe. 5' sequences may be obtained by screening an appropriate genomic library, or by primer extension as known in the art. Database searching of genome databases may also be employed. Such 5' sequences which are particularly of interest include non-coding regions. The 5' regions may be examined by eye, or with the aid of computer programs, to identify sequence motifs which indicate the presence of promoter and/or enhancer regions.

Furthermore, sequence alignments may be conducted of TAZ nucleic acid sequences from two or more organisms. By aligning TAZ sequences from different species, it is possible to determine which regions of the amino acid sequence are conserved between different species. Such conserved regions are likely to contain control regions for the gene in question (i.e., TAZ). The mouse and human genomic sequences as disclosed here, for example, a mouse TAZ genomic sequence, may be employed for this purpose. Furthermore, TAZ homologues from other organisms may be obtained using standard methods of screening using appropriate probes generated from the mouse and human TAZ sequences. The genome of the pufferfish (*Takifugu rubripes*) or zebrafish may also be screened to identify a TAZ homologue; thus, several zebrafish sequences of TAZ have been identified (noted above). Comparison of the 5' non-coding region of the Fugu or zebrafish TAZ gene with a mouse or human genomic TAZ sequence may be used to identify conserved regions containing control regions.

Deletion studies may also be conducted to identify promoter and/or enhancer regions for TAZ.

The identity of putative control regions may be confirmed by molecular biology experiments, in which the candidate sequences are linked to a reporter gene and the expression of the reporter detected.

Detection and Diagnostic Methods

Detection of Expression of TAZ

We show in the Examples that the expression of TAZ in breast cancer tissue is up-regulated when compared to normal breast tissue.

Accordingly, we provide for a method of diagnosis of cancer, including breast cancer such as metastatic, aggressive or invasive breast cancer, comprising detecting modulation of expression of TAZ, such as up-regulation of expression of TAZ in a cell or tissue of an individual.

Detection of TAZ expression, activity or amount may be used to provide a method of determining the proliferative state of a cell. Thus, a proliferative cell is one with high levels of TAZ expression, activity or amount compared to a normal cell. Similarly, a non-proliferative cell may be one with low levels TAZ expression, activity or amount compared to a normal cell.

Such detection may also be used to determine whether a cell will become invasive or aggressive. Thus, detection of a high level of TAZ expression, amount or activity of TAZ in the cell may indicate that the cell is likely to be or become aggressive, metastatic or invasive. Similarly, if a cell has a low level of TAZ expression, amount or activity, the cell is not or is not likely to be aggressive, metastatic or invasive.

It will be appreciated that as the level of TAZ varies with the aggressiveness of a tumour, that detection of TAZ expression, amount or activity may also be used to predict a survival rate of an individual with cancer, i.e., high levels of TAZ indicating a lower survival rate or probability and low levels of TAZ indicating a higher survival rate or probability, both as compared to individuals or cognate populations with normal levels of TAZ. Detection of expression, amount or activity of TAZ may therefore be used as a method of prognosis of an individual with cancer.

Detection of TAZ expression, amount or level may be used to determine the likelihood of success of a particular therapy in an individual with a cancer. It may be used in a method of determining whether a tumour in an individual is, or is likely to be, an invasive or metastatic tumour.

The diagnostic methods described in this document may be combined with the therapeutic methods described. Thus, we provide for a method of treatment, prophylaxis or alleviation of cancer in an individual, the method comprising detecting modulation of expression, amount or activity of TAZ in a cell of the individual and administering an appropriate therapy to the individual based on the aggressiveness of the tumour.

Typically, physical examination of the breast and X-ray mammography is used for the detection of breast cancer. A biopsy of the tumour is typically taken for histopathological examination for the diagnosis of breast cancer. Detection of TAZ expression, amount or activity can be used to diagnose, or further confirm the diagnosis of, breast cancer, along with the standard histopathological procedures. This may be especially useful when the histopathological analysis does not yield a clear result.

The presence and quantity of TAZ polypeptides and nucleic acids may be detected in a sample as described in further detail below. Thus, the TAZ associated diseases, including breast cancer, can be diagnosed by methods comprising determining from a sample derived from a subject an abnormally decreased or increased expression, amount or activity, such as a increased expression, amount or activity, of the TAZ polypeptide or TAZ mRNA.

The sample may comprise a cell or tissue sample from an organism or individual suffering or suspected to be suffering from a disease associated with increased, reduced or otherwise abnormal TAZ expression, amount or activity, including spatial or temporal changes in level or pattern of expression, amount or activity. The level or pattern of expression, amount or activity of TAZ in an organism suffering from or suspected to be suffering from such a disease may be usefully compared with the level or pattern of expression, amount or activity in a normal organism as a means of diagnosis of disease.

The sample may comprise a cell or tissue sample from an individual suffering or suspected to be suffering from breast cancer, such as a breast tissue or cell sample.

In some embodiments, an increased level of expression, amount or activity of TAZ is detected in the sample. The level of TAZ may be increased to a significant extent when compared to normal cells, or cells known not to be cancerous. Such cells may be obtained from the individual being tested, or another individual, such as those matched to the tested individual by age, weight, lifestyle, etc.

In some embodiments, the level of expression, amount or activity of TAZ is increased by 10%, 20%, 30% or 40% or more. In some embodiments, the level of expression, amount or activity of TAZ is increased by 45% or more, such as 50% or more, as judged by cDNA hybridisation.

The expression, amount or activity of TAZ may be detected in a number of ways, as known in the art, and as described in further detail below. Typically, the amount of TAZ in a sample of tissue from an individual is measured, and compared with a sample from an unaffected individual. Both TAZ nucleic acid, as well as TAZ polypeptide levels may be measured.

Detection of the amount, activity or expression of TAZ may be used to grade breast cancer. For example, a high level of amount, activity or expression of TAZ may indicate an aggressive, invasive or metastatic cancer. Similarly, a low level of amount, activity or expression of TAZ may indicate a non-aggressive, non-invasive or non-metastatic cancer. Such a grading system may be used in conjunction with established grading systems such as the Elston-Ellis modified Scarff, Bloom, Richardson grading system, also known as the Nottingham grading system (NGS) (5, 6, Haybittle et al, 1982).

This system is the most studied and widely used method of breast tumor grading. The NGS is based on a phenotypic scoring procedure that involves the microscopic evaluation of morphologic and cytologic features of tumor cells including degree of tubule formation, nuclear pleomorphism and mitotic count (6). The sum of these scores stratifies breast tumors into grade I (G1) (well-differentiated, slow-growing), grade II (G2) (moderately differentiated), and grade III (G3) (poorly-differentiated, highly-proliferative) malignancies.

Levels of TAZ gene expression may be determined using a number of different techniques.

Measuring Expression of TAZ at the RNA Level

TAZ gene expression can be detected at the RNA level.

In one embodiment therefore, we disclose a method of detecting the presence of a nucleic acid comprising a TAZ nucleic acid in a sample, by contacting the sample with at least one nucleic acid probe which is specific for the TAZ nucleic acid and monitoring said sample for the presence of the TAZ nucleic acid. For example, the nucleic acid probe may specifically bind to the TAZ nucleic acid, or a portion of it, and binding between the two detected; the presence of the complex itself may also be detected.

Thus, in one embodiment, the amount of TAZ nucleic acid in the form of TAZ mRNA may be measured in a sample. TAZ mRNA may be assayed by in situ hybridization, Northern blotting and reverse transcriptase—polymerase chain reaction. Nucleic acid sequences may be identified by in situ hybridization, Southern blotting, single strand conformational polymorphism, PCR amplification and DNA-chip analysis using specific primers. (Kawasaki, 1990; Sambrook, 1992; Lichter et al, 1990; Orita et al, 1989; Fodor et al., 1993; Pease et al., 1994).

TAZ RNA may be extracted from cells using RNA extraction techniques including, for example, using acid phenol/guanidine isothiocyanate extraction (RNAzol B; Biogenesis), or RNeasy RNA preparation kits (Qiagen). Typical assay formats utilising ribonucleic acid hybridisation include nuclear run-on assays, RT-PCR and RNase protection assays (Melton et al., Nuc. Acids Res. 12:7035. Methods for detection which can be employed include radioactive labels, enzyme labels, chemiluminescent labels, fluorescent labels and other suitable labels.

Each of these methods allows quantitative determinations to be made, and are well known in the art. Decreased or increased TAZ expression, amount or activity can therefore be measured at the RNA level using any of the methods well known in the art for the quantitation of polynucleotides. Any suitable probe from a TAZ sequence, for example, any portion of a suitable human TAZ sequence may be used as a probe.

Sequences for designing TAZ probes may include a sequence having accession number NM_015472, or a portion thereof.

Typically, RT-PCR is used to amplify RNA targets. In this process, the reverse transcriptase enzyme is used to convert RNA to complementary DNA (cDNA) which can then be amplified to facilitate detection.

Many DNA amplification methods are known, most of which rely on an enzymatic chain reaction (such as a polymerase chain reaction, a ligase chain reaction, or a self-sustained sequence replication) or from the replication of all or part of the vector into which it has been cloned.

Many target and signal amplification methods have been described in the literature, for example, general reviews of these methods in Landegren, U. et al., *Science* 242:229-237 (1988) and Lewis, R., *Genetic Engineering News* 10:1, 54-55 (1990).

For example, the polymerase chain reaction may be employed to detect TAZ mRNA.

The "polymerase chain reaction" or "PCR" is a nucleic acid amplification method described inter alia in U.S. Pat. Nos. 4,683,195 and 4,683,202. PCR can be used to amplify any known nucleic acid in a diagnostic context (Mok et al., 1994, *Gynaecologic Oncology* 52:247-252). Self-sustained sequence replication (3SR) is a variation of TAS, which involves the isothermal amplification of a nucleic acid template via sequential rounds of reverse transcriptase (RT), polymerase and nuclease activities that are mediated by an enzyme cocktail and appropriate oligonucleotide primers (Guatelli et al., 1990, *Proc. Natl. Acad. Sci. USA* 87:1874). Ligation amplification reaction or ligation amplification system uses DNA ligase and four oligonucleotides, two per target strand. This technique is described by Wu, D. Y. and Wallace, R. B., 1989, *Genomics* 4:560. In the Qβ Replicase technique, RNA replicase for the bacteriophage Qβ, which replicates single-stranded RNA, is used to amplify the target DNA, as described by Lizardi et al., 1988, *Bio/Technology* 6:1197.

A PCR procedure basically involves: (1) treating extracted DNA to form single-stranded complementary strands; (2) adding a pair of oligonucleotide primers, wherein one primer of the pair is substantially complementary to part of the sequence in the sense strand and the other primer of each pair is substantially complementary to a different part of the same sequence in the complementary antisense strand; (3) annealing the paired primers to the complementary sequence; (4) simultaneously extending the annealed primers from a 3' terminus of each primer to synthesize an extension product complementary to the strands annealed to each primer wherein said extension products after separation from the complement serve as templates for the synthesis of an extension product for the other primer of each pair; (5) separating said extension products from said templates to produce single-stranded molecules; and (6) amplifying said single-stranded molecules by repeating at least once said annealing, extending and separating steps.

Reverse transcription-polymerase chain reaction (RT-PCR) may be employed. Quantitative RT-PCR may also be used. Such PCR techniques are well known in the art, and may employ any suitable primer from a TAZ sequence.

Alternative amplification technology can also be exploited. For example, rolling circle amplification (Lizardi et al., 1998, *Nat Genet.* 19:225) is an amplification technology available commercially (RCAT™) which is driven by DNA polymerase and can replicate circular oligonucleotide probes with either linear or geometric kinetics under isothermal conditions. A further technique, strand displacement amplification (SDA; Walker et al., 1992, *Proc. Natl. Acad. Sci. USA* 80:392) begins with a specifically defined sequence unique to a specific target.

Measuring Expression of TAZ at the Polypeptide Level

TAZ expression can be detected at the polypeptide level.

In a further embodiment, therefore, TAZ expression, amount or activity may be detected by detecting the presence or amount of TAZ polypeptide in a sample. This may be achieved by using molecules which bind to TAZ polypeptide. Suitable molecules/agents which bind either directly or indirectly to the TAZ polypeptide in order to detect its presence include naturally occurring molecules such as peptides and proteins, for example antibodies, or they may be synthetic molecules.

Thus, we disclose a method of detecting the presence of a TAZ polypeptide by contacting a cell sample with an antibody capable of binding the polypeptide and monitoring said sample for the presence of the polypeptide.

For example, the TAZ polypeptide may be detected using an anti-TAZ antibody. Such antibodies may be made by means known in the art (as described in further detail below). For example, an anti-TAZ antibody may comprise an antibody to TAZ amino acid residues 160-229 of TAZ, e.g., an anti-peptide antibody.

This may conveniently be achieved by monitoring the presence of a complex formed between the antibody and the polypeptide, or monitoring the binding between the polypeptide and the antibody. Methods of detecting binding between two entities are known in the art, and include FRET (fluorescence resonance energy transfer), surface plasmon resonance, etc.

Standard laboratory techniques such as immunoblotting as described above can be used to detect altered levels of TAZ protein, as compared with untreated cells in the same cell population.

Gene expression may also be determined by detecting changes in post-translational processing of TAZ polypeptides or post-transcriptional modification of TAZ nucleic acids. For example, differential phosphorylation of TAZ polypeptides, the cleavage of TAZ polypeptides or alternative splicing of TAZ RNA, and the like may be measured. Levels of expression of gene products such as TAZ polypeptides, as well as their post-translational modification, may be detected using proprietary protein assays or techniques such as 2D polyacrylamide gel electrophoresis.

Assay techniques that can be used to determine levels of TAZ protein in a sample derived from a host are well-known to those of skill in the art. Antibodies can be assayed for immunospecific binding by any method known in the art.

The immunoassays which can be used include but are not limited to competitive and non-competitive assay systems using techniques such as western blots, radioimmunoassays, ELISA, sandwich immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays. Such assays are routine in the art (see, for example, Ausubel et al., eds, 1994, Current Protocols in Molecular Biology, Vol. 1, John Wiley & Sons, Inc., New York, which is incorporated by reference herein in its entirety).

The specimen may be assayed for polypeptides/proteins by immunohistochemical and immunocytochemical staining (see generally Stites and Ten, Basic and Clinical Immunology, Appleton and Lange, 1994), ELISA, RIA, immunoblots, Western blotting, immunoprecipitation, functional assays and protein truncation test. Other assay methods include radioimmunoassays, competitive-binding assays, Western Blot analysis and ELISA assays.

ELISA assays are well known to those skilled in the art. Both polyclonal and monoclonal antibodies may be used in the assays. Where appropriate other immunoassays, such as radioimmunoassays (RIA) may be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, 1992.

Detecting Expression of TAZ-Induced Polypeptides

As shown in the Examples, TAZ induces the expression of IGFBP3, ADAMTS1, CTGF, Cyr61, FSTL1, FN1, FBN1, FBN2AXL, ITGB2, CRIM1 and Alcam.

IFGBP3 has a GenBank Accession number AAA52706. ADAMTS1 has a GenBank Accession number AAZ73034. CTGF has a GenBank Accession number CAA63267. Cyr61 has a GenBank Accession number CAG38757. FSTL1 has a GenBank Accession number NP_009016. FN1 has a GenBank Accession number AAH05858. FBN1 has a GenBank Accession number AAH94721. ITGB2 has a GenBank Accession number AAH21077. CRIM1 has a GenBank Accession number AAQ88737. Alcam has a GenBank Accession number AAB59499.

Accordingly, TAZ expression may be detected using the expression of any one or more of these proteins as proxy, at either the nucleic acid level or the polypeptide level, as described above.

More generally, the expression of any one or more of these proteins may be detected as a means of diagnosis of cancer, including breast cancer such as metastatic, aggressive or invasive breast cancer, or an oncogenic or metastatic cell. Detection of such expression may be done by any of the methods described above.

Diagnostic Kits

We also provide diagnostic kits for detecting breast cancer in an individual, or susceptibility to breast cancer in an individual.

The diagnostic kit may comprise means for detecting expression, amount or activity of TAZ in the individual, by any means as described in this document. The diagnostic kit may therefore comprise any one or more of the following: a TAZ polynucleotide or a fragment thereof; a complementary nucleotide sequence to TAZ nucleic acid or a fragment thereof; a TAZ polypeptide or a fragment thereof, or an antibody to a TAZ, such as comprising an anti-TAZ antibody against amino acid residues 160-229 of TAZ, e.g., an anti-peptide antibody human TAZ antibody.

The diagnostic kit may comprise instructions for use, or other indicia. The diagnostic kit may further comprise means for treatment or prophylaxis of breast cancer, such as any of the compositions described in this document, or any means known in the art for treating breast cancer. In particular, the diagnostic kit may comprise an anti-TAZ agent as described, for example obtained by screening. The diagnostic kit may comprise a therapeutic drug such as Tamoxifen (Nolvadex) or its variants such as tamoxifen, tamoxifen citrate or any other antiestrogen or estrogen blocker. The therapeutic drug may also comprise an anti-TAZ antibody.

Prophylactic and Therapeutic Methods

We disclose methods of treating an abnormal conditions, such as breast cancer, related to insufficient amounts of TAZ expression or activity. Methods of preventing breast cancer (i.e., prophylaxis) also suitably employ the same or similar approaches.

In general terms, our methods involve manipulation of cancer cells, by modulating (such as down-regulating) the expression, amount or activity of TAZ in the cell. A step of detecting modulated TAZ expression, amount or activity in a cell may be conducted before or after the manipulation step. The detection step may detect up-regulated or down-regulated TAZ expression, amount or activity. Any of the methods of modulating or down-regulating TAZ, as described in detail elsewhere in this document, may be used.

The method may comprise exposing the cell to an siRNA or shRNA or an anti-TAZ antibody capable of specifically binding to TAZ. TAZ may be modulated by targeting a TAZ target site selected from KD-1 (5'-GATGAATCCGGCCTCG-GCGCC-3' (SEQ ID NO: 1)), KD-650 (5'-AGAGGTACT-TCCTCAATCA-3' (SEQ ID NO: 2)) or KD-652 (5'-AGG-TACTTCCTCAATCACA-3' (SEQ ID NO: 3)).

According to our methods, the cancer cell becomes non-cancerous or the invasive or metastatic cancer cell becomes non-invasive or non-metastatic as a result of the manipulation. The cancer may in particular comprise breast cancer. It may comprise invasive or metastatic cancer such as Invasive Ductal Carcinoma (IDC).

As TAZ is associated with aggressiveness and invasiveness of cancer, the level of TAZ may be detected in a cell of an individual with cancer, in a cancer or non-cancer cell, and the aggressiveness of the cancer assessed. A high level of TAZ amount, expression or activity compared with a normal cell indicates an aggressive or invasive cancer, and a stronger or harsher therapy may therefore be required and chosen. Similarly, a lower level may indicate a less aggressive or invasive therapy.

The approaches described here may be used for therapy of any TAZ related disease in general. TAZ related diseases include proliferative diseases and in particular include cancer. For example, a TAZ related disease may include breast cancer, such as metastatic, invasive or aggressive breast cancer.

A TAZ related disease is defined as being "treated" if a condition associated with the disease is significantly inhibited (i.e., by 50% or more) relative to controls. The inhibition may be by at least 75% relative to controls, such as by 90%, by 95% or 100% relative to controls. The condition may comprise cell proliferation, or it may comprise cell cycle time, cell number, cell migration, cell invasiveness, etc. By the term "treatment" we mean to also include prophylaxis or alleviation of cancer.

TAZ polypeptide represents a target for inhibition of its function for therapy, particularly in tumour cells and other proliferative cells.

The term proliferative disorder is used herein in a broad sense to include any disorder that requires control of the cell cycle. In particular, a proliferative disorder includes malignant and pre-neoplastic disorders. The methods and compositions described here are especially useful in relation to treatment or diagnosis of adenocarcinomas such as: small cell lung cancer, and cancer of the kidney, uterus, prostrate, bladder, ovary, colon and breast. For example, malignancies which may be treatable include acute and chronic leukemias, lymphomas, myelomas, sarcomas such as Fibrosarcoma, myxosarcoma, liposarcoma, lymphangioendotheliosarcoma, angiosarcoma, endotheliosarcoma, chondro sarcoma, osteogenic sarcoma, chordoma, lymphangiosarcoma, synovioma, mesothelioma, leimyosarcoma, rhabdomyosarcoma, colon carcinoma, ovarian cancer, glioma, prostate cancer, pancreatic cancer, breast cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, choriocarcinoma, renal cell carcinoma, hepatoma, bile duct carcinoma seminoma, embryonal carcinoma, cervical cancer, testicular tumour, lung carcinoma, small cell lung carcinoma, bladder carcinoma, epithelial carcinoma, glioma, astrocytoma, ependymoma, pinealoma, hemangioblastoma, acoustic neuoma, medulloblastoma, craniopharyngioma, oligodendroglioma, menangioma, melanoma, neutroblastoma and retinoblastoma.

One possible approach for therapy of such disorders is to express anti-sense constructs directed against TAZ polynucleotides as described here, and administering them to tumour cells, to inhibit gene function and prevent the tumour cell from growing or progressing.

Anti-sense constructs may be used to inhibit gene function to prevent growth or progression in a proliferative cell. Anti-sense constructs, i.e., nucleic acid, such as RNA, constructs complementary to the sense nucleic acid or mRNA, are described in detail in U.S. Pat. No. 6,100,090 (Monia et al.), and Neckers et al., 1992, Crit. Rev Oncog 3(1-2):175-231, the teachings of which document are specifically incorporated by reference.

In a particular example, breast cancer may be treated or prevented by reducing the amount, expression or activity of TAZ in whole or in part, for example by siRNAs capable of binding to and destroying TAZ mRNA. We specifically provide for an anti-TAZ agent which downregulates TAZ by RNA interference. The anti-TAZ agent may comprise a Small Interfering RNA (siRNA) or Short Hairpin RNA (shRNA).

The anti-TAZ agent may comprise shRNA 1 (sense oligonucleotide sequence 5'-GATGAATCCGGCCTCGGCGCC-3' (SEQ ID NO: 1)), shRNA 650 (sense oligonucleotide sequence 5'-AGAGGTACTTCCTCAATCA-3' (SEQ ID NO: 2)) or shRNA 652 (sense oligonucleotide sequence 5'-AGG-TACTTCCTCAATCACA-3' (SEQ ID NO: 3)). Methods of producing such shRNAs are described below and in detail in the Examples.

RNA interference (RNAi) is a method of post transcriptional gene silencing (PTGS) induced by the direct introduction of double-stranded RNA (dsRNA) and has emerged as a useful tool to knock out expression of specific genes in a variety of organisms. RNAi is described by Fire et al., Nature 391:806-811 (1998). Other methods of PTGS are known and include, for example, introduction of a transgene or virus. Generally, in PTGS, the transcript of the silenced gene is synthesised but does not accumulate because it is rapidly degraded. Methods for PTGS, including RNAi are described, for example, in the Ambion.com world wide web site, in the directory "/hottopics/", in the "rnai" file.

Suitable methods for RNAi in vitro are described herein. One such method involves the introduction of siRNA (small interfering RNA). Current models indicate that these 21-23 nucleotide dsRNAs can induce PTGS. Methods for designing effective siRNAs are described, for example, in the Ambion web site described above. RNA precursors such as Short Hairpin RNAs (shRNAs) can also be encoded by all or a part of the TAZ nucleic acid sequence.

Alternatively, double-stranded (ds) RNA is a powerful way of interfering with gene expression in a range of organisms that has recently been shown to be successful in mammals (Wianny and Zernicka-Goetz, 2000, Nat Cell Biol 2:70-75). Double stranded RNA corresponding to the sequence of a TAZ polynucleotide can be introduced into or expressed in oocytes and cells of a candidate organism to interfere with TAZ activity.

Other methods of modulating TAZ gene expression are known to those skilled in the art and include dominant negative approaches. Thus, another approach is to use non-functional variants of TAZ polypeptide in this document that compete with the endogenous gene product resulting in inhibition of function.

TAZ gene expression may also be modulated by as introducing peptides or small molecules which inhibit gene expression or functional activity. Thus, compounds identified by the assays described here as binding to or modulating, such as down-regulating, the amount, activity or expression of TAZ polypeptide may be administered to tumour or proliferative cells to prevent the function of TAZ polypeptide. Such a compound may be administered along with a pharmaceutically acceptable carrier in an amount effective to down-regulate expression or activity TAZ, or by activating or down-regulating a second signal which controls TAZ expression, activity or amount, and thereby alleviating the abnormal condition.

Suitable antibodies against TAZ polypeptide as described herein may also be used as therapeutic agents. An anti-TAZ antibody may comprise a rabbit anti-TAZ antibody against amino acids 160-229 of TAZ. Furthermore, the anti-TAZ antibody may comprise any one or more of the following: a rabbit anti-TAZ antibody (catalogue number 2149S, Cell Signaling Technology, Danvers, Mass., USA), rabbit polyclonal anti-TAZ antibody (catalogue number NB110-58359SS, Novus Biological, Littleton, Colo., USA), Mouse Monoclonal anti-TAZ [1B10] (catalogue number H00006901-M12, Novus Biological, Littleton, Colo., USA), Rabbit anti-Human TAZ Polyclonal Antibody (catalogue number LS-B94, LifeSpan Biosciences, Inc., Seattle, Wash., USA) or p-TAZ (Ser 89)-R (catalogue number sc-17610-R, Santa Cruz Biotechnology, Santa Cruz, Calif., USA).

Alternatively, gene therapy may be employed to control the endogenous production of TAZ by the relevant cells such as breast cells in the subject. For example, a polynucleotide encoding a TAZ siRNA or a portion of this may be engineered for expression in a replication defective retroviral vector, as discussed below. The retroviral expression construct may then be isolated and introduced into a packaging cell transduced with a retroviral plasmid vector containing RNA encoding an anti-TAZ siRNA such that the packaging cell now produces infectious viral particles containing the sequence of interest. These producer cells may be administered to a subject for engineering cells in vivo and regulating expression of the TAZ polypeptide in vivo. For overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

In some embodiments, the level of TAZ is decreased in a breast cell. Furthermore, in such embodiments, treatment may be targeted to, or specific to, breast cells. The expression of TAZ may be specifically decreased only in diseased breast cells (i.e., those cells which are cancerous), and not substantially in other non-diseased breast cells. In these methods, expression of TAZ may be not substantially reduced in other cells, i.e., cells which are not breast cells. Thus, in such embodiments, the level of TAZ remains substantially the same or similar in non-breast cells in the course of or following treatment.

Breast cell specific reduction of TAZ levels may be achieved by targeted administration, i.e., applying the treatment only to the breast cells and not other cells. However, in other embodiments, down-regulation of TAZ expression in breast cells (and not substantially in other cell or tissue types) is employed. Such methods may advantageously make use of breast specific expression vectors, for breast specific expression of for example siRNAs, as described in further detail below.

Breast-specific Expression of a Transgene (Anti-TAZ siRNA)

Cancer gene therapy has to selectively target tumour tissues so as to reduce undesired side effects in normal tissue. Targeting transgene expression to malignant tissues requires the use of specific regulatory elements including promoters based on tumour biology, tissue-specific promoters and inducible regulatory elements (A1).

Promoters Based on Tumour Biology

Certain genes are upregulated in breast cancer. The promoters of these genes can be used to drive tumour-selective expression of a transgene using a recombinant replication-defective retroviral vectors. Examples of such genes include the vascular endothelial growth factor (VEGF), vascular endothelial growth factor receptor-1 (VEGFR-1) and VEGFR-2, which are known to be upregulated in breast cancer in a tumour-stage dependent manner (A2). c-erbB2 oncogene is selectively upregulated in breast carcinomas (A3, A6). L-plastin, a human actin-binding protein is constitutively and abundantly expressed in malignant epithelial cells but not in normal tissue, except for low-level expression in mature hematopoietic cells (A4). Anti-apoptotic gene Bcl-2 has been found to be upregulated in breast cancer cells (A5). Human breast tumours express high levels of MUC1 compared to normal breast tissues (A7).

Tissue Specific Promoters

Certain genes are expressed specifically in breast tissues. Examples of such genes are the human α-lactalbumin (ALA) and ovine β-lactoglobulin (BLG). The promoters of such genes can be used to drive the expression of transgenes in adenoviral vectors in a breast cancer cell-specific manner (A8). Gene therapy for breast carcinoma may be approached by tailoring a virus with affinity to this tissue, such as the mouse mammary tumour virus (MMTV). The glucorticoid-responsive long terminal repeats (LTR) of this retrovirus can be used as promoter for glucocorticoid-induced the expression of a transgene (A9).

Inducible Promoters

Inducible promoters are used as mediators of transient transgene expression. Various stress genes are upregulated in breast tumours upon irradiation or chemotherapeutic treatment. Examples of such stress genes are heat shock protein (HSP) (A10) and multidrug resistance gene-1 (MDR-1) (A11). The promoters of these genes can therefore be used to drive the tumour specific expression of a transgene in breast cancers that have been subjected to irradiation or chemotherapy.

Transcriptionally targeted gene therapy is usually achieved by direct intratumour injection of a replication-defective adenoviral expression vector containing the transgene of interest (A6, A12, A13). The transgene can also be delivered by intratumoural injection as a lipid complex with cationic liposomes (A14, A15).

Breast Cancer

According to the methods and compositions described here, TAZ is useful for diagnosing or treating breast cancer. Where this document refers to "cancer", this should be taken to include metastatic, aggressive or invasive cancer.

There are several types of breast cancer. The most common is ductal carcinoma, which begins in the lining of the milk ducts of the breast. Another type, lobular carcinoma, begins in the lobules where breast milk is produced. If a malignant tumor invades nearby tissue, it is known as infiltrating or invasive cancer. When breast cancer spreads outside the breast, cancer cells often are found in the lymph nodes under the arm. Breast cancer cells may spread beyond the breast such as to other lymph nodes, the bones, liver, or lungs.

The recognised stages of breast cancer comprise:

Stage 0: Very early breast cancer. This type of cancer has not spread within or outside the breast. It is sometimes called DCIS, LCIS, or breast cancer in situ or non-invasive cancer.

Stage I: The cancer is no larger than about 1 inch in size and has not spread outside the breast. (also described as early breast cancer.)

Stage II: The presence of any of the following: the cancer is no larger than 1 inch, but has spread to the lymph nodes under the arm; the cancer is between 1 and 2 inches. It may or may not have spread to the lymph nodes under the arm; the cancer is larger than 2 inches, but has not spread to the lymph nodes under the arm.

Stage III and Stage IIIA: The presence of any of the following: the cancer is smaller than 2 inches and has spread to the lymph nodes under the arm, the cancer also is spreading further to other lymph nodes; the cancer is larger than 2 inches and has spread to the lymph nodes under the arm.

Stage IIIB: The presence of any of the following: the cancer has spread to tissues near the breast (skin, chest wall, including the ribs and the muscles in the chest); the cancer has spread to lymph nodes inside the chest wall along the breast bone.

Stage IV: The cancer has spread to other parts of the body, most often the bones, lungs, liver, or brain. Or, the tumor has spread locally to the skin and lymph nodes inside the neck, near the collarbone.

Inflammatory Breast Cancer: Inflammatory breast cancer is a rare, but very serious, aggressive type of breast cancer. The breast may look red and feel warm. There may be ridges, welts, or hives on the breast; or the skin may look wrinkled. It is sometimes misdiagnosed as a simple infection.

Recurrent Breast Cancer: Recurrent disease means that the cancer has come back (recurred) after it has been treated. It may come back in the breast, in the soft tissues of the chest (the chest wall), or in another part of the body.

Breast Cancer in situ—DCIS and LCIS

Many breast cancers being found are very early cancers known as breast cancer in situ or noninvasive cancer. Most of these cancers are found by mammography. These very early cell changes may become invasive breast cancer. Two types of breast cancer in situ include the following:

DCIS (ductal carcinoma in situ), which means that abnormal cells are found only in the lining of a milk duct of the breast. The abnormal cells have not spread outside the duct. They have not spread within the breast, beyond the breast, to the lymph nodes under the arm, or to other parts of the body. There are several types of DCIS. If not removed, some types may change over time and become invasive cancers. Some may never become invasive cancers.

(DCIS is Sometimes Called Intraductal Carcinoma.)

LCIS (lobular carcinoma in situ), which means that abnormal cells are found in the lining of a milk lobule. Although LCIS is not considered to be actual breast cancer at this noninvasive stage, it is a warning sign of increased risk of developing invasive cancer. LCIS is sometimes found when a biopsy is done for another lump or unusual change that is found on a mammogram. Patients with LCIS have a 25 percent chance of developing breast cancer in either breast during the next 25 years.

Microcalcifications are very small specks of calcium that can't be felt, but can be seen on a mammogram. They are formed by rapidly dividing cells. When they are clustered in one area of the breast, this could be an early sign of breast cancer in situ. About half of the breast cancers found by mammography appear as clusters of microcalcifications. The other half appear as lumps.

Diagnosis

Our diagnostic methods may be used in conjunction with any known method of diagnosis of breast cancer, including detecting of mutations in either or both of the known breast cancer genes BRCA1 and BRCA2. Alternatively, or in addition, the diagnosis may be carried out by detection of Her2 expression, for example by use of anti-Her2 antibody.

Treatment

Known treatments for breast cancer may consist of any one or more of the following: Surgery, radiation therapy, chemotherapy, high-dose chemotherapy, hormonal therapy and immunotherapy. Accordingly, any of the treatment methods described here may be combined with any one or more of the preceding known therapies. In addition, any one or more of the following general therapies known to be effective for treatment or alleviation of cancer may be used.

Nonspecific Immunomodulating Agents

Nonspecific immunomodulating agents are substances that stimulate or indirectly augment the immune system. Often, these agents target key immune system cells and cause secondary responses such as increased production of cytokines and immunoglobulins. Two nonspecific immunomodulating agents used in cancer treatment are *bacillus* Calmette-Guerin (BCG) and levamisole. The anti-TAZ agents described here may be used in conjunction with any of such nonspecific immunomodulating agents.

Biological Response Modifiers

Some antibodies, cytokines, and other immune system substances can be produced in the laboratory for use in cancer treatment. These substances are often called biological response modifiers (BRMs). They alter the interaction between the body's immune defenses and cancer cells to boost, direct, or restore the body's ability to fight the disease. BRMs include interferons, interleukins, colony-stimulating factors, monoclonal antibodies, and vaccines. The anti-TAZ agents described here may be used in conjunction with any of such biological response modifiers.

Interferons (IFN)

There are three major types of interferons—interferon alpha, interferon beta, and interferon gamma; interferon alpha is the type most widely used in cancer treatment.

Interferons can improve the way a cancer patient's immune system acts against cancer cells. In addition, interferons may act directly on cancer cells by slowing their growth or promoting their development into cells with more normal behavior. Some interferons may also stimulate NK cells, T cells, and macrophages, boosting the immune system's anticancer function.

The anti-TAZ agents described here may be used in conjunction with any of such interferons.

Interleukins (IL)

Like interferons, interleukins are cytokines that occur naturally in the body. Many interleukins have been identified; interleukin-2 (IL-2 or aldesleukin) has been the most widely studied in cancer treatment. IL-2 stimulates the growth and activity of many immune cells, such as lymphocytes, that can destroy cancer cells.

The anti-TAZ agents described here may be used in conjunction with any of such interleukins.

Colony-Stimulating Factors (CSFs)

Colony-stimulating factors (CSFs) (sometimes called hematopoietic growth factors) usually do not directly affect tumor cells; rather, they encourage bone marrow stem cells to divide and develop into white blood cells, platelets, and red blood cells. Bone marrow is critical to the body's immune system because it is the source of all blood cells.

G-CSF (filgrastim) and GM-CSF (sargramostim) can increase the number of white blood cells, thereby reducing the risk of infection in patients receiving chemotherapy. G-CSF and GM-CSF can also stimulate the production of stem cells in preparation for stem cell or bone marrow transplants; Erythropoietin can increase the number of red blood cells and reduce the need for red blood cell transfusions in patients receiving chemotherapy; and Oprelvekin can reduce the need for platelet transfusions in patients receiving chemotherapy.

The anti-TAZ agents described here may be used in conjunction with any of such colony-stimulating factors.

Monoclonal Antibodies (MOABs)

Herceptin is used to treat metastatic breast cancer in patients with tumors that produce excess amounts of a protein called HER-2. (Approximately 25 percent of breast cancer tumors produce excess amounts of HER-2). In particular embodiments, the methods of treatment described here may be used in combination with administration of anti-Her2 antibody, for example, Herceptin, to the individual concerned.

The anti-TAZ agents described here may be used in conjunction with any of such monoclonal antibodies.

Her2/Neu

The HER-2/neu (erbB-2) gene product is a 185-kDA transmembrane receptor tyrosine kinase that belongs to the family of receptors for epidermal growth factor. It is described in some detail in Reese, D. M., et al., Stem Cells, 15, 1-8 (1997) which is incorporated herein by reference.

Recently, enormous attention has been given to the importance of HER-2/neu in breast cancer. HER-2/neu is overexpressed in 20-30% of human breast cancers and the increased expression has been associated with poor prognosis. The discovery of this has led to the development of HERCEPTIN, an antibody to HER-2/neu, which in tests has been found to lengthen remission time in metastatic breast cancer. HER-2/neu is a cell-surface receptor that transmits growth signals to the cell nucleus. HERCEPTIN appears to block these signals thereby apparently inhibiting proliferation of cells mediated by HER-2/neu in HER-2/neu positive breast cancer.

Overexpression of HER-2/neu has also been found in a portion of ovarian cancers, gastric cancers, endometrial cancers, salivary cancers, pancreatic cancers, prostate cancers, colorectal cancers, and non-small-cell lung cancers. The other cancers associated with overexpression of HER-2-neu are potentially treatable with HERCEPTIN.

Accordingly, our methods of diagnosis may be combined with detection of over-expression of Her2 in an individual. Likewise, the methods of treatment described here may include administration of Herceptin to an individual, in addition to decreasing activity, amount or expression of TAZ. We therefore provide a combination of TAZ nucleic acid or TAZ polypeptide, together with an anti-Her2 antibody. We also provide a combination of an anti-TAZ antibody together with an anti-Her2 antibody. In some embodiments, the anti-Her2 antibody comprises Herceptin.

Screening for Anti-TAZ Agents

Identifying TAZ Modulators, Agonists and Antagonists

Antagonists, in particular, small molecules may be used to specifically inhibit TAZ for use as anti-TAZ agents.

We therefore disclose TAZ antagonists and small molecule TAZ inhibitors, as well as assays for screening for these. Antagonists of TAZ may be screened by detecting modulation, such as down regulation, of binding or other TAZ activity. Antagonists of TAZ may also be screened by detecting modulation of binding between TAZ and a TAZ binding protein, such as TEAD1, TEAD2, TEAD3 or TEAD4.

We therefore provide a compound capable of down-regulating the expression, amount or activity TAZ polypeptide. Such a compound may be used in the methods and compositions described here for treating or preventing cancer, particularly breast cancer.

TAZ may therefore be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., *Current Protocols in Immunology* 1(2):Chapter 5 (1991). Furthermore, screens may be conducted to identify factors which influence the expression of TAZ, in particular in breast cells.

In general, the assays for agonists and antagonists rely on determining the effect of candidate molecules on one or more activities of TAZ. An assay may involve assaying TAZ activity in the presence of a candidate molecule, and optionally in the absence of the candidate molecule, or in the presence of a molecule known to inhibit or activate a TAZ activity. Assays or modulators of activity of TAZ may be detected by detecting binding of TAZ with another entity, such as a TAZ binding protein. Examples of TAZ binding proteins include TEAD1, TEAD2, TEAD3 and TEAD4. Accordingly, a screen for a modulator of TAZ activity such as a TAZ antagonist may be conducted by providing TAZ and a TEAD polypeptide and detecting the binding between them, in the presence and absence of a candidate molecule. Molecules of interest are those that interrupt, diminish, abolish, disrupt or in any way modulate the binding between TAZ and a TEAD polypeptide.

We have demonstrated that expression of TAZ is increased in breast cancer cells; accordingly, control of TAZ expression may be employed to treat breast cancer and other cancers. Therefore, it is desirous to find compounds and drugs which stimulate the expression and/or activity of TAZ, or which can inhibit the function of this protein. In general, agonists and antagonists are employed for therapeutic and prophylactic purposes for any known cancer, in particular, breast cancer.

By "down-regulation" we include any negative effect on the behaviour being studied; this may be total or partial. Thus, where binding is being detected, candidate antagonists are capable of reducing, ameliorating, or abolishing the binding between two entities. The down-regulation of binding (or any other activity) achieved by the candidate molecule may be at least 10%, such as at least 20%, at least 30%, at least 40%, at least 50%, at least 60%, at least 70%, at least 80%, at least 90% or more compared to binding (or which ever activity) in the absence of the candidate molecule. Thus, a candidate molecule suitable for use as an antagonist is one which is capable of reducing by 10% more the binding or other activity.

The term "compound" refers to a chemical compound (naturally occurring or synthesised), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. The compound may be an antibody.

Examples of potential antagonists of TAZ include antibodies, small molecules, nucleotides and their analogues, including purines and purine analogues, oligonucleotides or proteins which are closely related to a binding partner of TAZ, e.g., a fragment of the binding partner, or small molecules which bind to the TAZ polypeptide but do not elicit a response, so that the activity of the polypeptide is prevented, etc.

Screening Kits

The materials necessary for such screening to be conducted may be packaged into a screening kit.

Such a screening kit is useful for identifying agonists, antagonists, ligands, receptors, substrates, enzymes, etc. for TAZ polypeptides or compounds which decrease or enhance the production of TAZ. The screening kit may comprise: (a) a TAZ polypeptide; (b) a recombinant cell expressing a TAZ polypeptide; (c) an antibody to TAZ polypeptide; or (d) a TAZ binding protein such as TEAD1, TEAD2, TEAD3 or TEAD4. The screening kit may comprise a library. The screening kit may comprise any one or more of the components needed for screening, as described below. The screening kit may optionally comprise instructions for use.

Screening kits may also be provided which are capable of detecting TAZ expression at the nucleic acid level. Such kits may comprise a primer for amplification of TAZ, or a pair of primers for amplification. The primer or primers may be chosen from any suitable sequence, for example a portion of the TAZ sequence. Methods of identifying primer sequences are well known in the art, and the skilled person will be able to design such primers with ease. The kits may comprise a nucleic acid probe for TAZ expression, as described in this document. The kits may also optionally comprise instructions for use.

Rational Design

Rational design of candidate compounds likely to be able to interact with TAZ may be based upon structural studies of the molecular shapes of a TAZ polypeptide.

For example, we have established that residues 52 and 53 of TAZ are involved in binding between TAZ and TEAD polypeptides. The Examples show that mutants of TAZ at either of these positions (e.g., F52A, F53A) disrupt the binding between TAZ and TEAD polypeptides, disrupt the nuclear localisation of TAZ and disrupt the oncongenic potential of TAZ.

Accordingly, molecules comprising the sequence of TAZ surrounding positions 52 and 53 may be used as modulators of TAZ activity, such as by modulating the binding between TAZ and TEAD polypeptides, e.g., by competitive binding. Such molecules may include a peptide comprising position 52 or position 53 or both of TAZ.

Furthermore, a peptide from a TAZ binding region of a TEAD (including TEAD1, TEAD2, TEAD3 or TEAD4) may be designed and tested for modulation of TAZ-TEAD binding activity.

A further means for determining which sites interact with specific other proteins is a physical structure determination, e.g., X-ray crystallography or two-dimensional NMR techniques.

These will provide guidance as to which amino acid residues form molecular contact regions. For a detailed description of protein structural determination, see, e.g., Blundell and Johnson (1976) *Protein Crystallography*, Academic Press, New York.

Polypeptide Binding Assays

Modulators and antagonists of TAZ activity or expression may be identified by any means known in the art.

In their simplest form, the assays may simply comprise the steps of mixing a candidate compound with a solution containing a TAZ polypeptide to form a mixture, measuring activity of TAZ polypeptide in the mixture, and comparing the activity of the mixture to a standard.

Furthermore, molecules may be identified by their binding to TAZ, in an assay which detects binding between TAZ and the putative molecule.

One type of assay for identifying substances that bind to a TAZ polypeptide described here involves contacting the TAZ polypeptide, which is immobilised on a solid support, with a non-immobilised candidate substance determining whether and/or to what extent the TAZ polypeptide of interest and candidate substance bind to each other. Alternatively, the candidate substance may be immobilised and the TAZ polypeptide as set out in this document non-immobilised.

The binding of the substance to the TAZ polypeptide can be transient, reversible or permanent. The substance may bind to the polypeptide with a Kd value which is lower than the Kd value for binding to control polypeptides (e.g., polypeptides known to not be involved in cancer growth or progression). The Kd value of the substance may be 2 fold less than the Kd value for binding to control polypeptides, such as a Kd value 100 fold less or a Kd 1000 fold less than that for binding to the control polypeptide.

In an example assay method, the TAZ polypeptide may be immobilised on beads such as agarose beads. Typically this may be achieved by expressing the TAZ polypeptide as a GST-fusion protein in bacteria, yeast or higher eukaryotic cell lines and purifying the GST-TAZ fusion protein from crude cell extracts using glutathione-agarose beads (Smith and Johnson, 1988; Gene 67(10):31-40). As a control, binding of the candidate substance, which is not a GST-fusion protein, to an immobilised polypeptide may be determined in the absence of the TAZ polypeptide. The binding of the candidate substance to the immobilised TAZ polypeptide may then be determined. This type of assay is known in the art as a GST pulldown assay. Again, the candidate substance may be immobilised and the TAZ polypeptide non-immobilised.

It is also possible to perform this type of assay using different affinity purification systems for immobilising one of the components, for example Ni-NTA agarose and histidine-tagged components.

Binding of the polypeptide to the candidate substance may be determined by a variety of methods well-known in the art. For example, the non-immobilised component may be labeled (with for example, a radioactive label, an epitope tag or an enzyme-antibody conjugate). Alternatively, binding may be determined by immunological detection techniques. For example, the reaction mixture can be Western blotted and the blot probed with an antibody that detects the non-immobilised component. ELISA techniques may also be used.

Candidate substances are typically added to a final concentration of from 1 to 1000 nmol/ml, such as from 1 to 100 nmol/ml. In the case of antibodies, the final concentration used is typically from 100 to 500 μg/ml, such as from 200 to 300 μg/ml.

Modulators and antagonists of TAZ may also be identified by detecting modulation of binding between TAZ and any molecule to which this polypeptide binds, or modulation of any activity consequential on such binding or release.

Cell Based Assays

A cell based assay may simply test binding of a candidate compound wherein adherence to the cells bearing the TAZ polypeptide is detected by means of a label directly or indirectly associated with the candidate compound or in an assay involving competition with a labeled competitor.

Further, these assays may test whether the candidate compound results in a signal generated by binding to the TAZ polypeptide, using detection systems appropriate to the cells bearing the polypeptides at their surfaces. Inhibitors of activation are generally assayed in the presence of a known agonist and the effect on activation by the agonist by the presence of the candidate compound is observed. Such a signal could include nuclear localisation, which may be assayed as described in the Examples. Another signal which may be detected is oncogenic activity, which may be assayed by a soft agar assay, as described in the Examples.

Another method of screening compounds utilises eukaryotic or prokaryotic host cells which are stably transformed with recombinant DNA molecules expressing a library of compounds. Such cells, either in viable or fixed form, can be used for standard binding-partner assays. See also Parce et al. (1989) Science 246:243-247; and Owicki et al. (1990) Proc. Nat'l Acad. Sci. USA 87; 4007-4011, which describe sensitive methods to detect cellular responses.

Competitive assays are particularly useful, where the cells expressing the library of compounds are contacted or incubated with a labelled antibody known to bind to a TAZ polypeptide, such as 125I-antibody, and a test sample such as a candidate compound whose binding affinity to the binding composition is being measured. The bound and free labelled binding partners for the TAZ polypeptide are then separated to assess the degree of binding. The amount of test sample bound is inversely proportional to the amount of labelled antibody binding to the TAZ polypeptide.

Any one of numerous techniques can be used to separate bound from free binding partners to assess the degree of binding. This separation step could typically involve a procedure such as adhesion to filters followed by washing, adhesion to plastic following by washing, or centrifugation of the cell membranes.

The assays may involve exposing a candidate molecule to a cell, such as a breast cell, and assaying expression of TAZ by any suitable means. Molecules which down-regulate the expression of TAZ in such assays may be optionally chosen for further study, and used as drugs to down-regulate TAZ expression. Such drugs may be usefully employed to treat or prevent breast cancer.

cDNA encoding TAZ protein and antibodies to the proteins may also be used to configure assays for detecting the effect of added compounds on the production of TAZ mRNA and protein in cells. For example, an ELISA may be constructed for measuring secreted or cell associated levels of TAZ polypeptide using monoclonal and polyclonal antibodies by standard methods known in the art, and this can be used to discover agents which may inhibit or enhance the production of TAZ protein (also called antagonist or agonist, respectively) from suitably manipulated cells or tissues. Standard methods for conducting screening assays are well understood in the art.

Activity Assays

Assays to detect modulators or antagonists typically involve detecting modulation of any activity of TAZ, in the presence, optionally together with detection of modulation of activity in the absence, of a candidate molecule.

The activity that may be detected can comprise any TAZ-dependent activity, such as binding activity. TAZ is known to bind to SLC9A3R2 via the PDZ motif at the plasma membrane, and binding activity of TAZ to SLC9A3R2 may be assayed by means known in the art, for example, GST-pulldown assays. One of TAZ and SLC9A3R2 may be immobilised and the other radiolabelled. Binding of TAZ to SLC9A3R2 may then be detected by assaying captured radioactivity on exposure of TAZ to SLC9A3R2.

Similarly, TAZ is known to bind to YWHAZ in vivo and in vitro through the phosphoserine-binding motif RSHSSP (SEQ ID NO: 7). Accordingly, detection of binding of TAZ to YWHAZ may be detected through means known in the art, such as the techniques described above, and modulation of such binding may be assayed to detect modulators or antagonists of TAZ.

TAZ is shown to bind to TEAD polypeptides, including TEAD1, TEAD2, TEAD3 and TEAD4. Therefore, binding between TAZ and TEAD polypeptides may be detected by means known in the art, such as the techniques described in this document, and modulation of such binding may be assayed to detect modulators or antagonists of TAZ.

Assays which detect specific biological activities of TAZ may also be used. The assays typically involve contacting a candidate molecule (e.g., in the form of a library) with TAZ whether in the form of a polypeptide, a nucleic acid encoding the polypeptide, or a cell, organelle, extract, or other material comprising such, with a candidate modulator. The relevant activity of TAZ (as described below) may be detected, to establish whether the presence of the candidate modulator has any effect.

Alternatively, or in addition, assaying of the binding between TAZ and 14-3-3 as described by Kanai (2000) may be used to detect modulators of TAZ. Hong et al. (2005) describes assays that detect TAZ-dependent co-activation of RUNX2-dependent gene transcription. Murakami et al. (2005) describes transactivation of TBX5 by TAZ.

The assays described by Kanai (2000), Hong et al (2005) or Murakami et al. (2005) may be performed in the presence or absence of a candidate modulator and the appropriate activity detected to detect modulation of TAZ activity and hence identification of a candidate modulator and/or antagonist of TAZ.

Promoter binding assays to detect candidate modulators which bind to and/or affect the transcription or expression of TAZ may also be used. Candidate modulators may then be chosen for further study, or isolated for use. Details of such screening procedures are well known in the art, and are for example described in, Handbook of Drug Screening, edited by Ramakrishna Seethala, Prabhavathi B. Fernandes (2001, New York, N.Y., Marcel Dekker, ISBN 0-8247-0562-9).

The screening methods described here may employ in vivo assays, although they may be configured for in vitro use. In vivo assays generally involve exposing a cell comprising TAZ to the candidate molecule. In in vitro assays, TAZ is exposed to the candidate molecule, optionally in the presence of other components, such as crude or semi-purified cell extract, or purified proteins. Where in vitro assays are conducted, these may employ arrays of candidate molecules (for example, an arrayed library). In vivo assays may be employed. Therefore, the TAZ polypeptide may be comprised in a cell, such as heterologously. Such a cell may be a transgenic cell, which has been engineered to express TAZ as described above.

Where an extract is employed, it may comprise a cytoplasmic extract or a nuclear extract, methods of preparation of which are well known in the art.

It will be appreciated that any component of a cell comprising TAZ may be employed, such as an organelle. One embodiment utilises a cytoplasmic or nuclear preparation, e.g., comprising a cell nucleus which comprises TAZ as described. The nuclear preparation may comprise one or more nuclei, which may be permeabilized or semi-permeabilized, by detergent treatment, for example.

Thus, in a specific embodiment, an assay format may include the following: a multiwell microtitre plate is set up to include one or more cells expressing TAZ polypeptide in each well; individual candidate molecules, or pools of candidate molecules, derived for example from a library, may be added to individual wells and modulation of TAZ activity measured. Where pools are used, these may be subdivided in to further pools and tested in the same manner. TAZ activity, for example binding activity or transcriptional co-activation activity, as described elsewhere in this document may then be assayed.

Alternatively or in addition to the assay methods described above, "subtractive" procedures may also be used to identify modulators or antagonists of TAZ. Under such "subtractive" procedures, a plurality of molecules is provided, which comprises one or more candidate molecules capable of functioning as a modulator (e.g., cell extract, nuclear extract, library of molecules, etc), and one or more components is removed, depleted or subtracted from the plurality of molecules. The "subtracted" extract, etc, is then assayed for activity, by exposure to a cell comprising TAZ (or a component thereof) as described.

Thus, for example, an 'immunodepletion' assay may be conducted to identify such modulators as follows. A cytoplasmic or nuclear extract may be prepared from a cell. The extract may be depleted or fractionated to remove putative modulators, such as by use of immunodepletion with appropriate antibodies. If the extract is depleted of a modulator, it will lose the ability to affect TAZ function or activity or expression. A series of subtractions and/or depletions may be required to identify the modulators or antagonists.

It will also be appreciated that the above "depletion" or "subtraction" assay may be used as a preliminary step to identify putative modulatory factors for further screening. Furthermore, or alternatively, the "depletion" or "subtraction" assay may be used to confirm the modulatory activity of a molecule identified by other means (for example, a "positive" screen as described elsewhere in this document) as a putative modulator.

Candidate molecules subjected to the assay and which are found to be of interest may be isolated and further studied. Methods of isolation of molecules of interest will depend on the type of molecule employed, whether it is in the form of a library, how many candidate molecules are being tested at any one time, whether a batch procedure is being followed, etc.

The candidate molecules may be provided in the form of a library. In one embodiment, more than one candidate molecule may be screened simultaneously. A library of candidate molecules may be generated, for example, a small molecule library, a polypeptide library, a nucleic acid library, a library of compounds (such as a combinatorial library), a library of antisense molecules such as antisense DNA or antisense RNA, an antibody library etc, by means known in the art. Such libraries are suitable for high-throughput screening. Different cells comprising TAZ may be exposed to individual members of the library, and effect on the TAZ activity determined. Array technology may be employed for this purpose. The cells may be spatially separated, for example, in wells of a microtitre plate.

In an embodiment, a small molecule library is employed. By a "small molecule", we refer to a molecule whose molecular weight may be less than about 50 kDa. In particular embodiments, a small molecule may have a molecular weight which is less than about 30 kDa, such as less than about 15 kDa or less than 10 kDa or so. Libraries of such small molecules, here referred to as "small molecule libraries" may contain polypeptides, small peptides, for example, peptides of 20 amino acids or fewer, for example, 15, 10 or 5 amino acids, simple compounds, etc.

Alternatively or in addition, a combinatorial library, as described in further detail below, may be screened for modulators or antagonists of TAZ. Assays for TAZ activity are described above.

Libraries

Libraries of candidate molecules, such as libraries of polypeptides or nucleic acids, may be employed in the screens for TAZ antagonists and inhibitors described here. Such libraries are exposed to TAZ protein, and their effect, if any, on the activity of the protein determined.

Selection protocols for isolating desired members of large libraries are known in the art, as typified by phage display techniques. Such systems, in which diverse peptide sequences are displayed on the surface of filamentous bacteriophage (Scott and Smith (1990 supra), have proven useful for creating libraries of antibody fragments (and the nucleotide sequences that encoding them) for the in vitro selection and amplification of specific antibody fragments that bind a target antigen. The nucleotide sequences encoding the $V_H$ and $V_L$ regions are linked to gene fragments which encode leader signals that direct them to the periplasmic space of E. coli and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al. (1990) supra; Kang et al. (1991) Proc. Natl. Acad. Sci. U.S.A., 88: 4363; Clackson et al. (1991) Nature, 352: 624; Lowman et al. (1991) Biochemistry, 30: 10832; Burton et al. (1991) Proc. Natl. Acad. Sci. U.S.A., 88: 10134; Hoogenboom et al. (1991) Nucleic Acids Res., 19: 4133; Chang et al. (1991) J. Immunol., 147: 3610; Breitling et al. (1991) Gene, 104: 147; Marks et al. (1991) supra; Barbas et al. (1992) supra; Hawkins and Winter (1992) J. Immunol., 22: 867; Marks et al., 1992, J. Biol. Chem., 267: 16007; Lerner et al. (1992) Science, 258: 1313, incorporated herein by reference). Such techniques may be modified if necessary for the expression generally of polypeptide libraries.

One particularly advantageous approach has been the use of scFv phage-libraries (Bird, R. E., et al. (1988) Science 242: 423-6, Huston et al., 1988, Proc. Natl. Acad. Sci. U.S.A., 85: 5879-5883; Chaudhary et al. (1990) Proc. Natl. Acad. Sci. U.S.A., 87: 1066-1070; McCafferty et al. (1990) supra; Clackson et al. (1991) supra; Marks et al. (1991) supra; Chiswell et al. (1992) Trends Biotech., 10: 80; Marks et al. (1992) supra). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys, supra), which are incorporated herein by reference.

Alternative library selection technologies include bacteriophage lambda expression systems, which may be screened directly as bacteriophage plaques or as colonies of lysogens, both as previously described (Huse et al. (1989) Science, 246: 1275; Caton and Koprowski (1990) Proc. Natl. Acad. Sci. U.S.A., 87; Mullinax et al. (1990) Proc. Natl. Acad. Sci. U.S.A., 87: 8095; Persson et al. (1991) Proc. Natl. Acad. Sci. U.S.A., 88: 2432) and are of use in the methods and compositions described here. These expression systems may be used to screen a large number of different members of a library, in the order of about $10^6$ or even more. Other screening systems rely, for example, on direct chemical synthesis of library members. One early method involves the synthesis of peptides on a set of pins or rods, such as described in WO84/03564. A similar method involving peptide synthesis on beads, which forms a peptide library in which each bead is an individual library member, is described in U.S. Pat. No. 4,631,211 and a related method is described in WO92/00091. A significant improvement of the bead-based methods involves tagging each bead with a unique identifier tag, such as an oligonucleotide, so as to facilitate identification of the amino acid sequence of each library member. These improved bead-based methods are described in WO93/06121.

Another chemical synthesis method involves the synthesis of arrays of peptides (or peptidomimetics) on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a receptor) and reactive library members occur is determined, thereby identifying the sequences of the reactive library members on the basis of spatial location. These methods are described in U.S. Pat. No. 5,143,854; WO90/15070 and WO92/10092; Fodor et al. (1991) Science, 251: 767; Dower and Fodor (1991) Ann. Rep. Med. Chem., 26: 271.

Other systems for generating libraries of polypeptides or nucleotides involve the use of cell-free enzymatic machinery for the in vitro synthesis of the library members. In one method, RNA molecules are selected by alternate rounds of selection against a target ligand and PCR amplification (Tuerk and Gold (1990) Science, 249: 505; Ellington and Szostak (1990) Nature, 346: 818). A similar technique may be used to identify DNA sequences which bind a predetermined human transcription factor (Thiesen and Bach (1990) Nucleic Acids Res., 18: 3203; Beaudry and Joyce (1992) Science, 257: 635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection. These and all the foregoing documents also are incorporated herein by reference.

The library may in particular comprise a library of zinc fingers; zinc fingers are known in the art and act as transcription factors. Suitable zinc finger libraries are disclosed in, for example, WO 96/06166 and WO 98/53057. Construction of zinc finger libraries may utilise rules for determining interaction with specific DNA sequences, as disclosed in for example WO 98/53058 and WO 98/53060. Zinc fingers capable of interacting specifically with methylated DNA are disclosed in WO 99/47656. The above zinc finger libraries may be immobilised in the form of an array, for example as disclosed in WO 01/25417.

Combinatorial Libraries

Libraries, in particular, libraries of candidate molecules, may suitably be in the form of combinatorial libraries (also known as combinatorial chemical libraries).

A "combinatorial library", as the term is used in this document, is a collection of multiple species of chemical compounds that consist of randomly selected subunits. Combinatorial libraries may be screened for molecules which are capable of inhibiting TAZ.

Various combinatorial libraries of chemical compounds are currently available, including libraries active against proteolytic and non-proteolytic enzymes, libraries of agonists and antagonists of G-protein coupled receptors (GPCRs), libraries active against non-GPCR targets (e.g., integrins, ion channels, domain interactions, nuclear receptors, and transcription factors) and libraries of whole-cell oncology and anti-infective targets, among others. A comprehensive review of combinatorial libraries, in particular their construction and uses is provided in Dolle and Nelson (1999), *Journal of Combinatorial Chemistry*, Vol 1 No 4, 235-282. Reference is also made to *Combinatorial peptide library protocols* (edited by Shmuel Cabilly, Totowa, N.J.: Humana Press, c1998. *Methods in Molecular Biology* v. 87). Specific combinatorial libraries and methods for their construction are disclosed in U.S. Pat. No. 6,168,914 (Campbell, et al), as well as in Baldwin et al. (1995), "Synthesis of a Small Molecule Library Encoded with Molecular Tags," J. Am. Chem. Soc. 117:5588-5589, and in the references mentioned in those documents.

In one embodiment, the combinatorial library which is screened is one which is designed to potentially include molecules which interact with a component of the cell to influence gene expression. For example, combinatorial libraries against chromatin structural proteins may be screened. Other libraries which are useful for this embodiment include combinatorial libraries against histone modification enzymes (e.g., histone acetylation or histone methylation enzymes), or DNA modification, for example, DNA methylation or demethylation.

Further references describing chemical combinatorial libraries, their production and use include those available from the URL http://www.netsci.org/Science/Combichem/, including The Chemical Generation of Molecular Diversity. Michael R. Pavia, Sphinx Pharmaceuticals, A Division of Eli Lilly (Published July, 1995); Combinatorial Chemistry: A Strategy for the Future—MDL Information Systems discusses the role its Project Library plays in managing diversity libraries (Published July, 1995); Solid Support Combinatorial Chemistry in Lead Discovery and SAR Optimization, Adnan M. M. Mjalli and Barry E. Toyonaga, Ontogen Corporation (Published July, 1995); Non-Peptidic Bradykinin Receptor Antagonists From a Structurally Directed Non-Peptide Library. Sarvajit Chakravarty, Babu J. Mavunkel, Robin Andy, Donald J. Kyle*, Scios Nova Inc. (Published July, 1995); Combinatorial Chemistry Library Design using Pharmacophore Diversity Keith Davies and Clive Briant, Chemical Design Ltd. (Published July, 1995); A Database System for Combinatorial Synthesis Experiments—Craig James and David Weininger, Daylight Chemical Information Systems, Inc. (Published July, 1995); An Information Management Architecture for Combinatorial Chemistry, Keith Davies and Catherine White, Chemical Design Ltd. (Published July, 1995); Novel Software Tools for Addressing Chemical Diversity, R. S. Pearlman, Laboratory for Molecular Graphics and Theoretical Modeling, College of Pharmacy, University of Texas (Published June/July, 1996); Opportunities for Computational Chemists Afforded by the New Strategies in Drug Discovery: An Opinion, Yvonne Connolly Martin, Computer Assisted Molecular Design Project, Abbott Laboratories (Published June/July, 1996); Combinatorial Chemistry and Molecular Diversity Course at the University of Louisville: A Description, Arno F. Spatola, Department of Chemistry, University of Louisville (Published June/July, 1996); Chemically Generated Screening Libraries Present and Future. Michael R. Pavia, Sphinx Pharmaceuticals, A Division of Eli Lilly (Published June/July, 1996); Chemical Strategies For Introducing Carbohydrate Molecular Diversity Into The Drug Discovery Process. Michael J. Sofia, Transcell Technologies Inc. (Published June/July, 1996); Data Management for Combinatorial Chemistry. Maryjo Zaborowski, Chiron Corporation and Sheila H. DeWitt, Parke-Davis Pharmaceutical Research, Division of Warner-Lambert Company (Published November, 1995); and The Impact of High Throughput Organic Synthesis on R&D in Bio-Based Industries, John P. Devlin (Published March, 1996).

Techniques in combinatorial chemistry are gaining wide acceptance among modern methods for the generation of new pharmaceutical leads (Gallop, M. A. et al., 1994, J. Med. Chem. 37:1233-1251; Gordon, E. M. et al., 1994, J. Med. Chem. 37:1385-1401.). One combinatorial approach in use is based on a strategy involving the synthesis of libraries containing a different structure on each particle of the solid phase support, interaction of the library with a soluble receptor, identification of the 'bead' which interacts with the macromolecular target, and determination of the structure carried by the identified 'bead' (Lam, K. S. et al., 1991, Nature 354:82-84). An alternative to this approach is the sequential release of defined aliquots of the compounds from the solid support, with subsequent determination of activity in solution, identification of the particle from which the active compound was released, and elucidation of its structure by direct sequencing (Salmon, S. E. et al., 1993, Proc. Natl. Acad. Sci. USA 90:11708-11712), or by reading its code (Kerr, J. M. et al., 1993, J. Am. Chem. Soc. 115:2529-2531; Nikolaiev, V. et al., 1993, Pept. Res. 6:161-170; Ohlmeyer, M. H. J. et al., 1993, Proc. Natl. Acad. Sci. USA 90:10922-10926).

Soluble random combinatorial libraries may be synthesized using a simple principle for the generation of equimolar mixtures of peptides which was first described by Furka (Furka, A. et al., 1988, Xth International Symposium on Medicinal Chemistry, Budapest 1988; Furka, A. et al., 1988, 14th International Congress of Biochemistry, Prague 1988; Furka, A. et al., 1991, Int. J. Peptide Protein Res. 37:487-493). The construction of soluble libraries for iterative screening has also been described (Houghten, R. A. et al. 1991, Nature 354:84-86). K. S. Lam disclosed the novel and unexpectedly powerful technique of using insoluble random combinatorial libraries. Lam synthesized random combinatorial libraries on solid phase supports, so that each support had a test compound of uniform molecular structure, and screened the libraries without prior removal of the test compounds from the support by solid phase binding protocols (Lam, K. S. et al., 1991, Nature 354:82-84).

Thus, a library of candidate molecules may be a synthetic combinatorial library (e.g., a combinatorial chemical library), a cellular extract, a bodily fluid (e.g., urine, blood, tears, sweat, or saliva), or other mixture of synthetic or natural products (e.g., a library of small molecules or a fermentation mixture).

A library of molecules may include, for example, amino acids, oligopeptides, polypeptides, proteins, or fragments of peptides or proteins; nucleic acids (e.g., antisense; DNA; RNA; or peptide nucleic acids, PNA); aptamers; or carbohydrates or polysaccharides. Each member of the library can be singular or can be a part of a mixture (e.g., a compressed library). The library may contain purified compounds or can be "dirty" (i.e., containing a significant quantity of impurities).

Commercially available libraries (e.g., from Affymetrix, ArQule, Neose Technologies, Sarco, Ciddco, Oxford Asymmetry, Maybridge, Aldrich, Panlabs, Pharmacopoeia, Sigma, or Tripose) may also be used with the methods described here.

In addition to libraries as described above, special libraries called diversity files can be used to assess the specificity, reliability, or reproducibility of the new methods. Diversity files contain a large number of compounds (e.g., 1000 or more small molecules) representative of many classes of compounds that could potentially result in nonspecific detection in an assay. Diversity files are commercially available or can also be assembled from individual compounds commercially available from the vendors listed above.

Anti-TAZ Antibodies

Anti-TAZ agents, including antagonists or modulators of TAZ, which may be used to regulate the activity of this protein (for example, for methods of treating or preventing diseases such as cancer as described in this document) may include antibodies against the TAZ protein.

We therefore provide for antibodies which bind to a TAZ polypeptide, fragment, homologue, variant or derivative thereof. Such antibodies are useful in detecting TAZ expression, and in particular in diagnosing a TAZ associated disease such as breast cancer. Other antibodies include those which have therapeutic activity, i.e., which are may be used in a therapeutic manner to treat, manage or prevent any TAZ associated disease, including breast cancer.

Examples of antibodies capable of binding to TAZ include rabbit anti-TAZ antibody against amino acids 160-229 of TAZ, rabbit anti-TAZ antibody (catalogue number 2149S, Cell Signaling Technology, Danvers, Mass., USA), rabbit polyclonal anti-TAZ antibody (catalogue number NB110-58359SS, Novus Biological, Littleton, Colo., USA), Mouse Monoclonal anti-TAZ [1B10] (catalogue number H00006901-M12, Novus Biological, Littleton, Colo., USA), Rabbit anti-Human TAZ Polyclonal Antibody (catalogue number LS-B94, LifeSpan Biosciences, Inc., Seattle, Wash., USA) or p-TAZ (Ser 89)-R (catalogue number sc-17610-R, Santa Cruz Biotechnology, Santa Cruz, Calif., USA).

Furthermore, antibodies which are specific for TAZ may be generated against any suitable epitope, for example, an epitope derived from the TAZ protein. The sequence of a suitable fragment of TAZ may comprise residues 160-229 of TAZ and any epitope from this sequence may be used for the generation of specific TAZ antibodies.

For the purposes of this document, the term "antibody" refers to complete antibodies or antibody fragments capable of binding to a selected target. Unless specified to the contrary, the term includes but is not limited to, polyclonal, monoclonal, natural or engineered antibodies including chimeric, CDR-grafted and humanised antibodies, and artificially selected antibodies produced using phage display or alternative techniques. The term also includes single chain, Fab fragments and fragments produced by a Fab expression library. Such fragments include fragments of whole antibodies which retain their binding activity for a target substance, Fv, F(ab') and F(ab')2 fragments, as well as single chain antibodies (scFv), fusion proteins and other synthetic proteins which comprise the antigen-binding site of the antibody. Small fragments, such as Fv and ScFv, possess advantageous properties for diagnostic and therapeutic applications on account of their small size and consequent superior tissue distribution.

The antibodies and fragments thereof may be humanised antibodies, for example as described in EP-A-239400. Furthermore, antibodies with fully human variable regions (or their fragments), for example, as described in U.S. Pat. Nos. 5,545,807 and 6,075,181 may also be used. Neutralizing antibodies, i.e., those which inhibit any biological activity of TAZ, may be used for diagnostics and therapeutics.

The antibodies described here may be altered antibodies comprising an effector protein such as a label. Labels which allow the imaging of the distribution of the antibody in vivo or in vitro may be used. Such labels may be radioactive labels or radioopaque labels, such as metal particles, which are readily visualisable within an embryo or a cell mass. Moreover, they may be fluorescent labels or other labels which are visualisable on tissue samples.

Antibodies may be produced by standard techniques, such as by immunisation or by using a phage display library. Such an antibody may be capable of binding specifically to the TAZ protein or homologue, fragment, etc.

Polyclonal Antibodies

If polyclonal antibodies are desired, a selected mammal (e.g., mouse, rabbit, goat, horse, etc.) may be immunised with an immunogenic composition comprising a TAZ polypeptide or peptide. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (Bacilli Calmette-Guerin) and *Corynebacterium parvum* are potentially useful human adjuvants which may be employed if purified the substance amino acid sequence is administered to immunologically compromised individuals for the purpose of stimulating systemic defense.

Serum from the immunised animal is collected and treated according to known procedures. If serum containing polyclonal antibodies to an epitope obtainable from a TAZ polypeptide contains antibodies to other antigens, the polyclonal antibodies can be purified by immunoaffinity chromatography. Techniques for producing and processing polyclonal antisera are known in the art. In order that such antibodies may be made, we also provide TAZ amino acid sequences or fragments thereof haptenised to another amino acid sequence for use as immunogens in animals or humans.

Monoclonal Antibodies

Monoclonal antibodies directed against epitopes obtainable from a TAZ polypeptide or peptide can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against orbit epitopes can be screened for various properties; i.e., for isotype and epitope affinity.

Monoclonal antibodies may be prepared using any technique which provides for the production of antibody molecules by continuous cell lines in culture. These include, but are not limited to, the hybridoma technique originally described by Koehler and Milstein (1975 Nature 256:495-497), the trioma technique, the human B-cell hybridoma technique (Kosbor et al (1983) Immunol Today 4:72; Cote et al (1983) Proc Natl Acad Sci 80:2026-2030) and the EBV-hybridoma technique (Cole et al., *Monoclonal Antibodies and Cancer Therapy*, pp. 77-96, Alan R. Liss, Inc., 1985).

Recombinant DNA technology may be used to improve the antibodies as described here. Thus, chimeric antibodies may be constructed in order to decrease the immunogenicity thereof in diagnostic or therapeutic applications. Such techniques comprise splicing of mouse antibody genes to human antibody genes to obtain a molecule with appropriate antigen specificity and biological activity (Morrison et al (1984) Proc Natl Acad Sci 81:6851-6855; Neuberger et al (1984) Nature 312:604-608; Takeda et al (1985) Nature 314:452-454). Moreover, immunogenicity may be minimised by humanizing the antibodies by CDR grafting [see European Patent Application 0 239 400 (Winter)] and, optionally, framework modification [EP 0 239 400].

Alternatively, techniques described for the production of single chain antibodies (U.S. Pat. No. 4,946,779) can be adapted to produce the substance specific single chain antibodies.

Antibodies, both monoclonal and polyclonal, which are directed against epitopes obtainable from a TAZ polypeptide or peptide are particularly useful in diagnosis. Monoclonal antibodies, in particular, may be used to raise anti-idiotype antibodies. Anti-idiotype antibodies are immunoglobulins which carry an "internal image" of the substance and/or agent against which protection is desired. Techniques for raising anti-idiotype antibodies are known in the art. These anti-idiotype antibodies may also be useful in therapy.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833-3837), and Winter G and Milstein C (1991; Nature 349:293-299).

Antibody fragments which contain specific binding sites for the polypeptide or peptide may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W D et al (1989) Science 256:1275-128 1).

Techniques for the production of single chain antibodies (U.S. Pat. No. 4,946,778) can also be adapted to produce single chain antibodies to TAZ polypeptides. Also, transgenic mice, or other organisms including other mammals, may be used to express humanized antibodies.

The above-described antibodies may be employed to isolate or to identify clones expressing the polypeptide or to purify the polypeptides by affinity chromatography.

Recombinant Techniques of Antibody Production

Recombinant DNA technology may be used to produce the antibodies according to established procedure, in bacterial or mammalian cell culture. The selected cell culture system may secrete the antibody product.

Therefore, we disclose a process for the production of an antibody comprising culturing a host, e.g. *E. coli* or a mammalian cell, which has been transformed with a hybrid vector comprising an expression cassette comprising a promoter operably linked to a first DNA sequence encoding a signal peptide linked in the proper reading frame to a second DNA sequence encoding said antibody protein, and isolating said protein.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2xYT, or M9 Minimal Medium, and for yeast in medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, incorporated herein by reference. Techniques for the preparation of recombinant antibody molecules are described in the above references and also in, for example, EP 0623679; EP 0368684 and EP 0436597, which are incorporated herein by reference.

The cell culture supernatants are screened for the desired antibodies, preferentially by immunofluorescent staining of PGCs or other pluripotent cells, such as ES or EG cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with the antigen, or fragments thereof, or with Protein-A.

Hybridoma cells secreting the monoclonal antibodies are also provided. Hybridoma cells may be genetically stable, secrete monoclonal antibodies of the desired specificity and can be activated from deep-frozen cultures by thawing and recloning.

Also included is a process for the preparation of a hybridoma cell line secreting monoclonal antibodies directed to the TAZ polypeptide, characterised in that a suitable mammal, for example a Balb/c mouse, is immunised with a one or more TAZ polypeptides, or antigenic fragments thereof; antibody-producing cells of the immunised mammal are fused with cells of a suitable myeloma cell line, the hybrid cells obtained in the fusion are cloned, and cell clones secreting the desired antibodies are selected. For example spleen cells of Balb/c mice immunised with TAZ are fused with cells of the myeloma cell line PAI or the myeloma cell line Sp2/0-Ag14, the obtained hybrid cells are screened for secretion of the desired antibodies, and positive hybridoma cells are cloned.

We describe a process for the preparation of a hybridoma cell line, characterised in that Balb/c mice are immunised by injecting subcutaneously and/or intraperitoneally between 10 and $10^7$ and $10^8$ cells expressing TAZ and a suitable adjuvant several times, e.g. four to six times, over several months, e.g. between two and four months, and spleen cells from the immunised mice are taken two to four days after the last injection and fused with cells of the myeloma cell line PAI in the presence of a fusion promoter, such as polyethylene glycol. The myeloma cells may be fused with a three to twenty-fold excess of spleen cells from the immunised mice in a solution containing about 30% to about 50% polyethylene glycol of a molecular weight around 4000. After the fusion the cells are expanded in suitable culture media as described hereinbefore, supplemented with a selection medium, for example HAT medium, at regular intervals in order to prevent normal myeloma cells from overgrowing the desired hybridoma cells.

Recombinant DNAs comprising an insert coding for a heavy chain variable domain and/or for a light chain variable domain of antibodies directed to TAZ as described hereinbefore are also disclosed. By definition such DNAs comprise coding single stranded DNAs, double stranded DNAs consisting of said coding DNAs and of complementary DNAs thereto, or these complementary (single stranded) DNAs themselves.

Furthermore, DNA encoding a heavy chain variable domain and/or for a light chain variable domain of antibodies directed to TAZ can be enzymatically or chemically synthesised DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted or exchanged with one or more other amino acids. The modification(s) may be outside the CDRs of the heavy chain variable domain and/or of the light chain variable domain of the antibody. Such a mutant DNA is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Also disclosed are recombinant DNAs comprising an insert coding for a heavy chain murine variable domain of an antibody directed to TAZ fused to a human constant domain g, for example γ1, γ2, γ3 or γ4, such as γ1 or γ4 Likewise recombinant DNAs comprising an insert coding for a light chain murine variable domain of an antibody directed to TAZ fused to a human constant domain κ or λ, such as κ are also disclosed.

In another embodiment, we disclose recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule.

The DNA coding for an effector molecule is intended to be a DNA coding for the effector molecules useful in diagnostic or therapeutic applications. Thus, effector molecules which are toxins or enzymes, especially enzymes capable of catalysing the activation of prodrugs, are particularly indicated. The DNA encoding such an effector molecule has the sequence of a naturally occurring enzyme or toxin encoding DNA, or a mutant thereof, and can be prepared by methods well known in the art.

Use

Anti-TAZ antibodies may be used in method of detecting a TAZ polypeptide present in biological samples by a method which comprises: (a) providing an anti-TAZ antibody; (b) incubating a biological sample with said antibody under conditions which allow for the formation of an antibody-antigen complex; and (c) determining whether antibody-antigen complex comprising said antibody is formed.

Suitable samples include extracts tissues such as brain, breast, ovary, lung, colon, pancreas, testes, liver, muscle and bone tissues or from neoplastic growths derived from such tissues. In particular, a sample may comprise a breast tissue, such as a breast tissue from an individual suspected to be suffering from breast cancer.

Antibodies may be bound to a solid support and/or packaged into kits in a suitable container along with suitable reagents, controls, instructions and the like.

Antibody Delivery

The antibodies against the TAZ protein may be delivered into a cell by means of techniques known in the art, for example by the use of liposomes, polymers, (e.g., polyethylene glycol (PEG), N-(2-hydroxypropyl) methacrylamide (HPMA) copolymers, polyamidoamine (PAMAM) dendrimers, HEMA, linear polyamidoamine polymers etc) etc. The immunoglobulins and/or antibodies may also be delivered into cells as protein fusions or conjugates with a protein capable of crossing the plasma membrane and/or the nuclear membrane. For example, the immunoglobulin and/or target may be fused or conjugated to a domain or sequence from such a protein responsible for the translocational activity. Translocation domains and sequences may include domains and sequences from the HIV-1-trans-activating protein (Tat), *Drosophila* Antennapedia homeodomain protein and the herpes simplex-1 virus VP22 protein.

Pharmaceutical Compositions and Administration

While it is possible for the anti-TAZ agent, including an TAZ nucleic acid, polypeptide, fragment, homologue, variant or derivative thereof, modulator, agonist or antagonist, a structurally related compound, or an acidic salt of either to be administered alone, the active ingredient may be formulated as a pharmaceutical formulation.

We therefore also disclose pharmaceutical compositions comprising an anti-TAZ agent. Such pharmaceutical compositions are useful for delivery of the anti-TAZ agent such as in the form of a composition as described, to an individual for the treatment or alleviation of symptoms as described.

A pharmaceutical composition in the context of the present document is a composition of matter comprising at least an anti-TAZ agent as an active ingredient.

The pharmaceutical formulations comprise an effective amount of the anti-TAZ agent together with one or more pharmaceutically-acceptable carriers. An "effective amount" is the amount sufficient to alleviate at least one symptom of a disease as described.

The effective amount will vary depending upon the particular disease or syndrome to be treated or alleviated, as well as other factors including the age and weight of the patient, how advanced the disease etc state is, the general health of the patient, the severity of the symptoms, and whether the anti-TAZ agent is being administered alone or in combination with other therapies.

Suitable pharmaceutically acceptable carriers are well known in the art and vary with the desired form and mode of administration of the pharmaceutical formulation. For example, they can include diluents or excipients such as fillers, binders, wetting agents, disintegrators, surface-active agents, lubricants and the like. Typically, the carrier is a solid, a liquid or a vaporizable carrier, or a combination thereof. Each carrier should be "acceptable" in the sense of being compatible with the other ingredients in the formulation and not injurious to the patient. The carrier should be biologically acceptable without eliciting an adverse reaction (e.g. immune response) when administered to the host.

The active ingredient(s) of a pharmaceutical composition is contemplated to exhibit therapeutic activity, for example, in the alleviation of cancer, tumours, neoplasms and other related diseases. Dosage regimes may be adjusted to provide the optimum therapeutic response. For example, several divided doses may be administered daily or the dose may be proportionally reduced as indicated by the exigencies of the therapeutic situation.

The active compound may be administered in a convenient manner such as by the oral, intravenous (where water soluble), intramuscular, subcutaneous, intranasal, intradermal or suppository routes or implanting (e.g. using slow release molecules). Depending on the route of administration, the active ingredient may be required to be coated in a material to protect said ingredients from the action of enzymes, acids and other natural conditions which may inactivate said ingredient.

The anti-TAZ agent may be administered alone, or in combination with other therapeutic agents. Other therapeutic agents suitable for use herein are any compatible drugs that are effective for the intended purpose, or drugs that are complementary to the agent formulation. The formulation utilized in a combination therapy may be administered simultaneously, or sequentially with other treatment, such that a combined effect is achieved.

Oral Administration

In some embodiments, the inhibitor of TAZ activity, expression or amount is provided as an oral composition and administered accordingly. The dosage of the inhibitor of TAZ activity, expression or amount may be between about 1 mg/day to about 10 mg/day.

The pharmaceutical composition can be administered in an oral formulation in the form of tablets, capsules or solutions. An effective amount of the oral formulation is administered to patients 1 to 3 times daily until the symptoms of the disease alleviated.

The effective amount of agent depends on the age, weight and condition of a patient. In general, the daily oral dose of agent is less than 1200 mg, and more than 100 mg. The daily oral dose may be about 300-600 mg. Oral formulations are conveniently presented in a unit dosage form and may be prepared by any method known in the art of pharmacy. The composition may be formulated together with a suitable pharmaceutically acceptable carrier into any desired dosage form. Typical unit dosage forms include tablets, pills, powders, solutions, suspensions, emulsions, granules, capsules, suppositories. In general, the formulations are prepared by uniformly and intimately bringing into association the agent composition with liquid carriers or finely divided solid carriers or both, and as necessary, shaping the product. The active ingredient can be incorporated into a variety of basic materials in the form of a liquid, powder, tablets or capsules to give an effective amount of active ingredient to treat the disease.

The composition may be suitably orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. The amount of active compound in such therapeutically useful compositions in such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

Injectable or Intravenous Administration

In some embodiments, the anti-TAZ agent is provided as an injectable or intravenenous composition and administered accordingly. The dosage of the anti-TAZ agent inhibitor may be between about 5 mg/kg/2 weeks to about 10 mg/kg/2 weeks. The anti-TAZ agent inhibitor may be provided in a dosage of between 10-300 mg/day, such as at least 30 mg/day, less than 200 mg/day or between 30 mg/day to 200 mg/day.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene gloycol, and the like), suitable mixtures thereof, and vegetable oils. The proper fluidity can be maintained, for example, by the use of a coating such as lecithin, by the maintenance of the required particle size in the case of dispersion and by the use of superfactants.

Topical Administration

The pharmaceutical compositions disclosed here include those suitable for topical and oral administration, with topical formulations being preferred where the tissue affected is primarily the skin or epidermis (for example, psoriasis, eczema and other epidermal diseases).

The topical formulations include those pharmaceutical forms in which the composition is applied externally by direct contact with the skin surface to be treated. A conventional pharmaceutical form for topical application includes a soak, an ointment, a cream, a lotion, a paste, a gel, a stick, a spray, an aerosol, a bath oil, a solution and the like. Topical therapy is delivered by various vehicles, the choice of vehicle can be important and generally is related to whether an acute or chronic disease is to be treated. As an example, an acute skin proliferation disease generally is treated with aqueous drying preparations, whereas chronic skin proliferation disease is treated with hydrating preparations. Soaks are the easiest method of drying acute moist eruptions. Lotions (powder in water suspension) and solutions (medications dissolved in a solvent) are ideal for hairy and intertriginous areas. Ointments or water-in-oil emulsions, are the most effective hydrating agents, appropriate for dry scaly eruptions, but are greasy and depending upon the site of the lesion sometimes undesirable. As appropriate, they can be applied in combination with a bandage, particularly when it is desirable to increase penetration of the agent composition into a lesion. Creams or oil-in-water emulsions and gels are absorbable and are the most cosmetically acceptable to the patient. (Guzzo et al, in Goodman & Gilman's Pharmacological Basis of Therapeutics, 9th Ed., p. 1593-15950 (1996)). Cream formulations generally include components such as petroleum, lanolin, polyethylene glycols, mineral oil, glycerin, isopropyl palmitate, glyceryl stearate, cetearyl alcohol, tocopheryl acetate, isopropyl myristate, lanolin alcohol, simethicone, carbomen, methylchlorisothiazolinone, methylisothiazolinone, cyclomethicone and hydroxypropyl methylcellulose, as well as mixtures thereof.

Other formulations for topical application include shampoos, soaps, shake lotions, and the like, particularly those formulated to leave a residue on the underlying skin, such as the scalp (Arndt et al, in Dermatology In General Medicine 2:2838 (1993)).

In general, the concentration of the composition in the topical formulation is in an amount of about 0.5 to 50% by weight of the composition, such as about 1 to 30%, about 2-20%, or about 5-10%. The concentration used can be in the upper portion of the range initially, as treatment continues, the concentration can be lowered or the application of the formulation may be less frequent. Topical applications are often applied twice daily. However, once-daily application of a larger dose or more frequent applications of a smaller dose may be effective. The stratum corneum may act as a reservoir and allow gradual penetration of a drug into the viable skin layers over a prolonged period of time.

In a topical application, a sufficient amount of active ingredient must penetrate a patient's skin in order to obtain a desired pharmacological effect. It is generally understood that the absorption of drug into the skin is a function of the nature of the drug, the behaviour of the vehicle, and the skin. Three major variables account for differences in the rate of absorption or flux of different topical drugs or the same drug in different vehicles; the concentration of drug in the vehicle, the partition coefficient of drug between the stratum corneum and the vehicle and the diffusion coefficient of drug in the stratum corneum. To be effective for treatment, a drug must cross the stratum corneum which is responsible for the barrier function of the skin. In general, a topical formulation which exerts a high in vitro skin penetration is effective in vivo. Ostrenga et al (J. Pharm. Sci., 60:1175-1179 (1971)) demonstrated that in vivo efficacy of topically applied steroids was proportional to the steroid penetration rate into dermatomed human skin in vitro.

A skin penetration enhancer which is dermatologically acceptable and compatible with the agent can be incorporated into the formulation to increase the penetration of the active compound(s) from the skin surface into epidermal keratinocytes. A skin enhancer which increases the absorption of the active compound(s) into the skin reduces the amount of agent needed for an effective treatment and provides for a longer lasting effect of the formulation. Skin penetration enhancers are well known in the art. For example, dimethyl sulfoxide (U.S. Pat. No. 3,711,602); oleic acid, 1,2-butanediol surfactant (Cooper, J. Pharm. Sci., 73:1153-1156 (1984)); a combination of ethanol and oleic acid or oleyl alcohol (EP 267,617), 2-ethyl-1,3-hexanediol (WO 87/03490); decyl methyl sulphoxide and Azone® (Hadgraft, Eur. J. Drug. Metab. Pharmacokinet, 21:165-173 (1996)); alcohols, sulphoxides, fatty acids, esters, Azone®, pyrrolidones, urea and polyoles (Kalbitz et al, Pharmazie, 51:619-637 (1996));

Terpenes such as 1,8-cineole, menthone, limonene and nerolidol (Yamane, J. Pharmacy & Pharmocology, 47:978-989 (1995)); Azone® and Transcutol (Harrison et al, Pharmaceutical Res. 13:542-546 (1996)); and oleic acid, polyethylene glycol and propylene glycol (Singh et al, Pharmazie, 51:741-744 (1996)) are known to improve skin penetration of an active ingredient.

Levels of penetration of an agent or composition can be determined by techniques known to those of skill in the art. For example, radiolabeling of the active compound, followed by measurement of the amount of radiolabeled compound absorbed by the skin enables one of skill in the art to determine levels of the composition absorbed using any of several methods of determining skin penetration of the test compound. Publications relating to skin penetration studies include Reinfenrath, W G and G S Hawkins. The Weaning Yorkshire Pig as an Animal Model for Measuring Percutaneous Penetration. In:Swine in Biomedical Research (M. E. Tumbleson, Ed.) Plenum, New York, 1986, and Hawkins, G. S. Methodology for the Execution of In Vitro Skin Penetration Determinations. In: Methods for Skin Absorption, B W Kemppainen and W G Reifenrath, Eds., CRC Press, Boca Raton, 1990, pp. 67-80; and W. G. Reifenrath, Cosmetics & Toiletries, 110:3-9 (1995).

For some applications, a long acting form of agent or composition may be administered using formulations known in the arts, such as polymers. The agent can be incorporated into a dermal patch (Junginger, H. E., in Acta Pharmaceutica Nordica 4:117 (1992); Thacharodi et al, in Biomaterials 16:145-148 (1995); Niedner R., in Hautarzt 39:761-766 (1988)) or a bandage according to methods known in the arts, to increase the efficiency of delivery of the drug to the areas to be treated.

Optionally, the topical formulations described here can have additional excipients for example; preservatives such as methylparaben, benzyl alcohol, sorbic acid or quaternary ammonium compound; stabilizers such as EDTA, antioxidants such as butylated hydroxytoluene or butylated hydroxanisole, and buffers such as citrate and phosphate.

Parenteral Administration

The active compound may also be administered parenterally or intraperitoneally. Dispersions can also be prepared in glycerol, liquid polyethylene glycols, and mixtures thereof and in oils. In some embodiments, the dispersions may be prepared in 30% Capsitol (CyDex, Inc., Lenexa, Kans., USA). Capsitol is a polyanionic β-cyclodextrin derivative with a sodium sulfonate salt separated from the lipophilic cavity by a butyl ether spacer group, or sulfobutylether (SBE). The cyclodextrin may be SBE7-β-CD.

Adjuvants

The composition may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin. Liposomes include water-in-oil-in-water CGF emulsions as well as conventional liposomes.

Prevention of Microorganism Growth

Under ordinary conditions of storage and use, these preparations may contain a preservative to prevent the growth of microorganisms.

The prevention of the action of microorganisms can be brought about by various antibacterial and antifungal agents, for example, parabens, chlorobutanol, phenol, sorbic acid, thirmerosal, and the like. In many cases, it is possible to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilisation. Generally, dispersions are prepared by incorporating the sterilised active ingredient into a sterile vehicle which contains the basic dispersion medium and the required other ingredients from those enumerated above. In the case of sterile powders for the preparation of sterile injectable solutions, the methods of preparation may include vacuum drying and the freeze-drying technique which yield a powder of the active ingredient plus any additional desired ingredient from previously sterile-filtered solution thereof.

Pharmaceutically Acceptable Carrier

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

Dosage Unit Forms

It is especially advantageous to formulate pharmaceutical compositions in dosage unit form for ease of administration and uniformity of dosage.

Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the novel dosage unit forms are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired.

The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

EXAMPLES

Example 1

Cell Lines and Plasmids

The cell lines MCF10A, MCF7, MDA-MB-231, Hs578T, ZR-75-1 are purchased from American Type Culture Collection and maintained in the recommended media except for MCF10A cells, which are cultured in DMEM supplemented with 5% horse serum, 20 ng/ml of EGF, 0.5 μg/ml of hydrocortisone, 100 ng/ml of cholera toxin, 10 μg/ml of insulin and pen/strep. BT-549 cells are cultured in RPMI supplemented with 10% FBS. MDA-MB-435S, T-47D cells are from Lo Ting Ling (Institute of Molecular and Cell Biology) and maintained in DMEM supplemented with 10% FBS and 10 μg/ml of insulin. BT-20, MDA-MB-453 and BT-474 are provided by Yoshiaki Ito (Institute of Molecular and Cell Biology). BT-20 cells are maintained in MEM supplemented with 10% FBS. MDA-MB-453 cells are maintained in DMEM with 10% FBS supplemented with 10 μg/ml of insulin. The amphotropic *Phoenix* packaging cells are kindly provided by G. Nolan (Stanford University) and maintained in DMEM supplemented with 10% FBS.

The cDNAs of human TAZ is from MCG clone 19891. The full-length TAZ or Flag-tagged TAZ are constructed by polymerase chain reaction (PCR) using the MCG19891 clone and cloned into BamHI-SalI sites of the retroviral vector pBABEpuro. The Flag-tagged mouse TAZ is constructed by PCR using mouse cDNA library from Naiyang Fu (Institute of Molecular and Cell Biology) and cloned into SnaBI-SalI sites of the retroviral vector pBABEhygromycin from Sofie Van Huffel (Institute of Molecular and Cell Biology). pGEX-TAZ (amino acids 160-229) and pET-TAZ (amino acids 160-229) are constructed by cloning the PCR-amplified cDNA fragment encoding the indicated amino acids into EcoRI/XhoI sites of pGEX4T-1 (Amersham Biosciences) and pET32a (Novagen), respectively. pGEX-YAP (amino acids 206-262) is constructed by cloning the PCR-amplified fragment from human cDNA library into the EcoRI/SalI sites of pGEX4T-1.

Example 2

Purification of GST-tagged Protein

One liter of *E. coli* BL21 (DE3) carrying the pGEX-TAZ or pGEX-YAP constructs are grown in LB medium until OD 0.8-1 and are induced with 0.1 mM of IPTG (isopropyl-β-D-thiogalactopyranoside) for overnight at room temperature. Bacteria are harvested by centrifugation and lysed by sonication in phosphate-buffered saline (PBS). The lysate are spun at 10,000 g for 30 min at 4° C. and the supernatant is mixed with 0.5 ml of glutathione-sepharose 4B (Amersham Biosciences) for 2 h at 4° C. The beads are washed four times with PBS. The bound proteins are eluted with 5 volumes of 10 mM reduced glutathione in 50 mM Tris (pH 8).

Example 3

Purification of His-tagged Proteins

One liter of *E. coli* BL21 (DE3) carrying the pET-TAZ fusion constructs is induced as pGEX-TAZ. Bacteria are lysed by sonication in cracking buffer (100 mM Hepes-KOH, pH7.4, 5 mM MgCl2, 500 mM KCl, 0.1% Triton-X-100, 2 mM β-mercaptoethanol and protease inhibitors cocktail from Roche Molecular Biochemicals). The lysate is spun and the supernatant are collected and incubated with 1 ml of Talon Metal Affinity Resins (Clontech) for 2 h at 4° C. The resins are washed four times with washing buffer (20 mM Hepes, pH7.4, 200 mM KCl, 10% glycerol, 10 mM imidazole and 2 mM β-mercaptoethanol) and eluted with 5 volume of elution buffer (20 mM Hepes, pH7.4, 200 mM KCl, 10% glycerol, 250 mM imidazole and 2 mM β-mercaptoethanol).

Example 4

Antibodies

Commercial TAZ antibody is purchased from Abcam and Imgenex. YAP antibody is purchased from Cell Signaling. Actin antibody is from Sigma. Rabbit polyclonal TAZ-specific antibodies are raised by injecting rabbit with GST-TAZ (amino acids 160-229) three times followed by two additional boost injections with His-TAZ (amino acids 160-229) before serum is collected. The antibody is affinity purified using immobilized His-TAZ. To detect TAZ specifically, antibody is used in the presence of 100 fold excess of GST-YAP.

Example 5

Western Blot Analysis

The indicated cells are washed once with ice-cold PBS and subsequently lysed in ice-cold lysis buffer (150 mM NaCl, 50 mM Tris-HCl, pH 7.3, 0.25 mM EDTA, pH 8.0, 1% sodium deoxycholate, 1% Triton X-100, 0.2% sodium fluoride and 0.1% sodium orthovanadate supplemented with protease inhibitor cocktail). After clearance by a spin (10,000 g, 15 min), the lysate is resolved on SDS-polyacrylamide gels and blotted onto nitrocellulose membrane. The filters are blocked in 5% skimmed milk in PBS and probed with indicated primary antibody followed by horseradish peroxidase-conjugated secondary antibody (pierce). Signals are visualized using Supersignal (Pierce).

Example 6

Retrovirus Generation and Infection

The amphotropic Phoenix packaging cells are transfected with the indicated retroviral vectors using Lipofectamine according to manufacturer's instruction (Invitrogen). After 48 h, the retroviral supernatants are collected, filtered (0.45 µm; Millipore) and added onto the target cells in the presence of 5 µg/ml of polybrene (Sigma-Aldrich) for 6-8 h. Infection is done twice. After infection, the cells are selected with puromycin (1 µg/ml) for a week before being analyzed for TAZ expression by Western blotting. For re-expression of mouse TAZ in MCF-KD-715 and MCF7-KD-652 cells, the retroviral supernatants derived from transfecting the amphotropic Phoenix cells with pBABEhygromycin-mTAZ are added to MCF-KD-715 and MCF7-KD-652 cells, which are selected with hygromycin (500 µg/ml) and puromycin (1 µg/ml) for a week before experiments are done.

Example 7 shRNA-mediated Knockdown of TAZ

Short hairpin RNAs (shRNA) against human TAZ are designed using siRNA design program from Dharmacon and subcloned into the BglII-XhoI sites of the pSuper.Retro.puro vector (Oligoengine). Efficacy of the constructs is tested through transduction into MCF7 and Hs578T cells and Western blot analysis of total cell lysates with the TAZ antibody. The sequences for the sense oligonucleotides for the knockdown construct are: KD-1, 5'-GATGAATCCGGCCTCG-GCGCC-3' (SEQ ID NO: 1); KD-650, 5'-AGAGGTACTTC-CTCAATCA-3' (SEQ ID NO: 2); KD-652, 5'-AGGTACTTCCTCAATCACA-3' (SEQ ID NO: 3); KD-715, 5'-CAGCCTCTGAATCATATGA-3' (SEQ ID NO: 8); KD-1331, 5'-AACAAACGTTGACTTAGGA-3' (SEQ ID NO: 9).

Example 8

Wound-healing Assay

Cell migration is assessed in wound healing assays. Briefly, confluent MCF10A-GFP, MCF10A-TAZ, Hs578T-KD-715 and Hs578T-KD-652 cells plated on tissue culture dishes are wounded by manual scratching with 200-µl pipette tip, washed with PBS and incubated at 37° C. in complete media. At the indicated time points, phase contrast images at specific wound sites are captured.

Example 9

Anchorage-independent Growth in Soft Agar 1.5 ml of 0.5% agar (electrograde ultra pure; Invitrogen, Carlsbad, Calif.) supplemented with RPMI, 10% FBS, are plated in six-well plates as bottom agar. Five thousand cells are mixed with 1.5 ml of 0.35% agar supplemented with RPMI, 10% FBS, and plated on the solidified bottom agar. 1 ml of media is added on top of the solidified agar layers and the colonies are allowed to grow in incubator at 37° C., 5% $CO_2$ for 2 to 3 weeks. The images of cell colonies are captured with an inverted microscope.

Example 10

Cell Motility and Invasion Assays (Transwell Assays)

Cell motility is determined by using the 24-well chambers with 8-µm pore polycarbonate membranes (BD Biosciences). The chambers are rehydrated in serum-free medium as described by the manufacturer. Complete medium with 10% FBS (750 µL) is used as chemoattractant. Suspensions of $5\times10^4$ cells in 500 µL of complete medium with 0.5% FBS are added to the inserts and incubated for 48 hours at 37° C., 5% $CO_2$. Cells remaining on the upper membrane surface of the inserts are removed with a cotton swab whereas the cells on the lower surface, as well as the ones in the wells are trypsinized and cell number are counted.

Cell invasiveness is done essentially same as cell motility assay except that the chambers used are 24-well Matrigel invasion chambers with 8-μm pore polycarbonate membranes precoated with a thin layer of Matrigel Basement Membrane Matrix (BD Biosciences).

Example 11

Tumorigenesis in Nude Mice 4- to 6-week-old female nude mice are inoculated s.c. in the left and right hind flanks or into the thoracic mammary fat pad with 5×10$^6$ MCF7-KD-715 or MCF7-KD-652 cells suspended in 100 μL of PBS and simultaneously received a 60-day release pellet containing 0.72 mg of β-estradiol (Innovative Research of America, Toledo, Ohio). Tumor development is monitored and pictures of mice are taken when the tumor sizes are bigger than 5 mm.

Example 12

Immunohistochemistry

Human breast tissue arrays (InnoGenex) are used to examine the expression of TAZ and cytokeratin (Cam 5.2, Becton Dickinson) in normal and cancer tissues. Immunohistochemistry is performed using Dako Envision™ System K 1395 (Dako, Carpinteria, Calif.). The slides are de-waxed in fresh xylene for 5 min for three times and re-hydrated sequentially with 100%, 95%, 80% and 75% ethanol and PBS (5 min for each step), followed by antigen retrieval with 2100-Retriever (PickCell Laboratories BV Prestige Medical Ltd) for 12 min in sodium citrate buffer, pH6. After cooling for 4 hr at room temperature (RT), the slides are rinsed with water and PBS with 0.1% tween-20 before quenching with 0.6% $H_2O_2$ in dark for 20 min. After rinsing with PBS, the slides are blocked with PBS with 5% goat serum and 2% BSA for 2 hr at RT and incubated with the primary antibody for overnight at 4° C. Subsequently the slides are washed with PBS with 0.1% tween-20 and followed by biotinylated secondary antibody for 2 hr. After washing, the slides are incubated with VECT-ASTATIN ABC reagent for 60 min. The diaminobenzidine tetrahydrochloride (DAB) peroxidase substrate is applied to slide for 3-5 min in dark and reactions are terminated by washing with PBS. The results are analyzed under microscope.

Example 13

TAZ Expression in Breast Cancer Cell Line

Figure 5A:
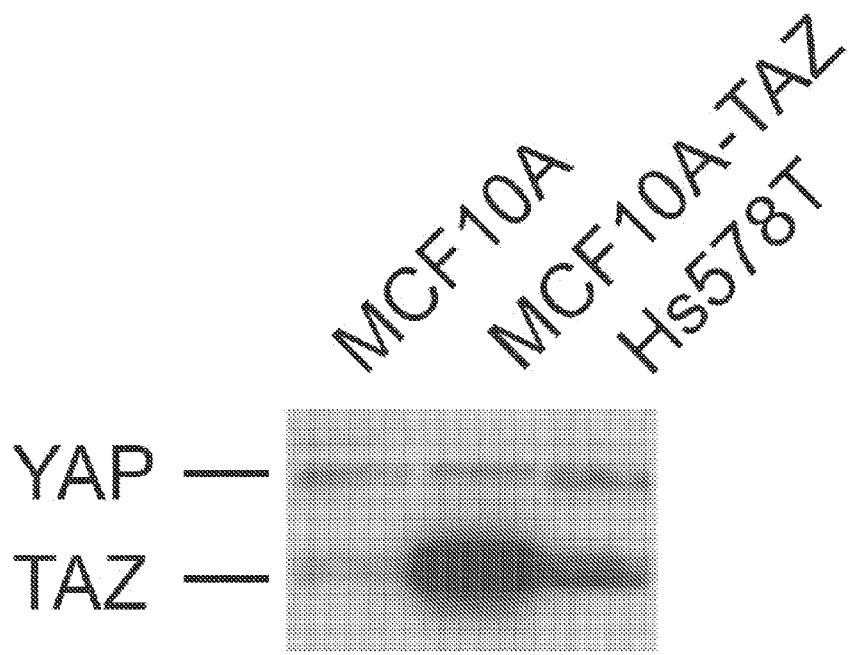
Figure 5A:
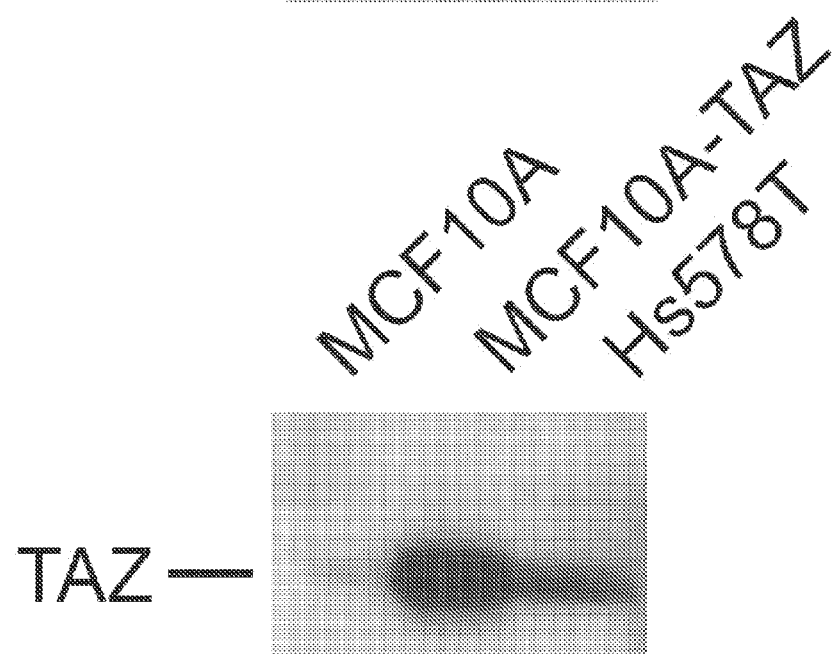
Figure 6A:
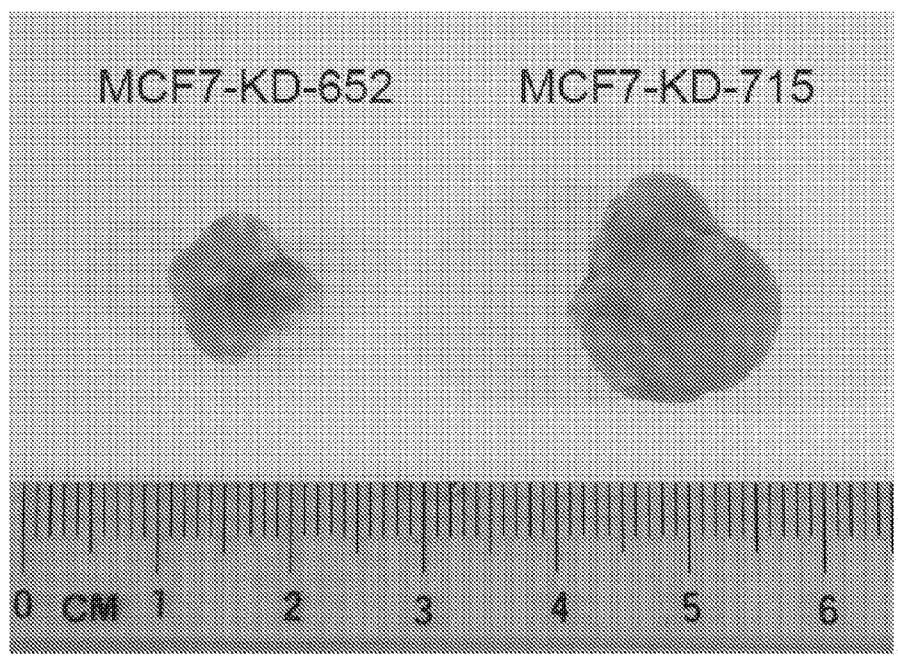
FIG. 6A and FIG. 6B. Quantification of tumors excised from mice.
Figure 6B:
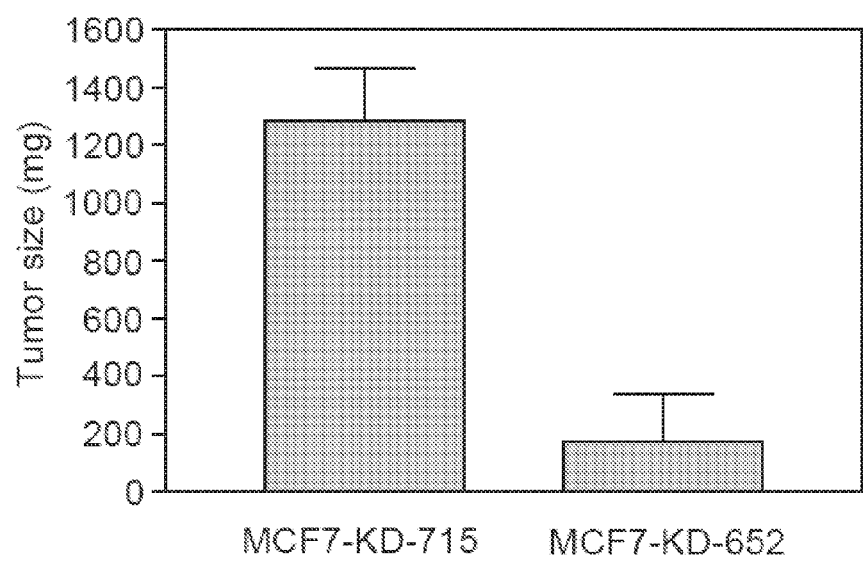
Figure 7A:
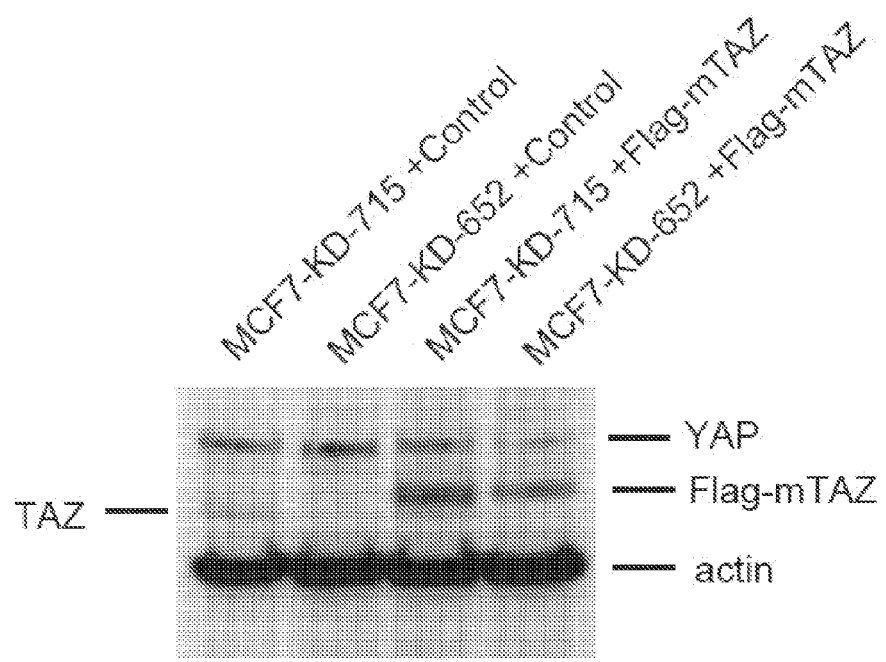
FIG. 7A, FIG. 7B and FIG. 7C. Expression of mouse TAZ (mTAZ) in TAZ knocked-down cells, MCF7-KD-652, significantly restores the growth of MCF7-KD-652 cells in soft agar. MCF7-KD-715 and MCF7-KD-652 cells are infected with pBABE hygromycin retroviral vector (control) or the retroviral vector expressing mTAZ (Flag-mTAZ). After double selection in the presence of puromycin (1 μg/ml) and hygromycin (500 μg/ml), cells are analyzed by immunoblot analysis (FIG. 7A) and growth in soft agar for two weeks (FIG. 7B). TAZ, YAP and Flag-mTAZ are indicated. Quantitation of the colony numbers of cells in the soft-agar assay from three independent experiments is shown in FIG. 7C. Bars, SEM.
Figure 7B:
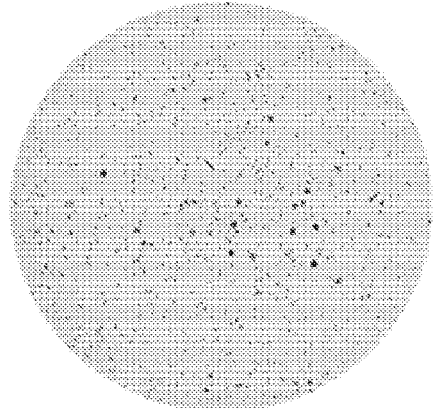
Figure 7B:
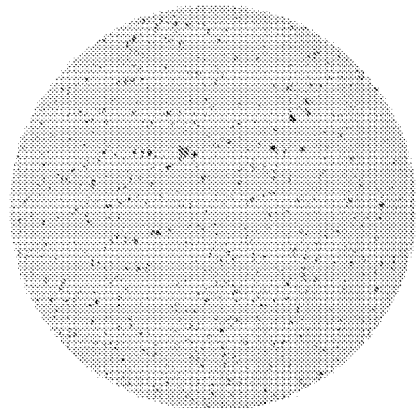
Figure 7B:
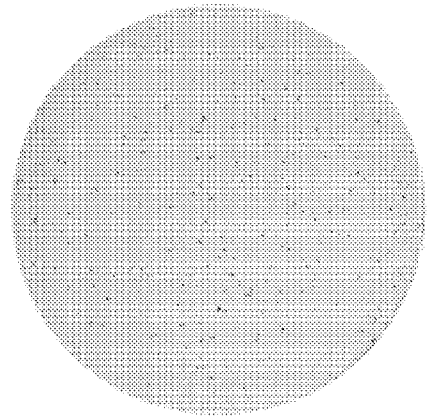
Figure 7B:
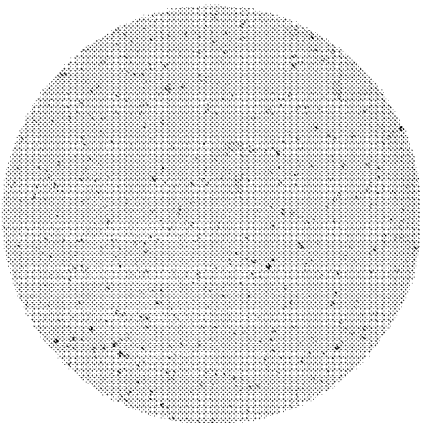
Figure 7C:
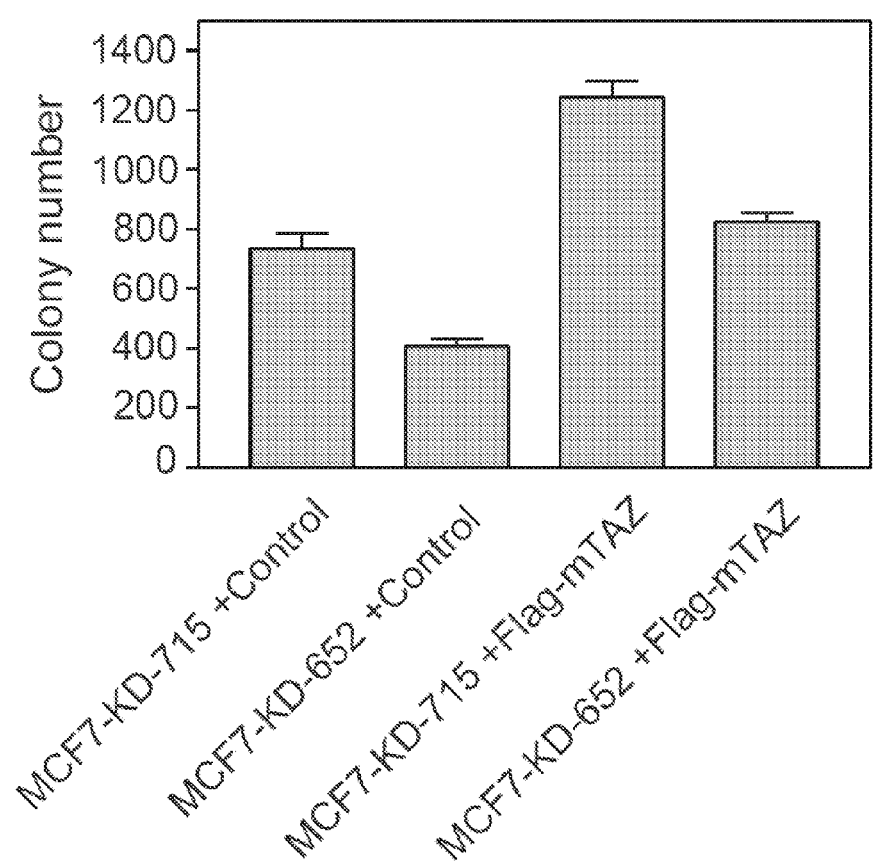

The expression of TAZ in breast cancer cell lines is examined by immunoblot analysis using total cell lysates. Testing several commercially available as well as in-house generated antibodies showed that all antibodies reacted with both TAZ and the homologous YAP. Due to efficient detection of both TAZ and YAP by a commercial antibody (IMGENEX), we have used this antibody throughout the entire study except for the experiment described in FIG. 5.

The results derived from a representative experiment, shown in FIG. 1A, indicate that TAZ is expressed at varying levels in all breast cancer cell lines examined. The expression levels of both TAZ and YAP are normalized against those of actin and the quantitative results derived from three independent experiments are presented in arbitrary units shown in FIG. 1B.

Among the breast cancer cell lines, high levels (around 4 arbitrary units) of TAZ are detected in Hs578T, BT-549, and MDA-MB-435S cells, while moderate levels (around 2 arbitrary units) are observed in MDA-MB-231, BT-20, and T-47D cells. MCF10A, MCF7, MDA-MB-453, ZR-75-1, and BT-474 cells express low levels (around 1 arbitrary unit) of TAZ.

Significantly, three (Hs578T, BT-549, and MDA-MB-435S) of the four highly invasive cancer cell lines exhibit high levels of TAZ expression with MDA-MB-231 cells expressing moderate levels. These four cell lines are shown in Neve et al (2006) to correspond to basal-like or basal B cancer types, representing invasive breast cancer cell types.

Most (five out of 7) of the weakly invasive cells express low levels of TAZ with two cell lines (BT-20 and T-47D) expressing moderate levels. These results suggest that the majority of highly invasive breast cells express high levels of TAZ, while the majority of weakly invasive cells express low levels of TAZ.

No such correlation of YAP expression levels with invasiveness of breast cancer cells is noticed (FIG. 1B). The correlation of TAZ expression level with the invasiveness of breast cancer cells suggests that TAZ may be part of the mechanism governing the invasiveness of breast cancer cells.

Example 14

Figure 2A:
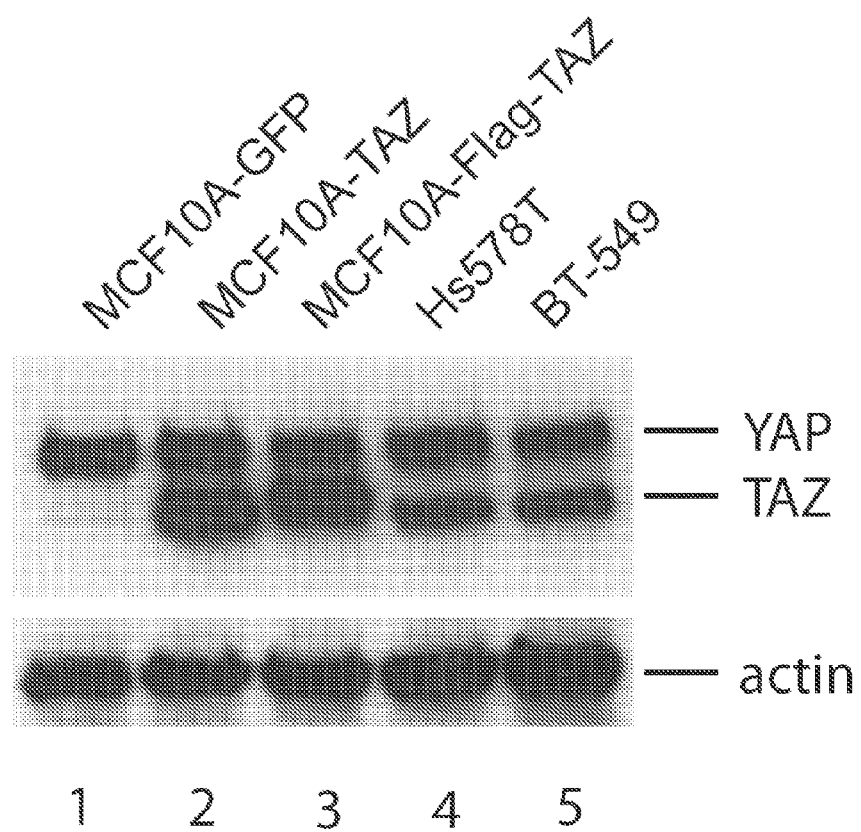
FIG. 2A, FIG. 2B and FIG. 2C. TAZ promotes migration and invasion of MCF10A cells.

Overexpression of TAZ in MCF10A Cells Induces Fibroblast-like Morphology and Promotes Cell Migration and Invasion To examine the functional consequence of TAZ expression in breast cancer cells, we overexpressed TAZ or Flag-tagged TAZ in MCF10A cells (which exhibit low endogenous levels of TAZ) to levels that are about 2-3 fold of those found in high-expressing invasive cells such as Hs578T and BT-549 (FIG. 2A). This is achieved by retrovirus-mediated transduction, as MCF10A cells are not satisfactorily transfected to express exogenous proteins. Pools of MCF10A cells infected with the appropriate retrovirus are analysed to avoid clonal variations. EGFP expressing cells (left panels of FIG. 2B) retained the epithelial appearance seen of the parental MCF10A cells. However, cells overexpressing TAZ (right panels of FIG. 2B) or Flag-TAZ (data not shown) developed a more reflectory and spindle-shaped fibroblast-like morphology characteristic of cell transformation.

Figure 2B:
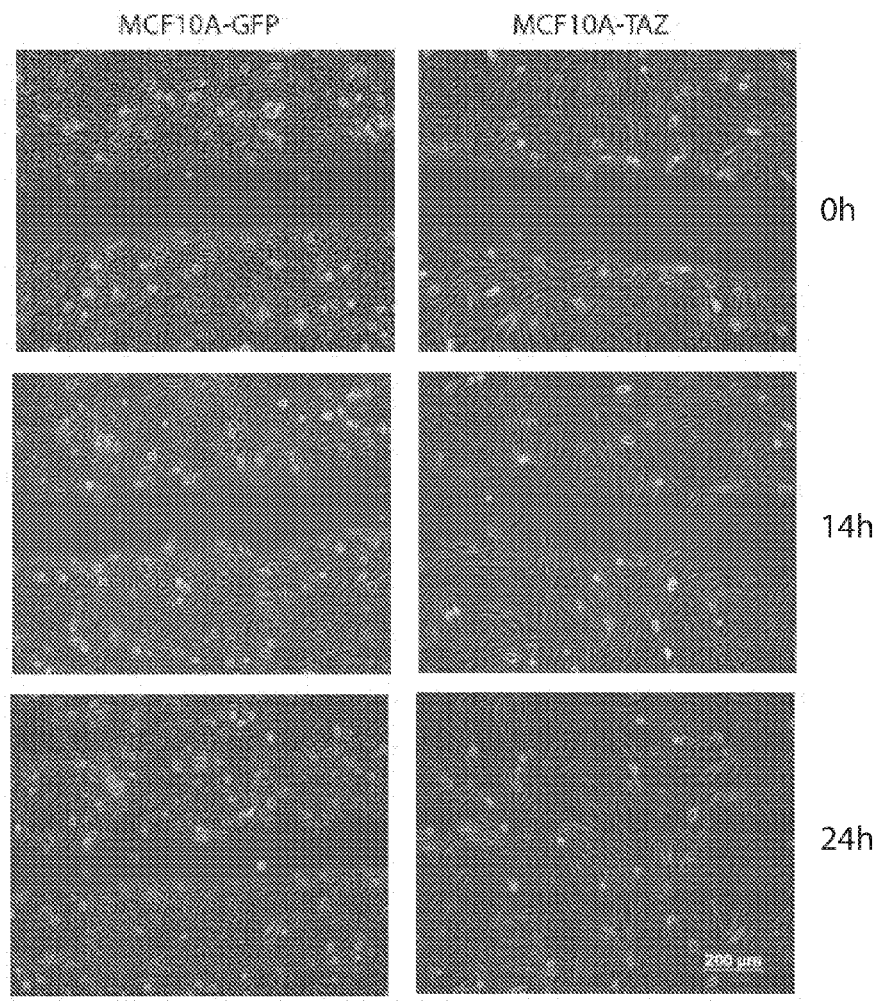
Figure 2C:
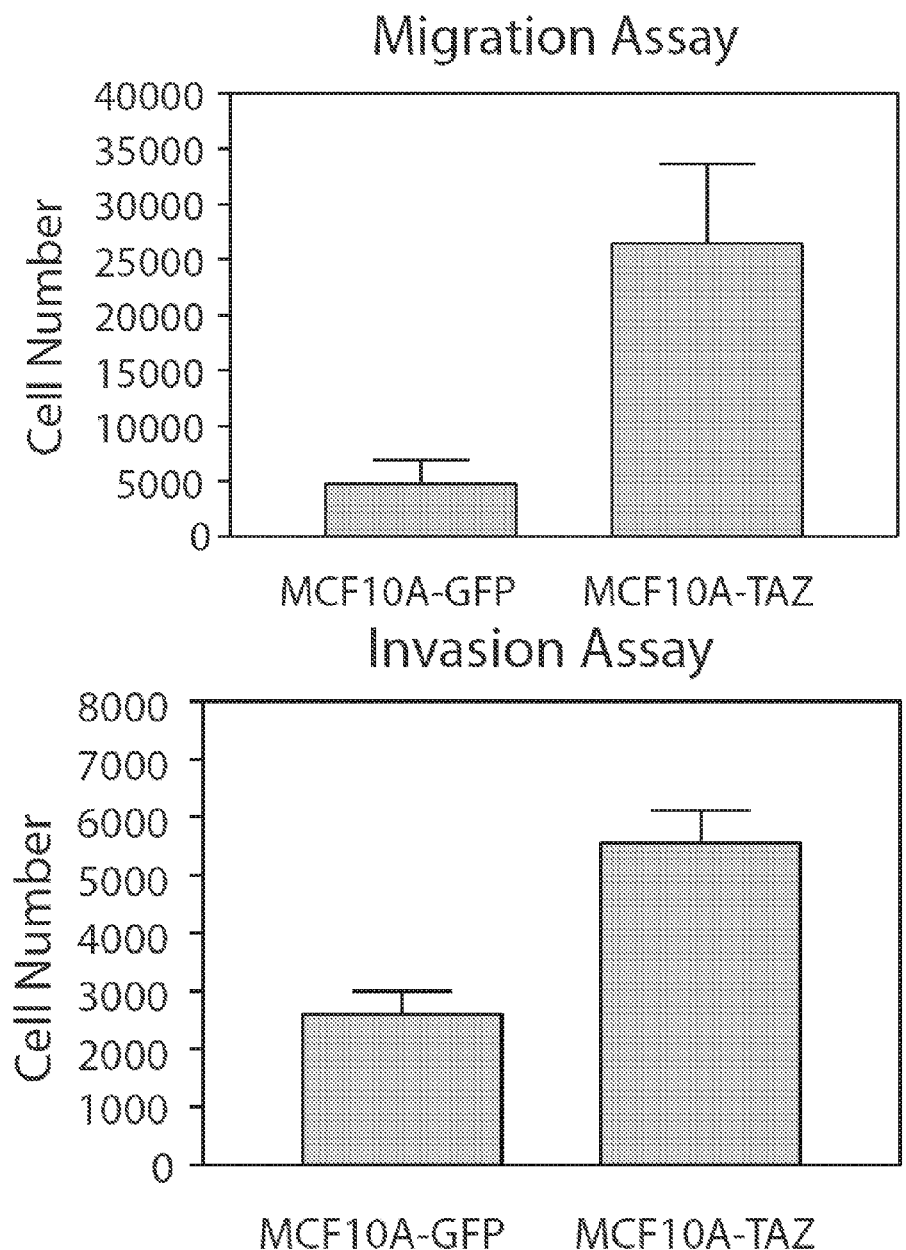

Since TAZ expression levels correlate with the invasiveness of breast cancer cells, we examined whether TAZ overexpression could promote cell migration and invasion. Using the wound-healing assay, we compared the cell mobility of MCF10A cells expressing TAZ relative to the cells expressing EGFP (FIG. 2B). The mobility of TAZ-expressing cells is dramatically enhanced. Within 14 hr, the area of wound is significantly recovered by the migrated TAZ-overexpressing cells. The area of wound is completely recovered by the migrated cells within 24 hr (right panels). In marked contrast, the wound closure of MCF10A cells expressing EGFP is not significant within 14 hr and is only partial within 24 hr (left panels). The motility and invasiveness of these cells are independently assessed using the Transwell assay (FIG. 2C). The migration and invasiveness of TAZ expressing cells increased about 5 and 2-3 folds, respectively, compared to control cells expressing EGFP. These results suggest that TAZ promotes cell migration and invasion and these properties may contribute to the altered morphology of cells overexpressing TAZ.

Figure 3A:
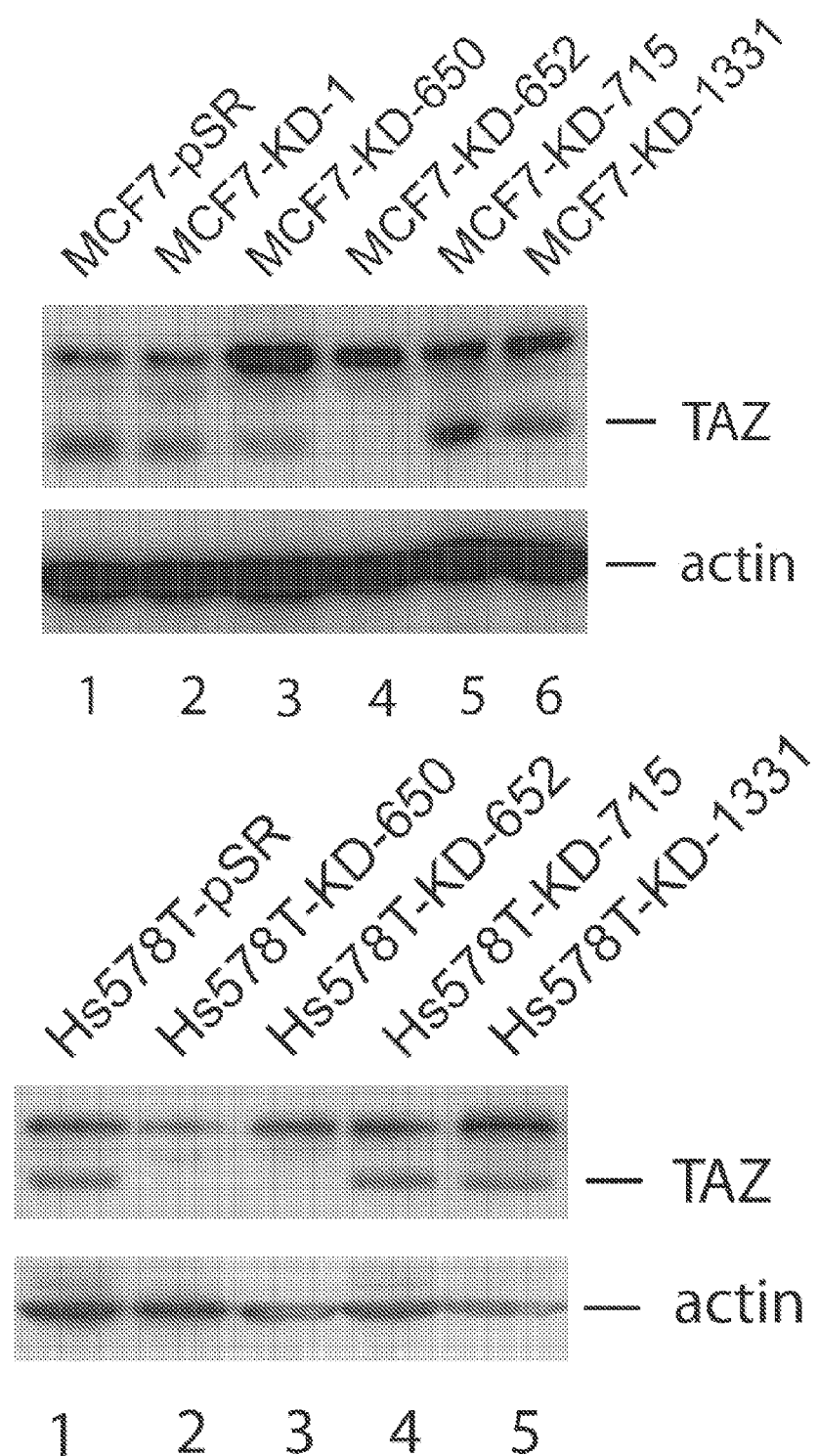
FIG. 3A, FIG. 3B, FIG. 3C and FIG. 3D. TAZ knockdown in MCF7 cells enhances epithelial morphology and in Hs578T cells suppresses cell migration and invasion.
Figure 3B:
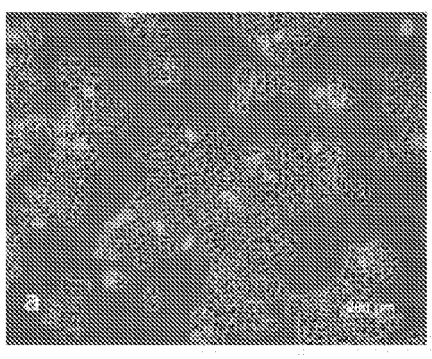
Figure 3B:
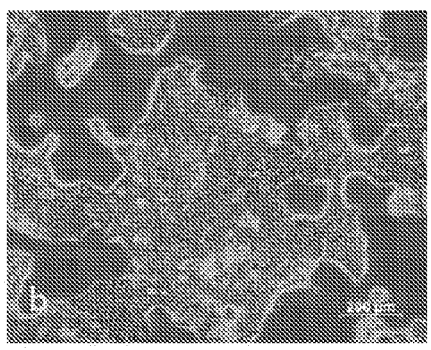
Figure 3B:
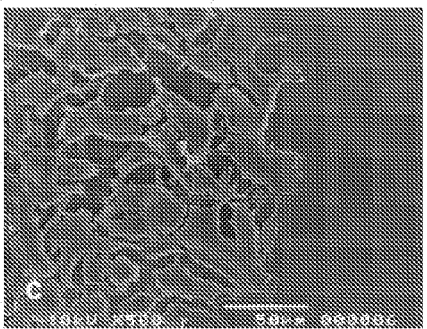
Figure 3B:
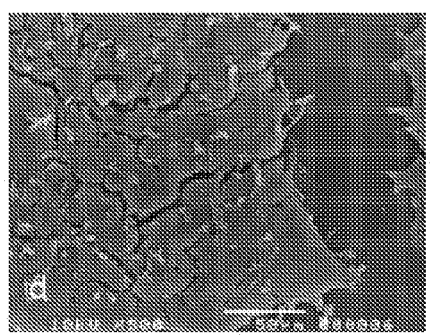
Figure 3C:
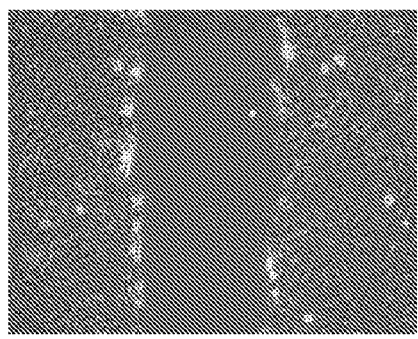
Figure 3C:
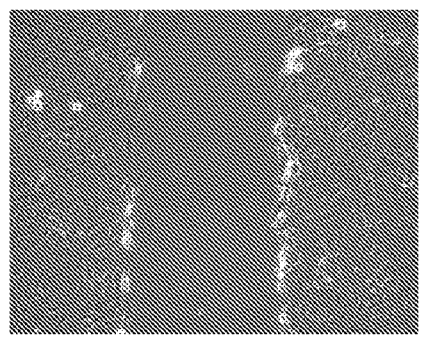
Figure 3C:
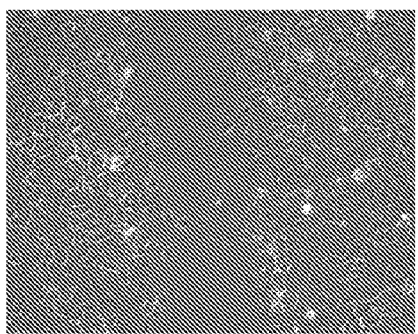
Figure 3C:
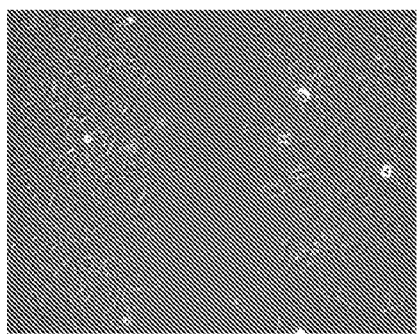
Figure 3C:
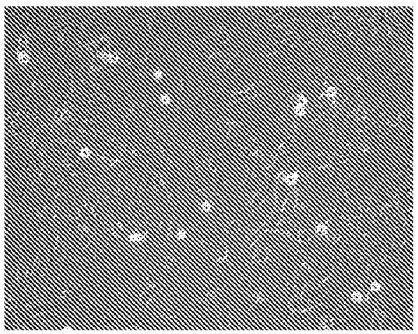
Figure 3C:
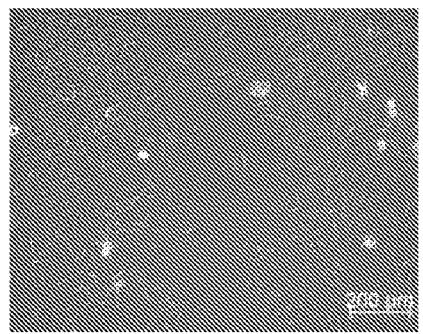
Figure 3D:
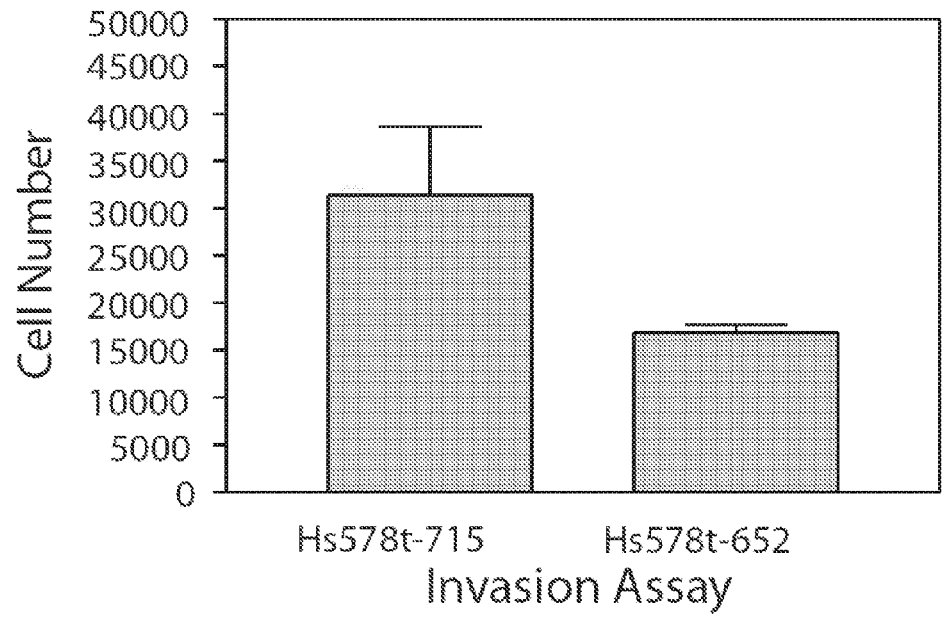
Figure 3D:
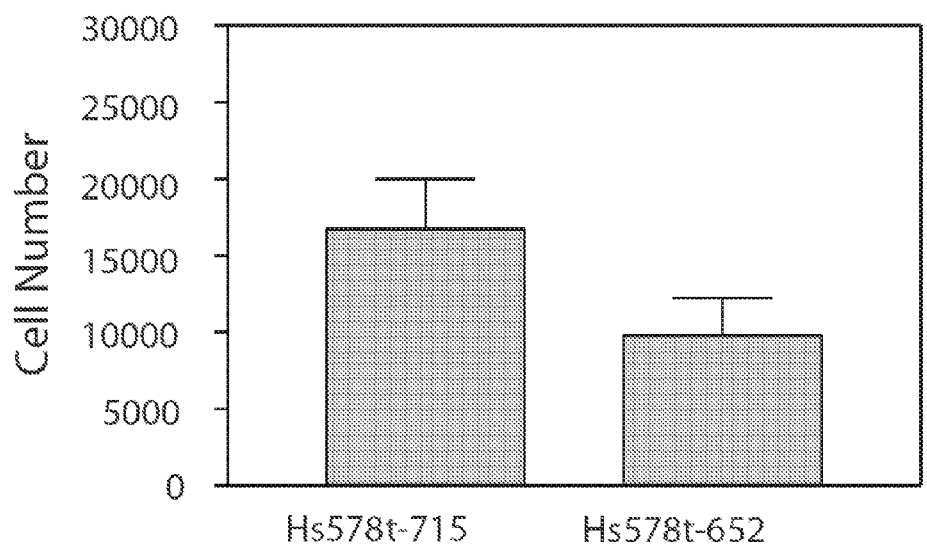

Example 15 shRNA-mediated Knockdown of TAZ in MCF7 and Hs578T Cells Suppresses Cell Migration and Invasion To verify a role for TAZ in cell migration and invasion, a complimentary but independent approach is used that is based on RNA-interference (RNAi)-mediated knockdown of gene expression. For sustained knockdown while avoiding clonal variations, we analysed pools of cells stably infected with a retrovirus-based vector expressing shRNA targeting various regions of TAZ mRNA. One reported RNAi target site (KD-1) plus 4 other sites of TAZ mRNA are tested for their susceptibility to knocking down the expression of TAZ protein in MCF7 cells as assessed by immunoblot analysis. As shown in FIG. 3A (left panel), the shRNA based on the reported target noticeably reduced the level of TAZ protein. Among the shRNAs based on the four new targets, two (715 and 1331) had no significant effect on TAZ protein levels, one (650) has RNAi effect comparable to the reported one, whereas another (652) had the most efficient effect of suppressing TAZ expression. The four shRNAs expressing retroviruses are also used to infect Hs578T cells (right panel) and pools of stably transduced cells are analyzed for TAZ expression. Again, shRNA 715 and 1331 had no significant effect, while both shRNA 650 and 652 reduced the protein level of TAZ significantly. We therefore used cells knocked down with shRNA 652 for subsequent analysis in comparison with cells transduced with the shRNA715, as cells transduced with shRNA715 behaved like parental and vector-transduced cells in all analysis. Concomitant with reduced TAZ expression, the clusters of cells became more densely-packed and compact sheets of cells with the cell density of the clusters being enhanced in the MCF7-KD-652 cells as compared to MCF7-KD-715 cells (upper panels, FIG. 3B). Scanning electron microscopy revealed that the space between cells is reduced in MCF7-KD-652 cells as compared to MCF7-KD-715 cells (lower panels, FIG. 3B), resulting in the appearance of more tightly aligned/packed and compact epithelia. This observation is obvious when cells are plated at either low or high density cultured under standard conditions. As MCF7 cells do not migrate and invade significantly using most assays, we have analyzed the migration and invasion using Hs578T cells. Relative to Hs578T-KD-715 cells, with no detectable RNAi effect, which migrated robustly in the wound-healing assay (left panel, FIG. 3C), knockdown of TAZ significantly reduced the migration of Hs578T-KD-652 cells (right panels, FIG. 3C). The reduction of migratory and invasive abilities is also revealed using the Transwell assay (FIG. 3D). These RNAi experiments further bolster the conclusion derived from the overexpression experiments that TAZ is an important regulator of cell migration and invasion. Its expression levels correlate negatively with the epithelial appearance of breast cells and positively with migratory and invasive properties.

Example 16

TAZ is Important for Anchorage-Independent Growth and Tumorigenesis

Figure 4A:
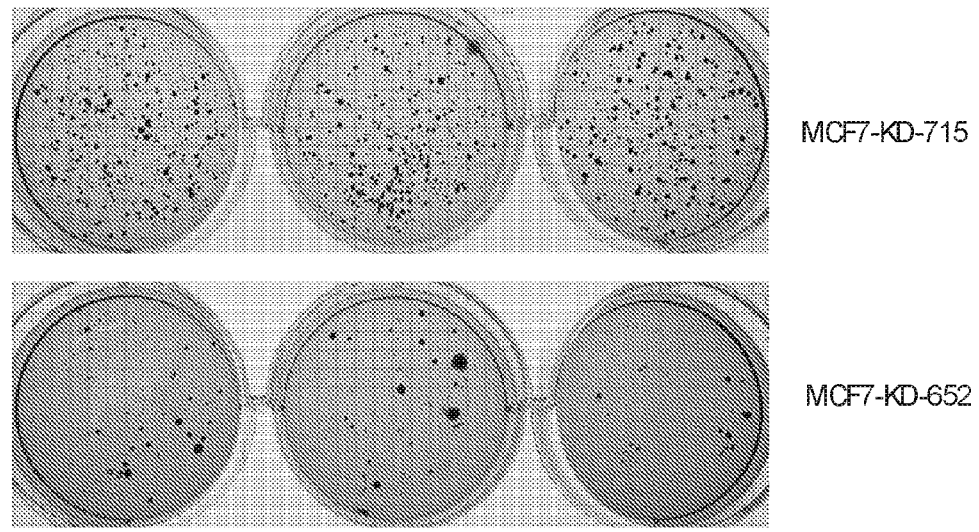
FIG. 4A.
Figure 4B:
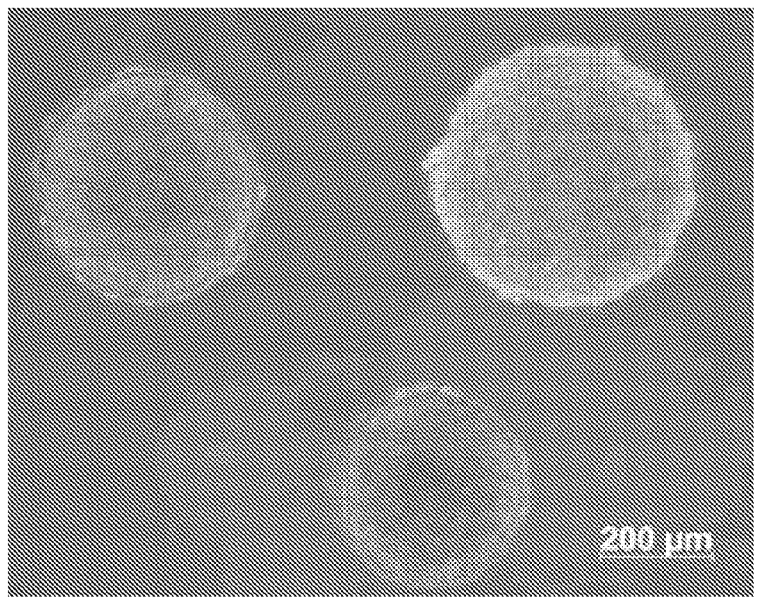
FIG. 4B and FIG. 4C. TAZ knockdown in MCF7 cells suppresses anchorage-independent growth in soft-agar and tumorigenesis in nude mice.
Figure 4B:
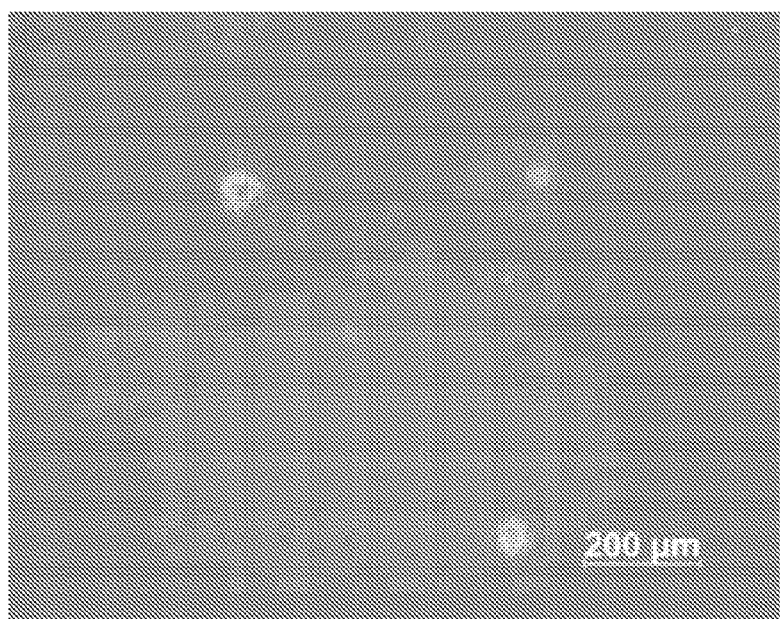
Figure 4C:
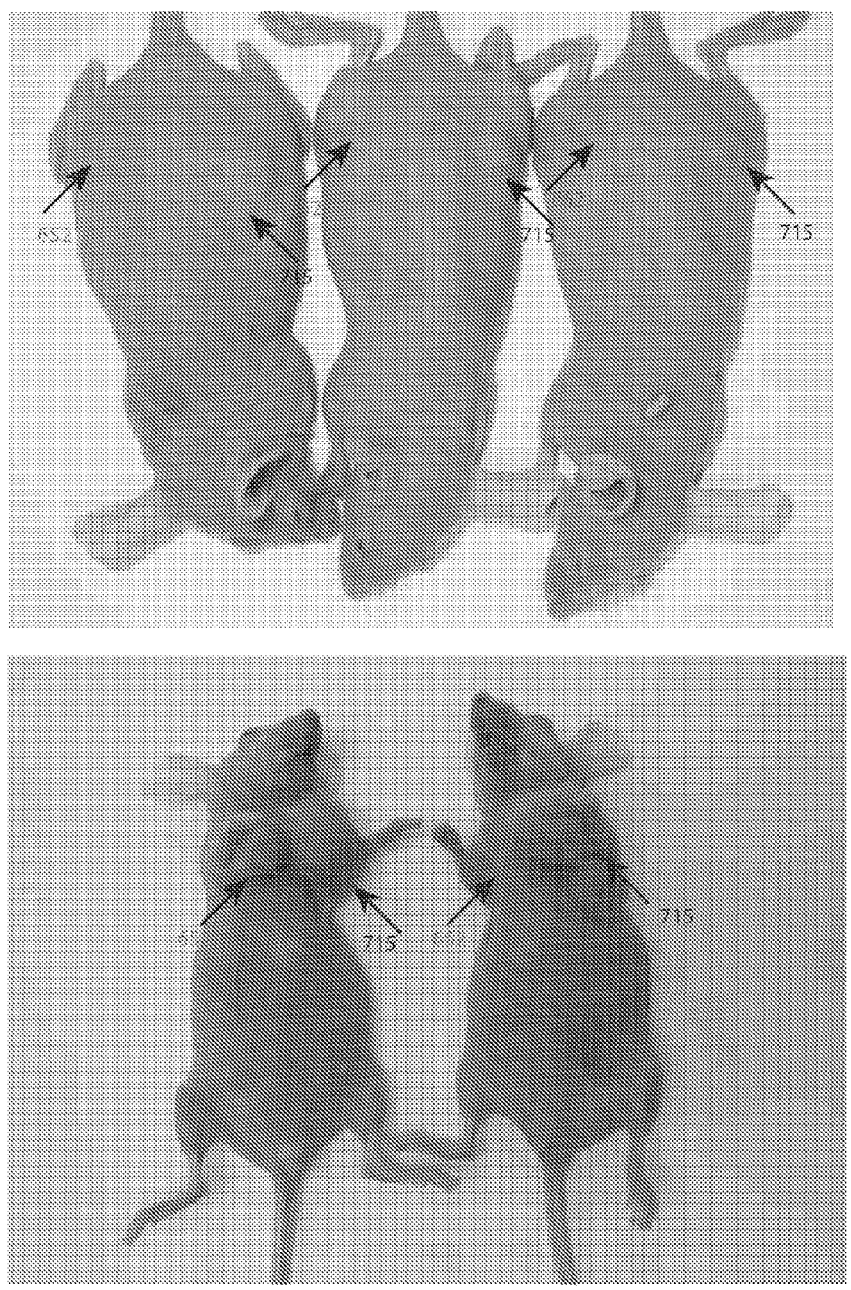

To examine the importance of TAZ in tumorigenesis of breast cancer cells, we firstly assessed the anchorage-independent growth capability of TAZ-knocked-down MCF7-KD-652 cells in comparison with MCF7-KD-715 cells. MCF7-KD-715 cells grew well in soft agar (upper panels, FIG. 4A), whereas the number of colonies grown in soft agar is dramatically reduced for MCF7-KD-652 cells. Compared to the well-developed spheres of cell colonies of MCF7-KD-715 cells (left panel, FIG. 4B), MCF7-KD-652 cells failed to grow up and only small aggregations of cell debris are observed (right panel, FIG. 4B). These results suggest that TAZ is essential for anchorage-independent growth of MCF7. We have subsequently examined whether TAZ contributes to tumorigenesis in nude mice. MCF7-KD-715 and MCF7-KD-652 cells are separately injected into the thigh and fat pad of nude mice and the growth of the tumors is monitored (FIG. 4C). Compared to MCF7-KD-715 cells (right side), MCF7-KD-652 cells (left side) are compromised in forming tumors at both the thigh (left panel) and fat pad (right panel) injection sites. The quantitative analysis of the resulting tumors is shown in supplementary FIG. S1. These results suggest that TAZ is also important for in vivo tumorigenesis of MCF7 cells.

Example 17

Overexpression of TAZ in Breast Cancers

To assess whether our findings obtained from analyzing the breast cancer cells have physiological and clinical relevance, we have examined TAZ expression in tissue sections derived from primary breast cancers. To overcome the cross-reactivity of anti-TAZ antibodies with YAP, we generated rabbit antibodies to a region of TAZ that is most divergent from YAP. The affinity-purified antibodies preferentially recognized TAZ but also reacted with YAP at lower efficiency (left panel, FIG. 5A). However, the antibodies recognized specifically TAZ in the presence of 100 folds excess (over the antibody) of recombinant YAP fragment corresponding to the TAZ region used as the antigen (right panel, FIG. 5A). Using this approach to specifically detect TAZ, immunohistochemistry is used to examine the primary breast cancer samples. Among 126 breast cancer samples analyzed, 27 (21.4%) overexpressed TAZ and most (21 samples) of the TAZ-expressing cancers are of invasive (infiltrating) ductal carcinomas (IDC), suggesting that TAZ is overexpressed in a significant fraction of the IDC. A representative positive labeling of TAZ in IDC is shown (right panels, FIG. 5B). The summary of our immunohistological analysis of the cancer samples is shown in Table E1 below. These results suggest that TAZ overexpression is likely to be important for the progression of breast cancer into IDC and establish the physiological and clinical relevance of our findings with breast cancer cell lines.

TABLE E1

Analysis of TAZ Overexpression in Different Types of Breast Cancers.

| Nor. Breast | fibroadenoma | LCIS | IDC | ILC | DCIS | LN met | Medullary Ca |
|---|---|---|---|---|---|---|---|
| 0/4 | 0/8 | 2/2 | 21/87 | 3/6 | 0/7 | 1/11 | 0/5 |

Immunohistochemistry was used to examine the expression of TAZ in each breast cancer type.
The numbers shown represent the numbers of samples overexpressing TAZ in total number of sample of each breast cancer type.
Nor. Breast, normal breast;
LCIS, lobular carcinoma in situ;
IDC, invasive ductal carcinoma;
ILC, invasive lobular carcinoma;
DCIS, ductal carcinoma in situ;
LN met, lymph node metastasis;
Medullary ca, medullary carcinoma.

Example 18

TAZ Interacts with Transcriptional Factors TEAD1, TEAD2, TEAD3 and TEAD4

In vitro binding experiments with TAZ and GST-TEADs and HA-TEADs (expressed in cells) are conducted, using methods described herein and known in the art.

In a first experiment, cell extracts derived from Hs578t cells are incubated with immobilized GST-TEAD1 (96-412), GST-TEAD2 (121-448), GST-TEAD3 (115-436), GST-TEAD4 (119-435) or GST. Proteins retained by the beads, together with the starting material, are resolved by SDS-PAGE followed by immunobloting with antibodies that react with both TAZ and YAP.

Figure 8A:
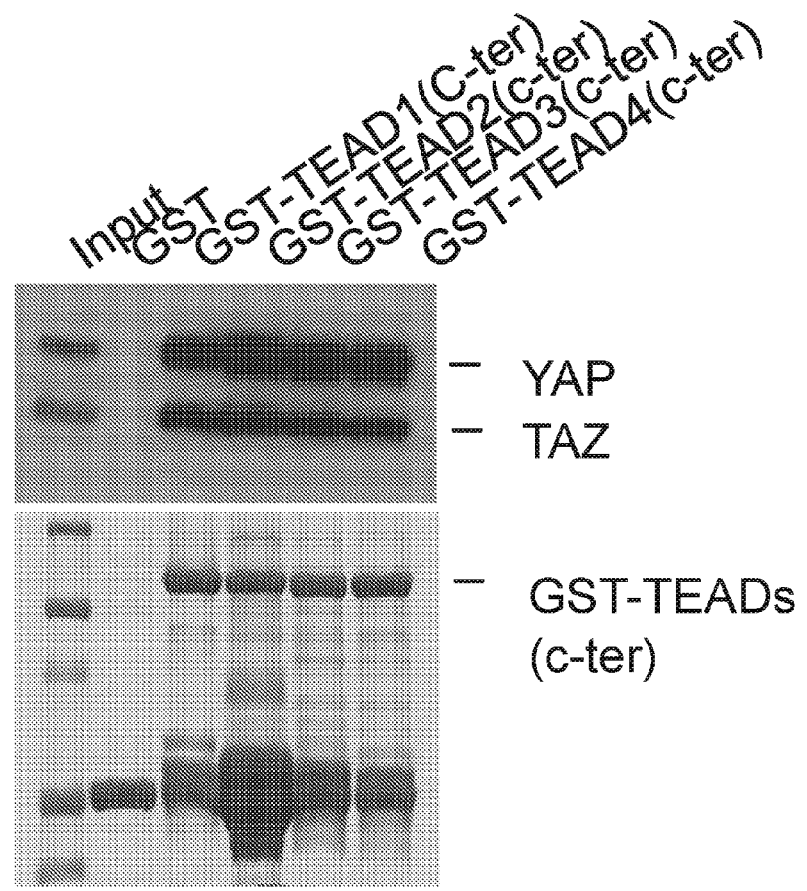
FIG. 8A and FIG. 8B. Retention of TAZ and YAP by immobilized C-terminal region of TEAD1-4.

The results are shown in FIG. 8A. This figure shows that both TAZ and YAP are efficiently retained by the immobilized GST-TEADs but not GST.

In a second experiment, s578T cells stably transduced with retroviral vector to express HA-TEAD1-4 are lysed and the resulting cell lysates were immunoprecipitated with anti-HA antibodies. The immunoprecipitates, along with starting materials, are resolved by SDS-PAGE followed by immuno-bloting using anti-HA antibody or antibodies that react with both TAZ and YAP.

Figure 8B:
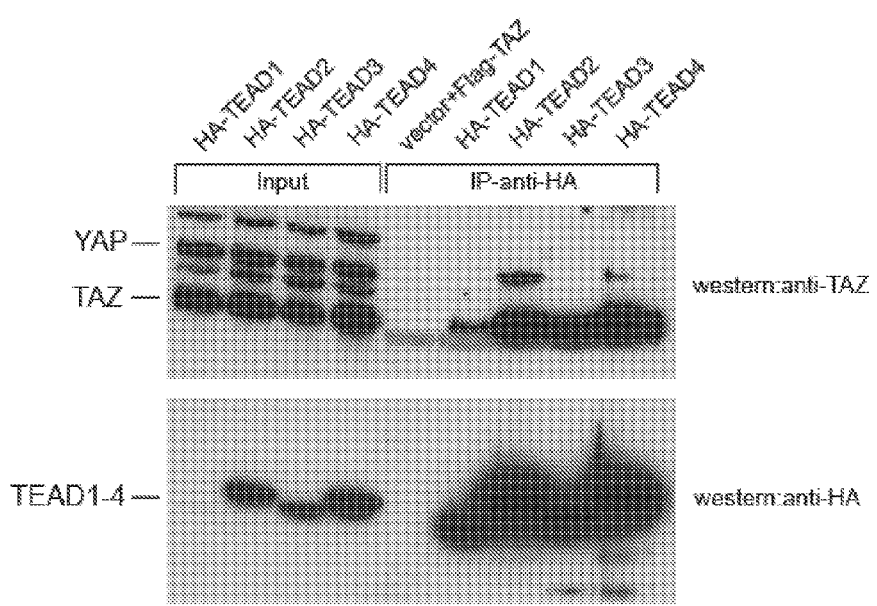
Figure 9:
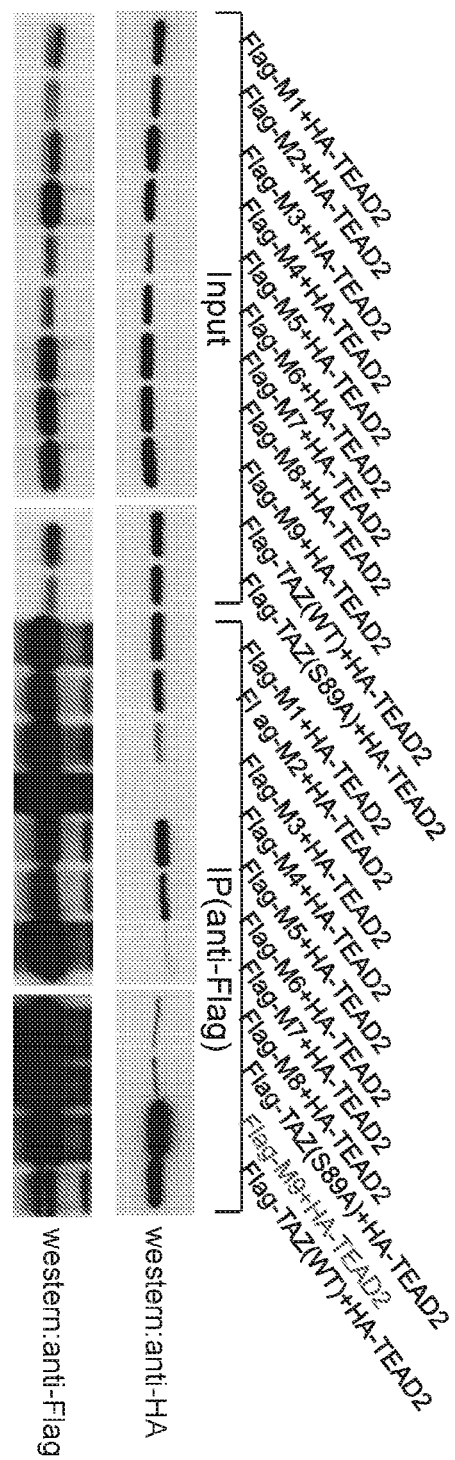
FIG. 9 is a figure showing the identification of residues in TAZ that are important for interaction with TEAD.

The results are shown in FIG. 8B. This figure shows that endogenous TAZ and YAP (at much less efficiency) are co-immunoprecipiated with stably-expressed HA-TEAD1-4.

Example 19

Identification of TAZ Residues Involved in Binding to TEAD2

Region of TAZ are important for interaction with TEAD2. F52A and F53A mutants are unable to interact with TEAD2.

Example 20

Mutant F53A Defective in Interaction with TEAD2 is Excluded from Nuclear Accumulation MCF10A cells infected with Flag-tagged TAZ-S89A and M9 (i.e., F53A) are stained with anti-Flag antibody, using methods described here and known to the skilled reader.

Figure 10:
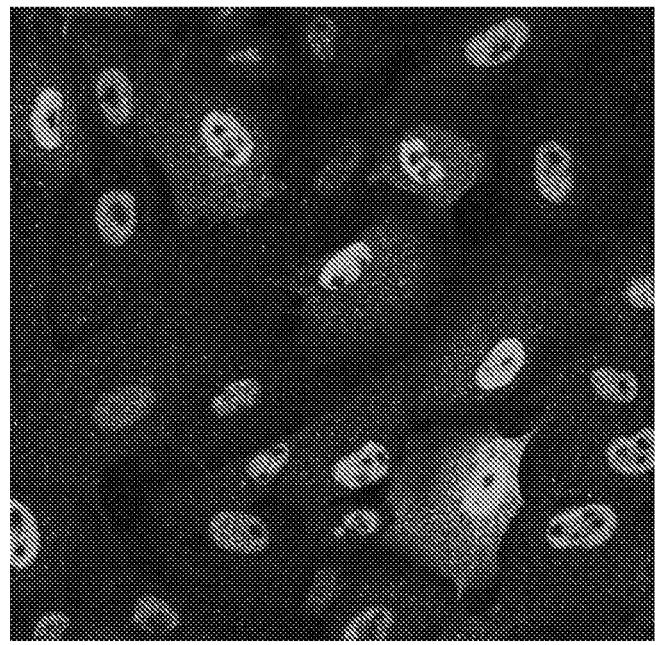
FIG. 10 is a figure showing results of experiments testing the ability of TAZ mutants to accumulate in the nucleus.
Figure 10:
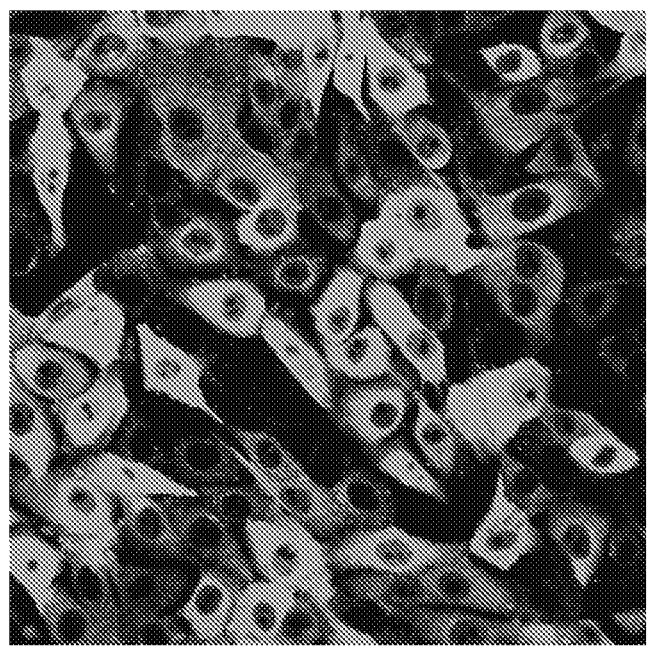

FIG. 10 shows the results. The TEAD-binding mutant fails to accumulate in nucleus. This shows that TEAD is essential for TAZ to accumulate in the nucleus.

Example 21

Mutant F53A Defective in Interaction with TEAD2 Does Not Drive Anchorage-independent Growth 20,000 MCF10A cells infected with either TAZ-S89A or M9 (i.e., F53A) mutant are grown in soft agar for one month and colonies are stained, using methods described here and known to the skilled reader.

Figure 11:
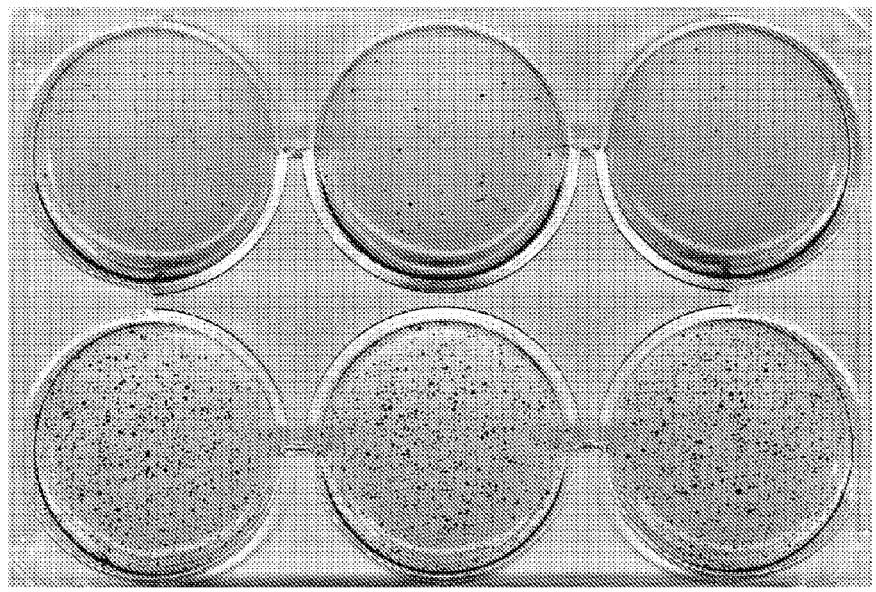
FIG. 11 is a figure showing results of experiments testing the ability of TAZ mutants in driving anchorage-independent growth.

FIG. 11 shows the results. The TEAD-binding mutant is unable to grow in soft-agar. This shows that interaction with TEAD is essential for TAZ to induce oncogenic transformation.

Example 22

TAZ Induces Expression of Secreted Proteins and Surface Membrane Proteins

TAZ (S89A) is a mutant of TAZ generated by standard mutagenesis techniques. Serine at position 89 of TAZ is mutated to alanine. It is shown to be a gain of oncogenic function mutant.

RT-PCR is conducted on cells expressing TAZ and TAZ (S89A) to establish expression of a number of secreted proteins and surface membrane proteins.

Figure 12:
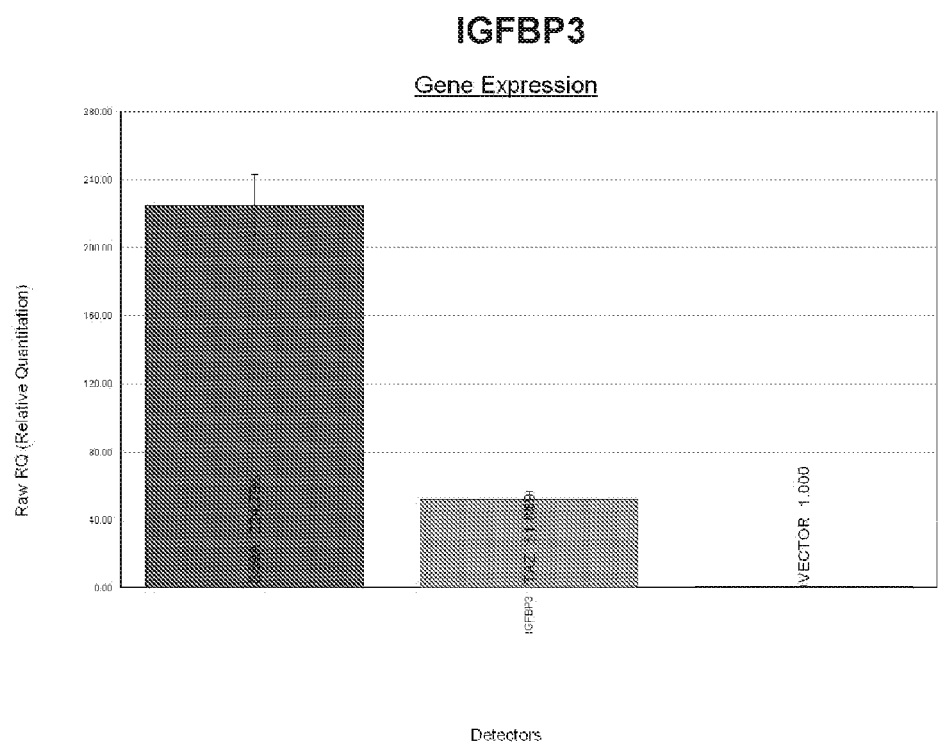
FIG. 12 is a figure showing results of RT-PCR experiments showing the expression of secreted proteins and surface membrane proteins.
Figure 12:
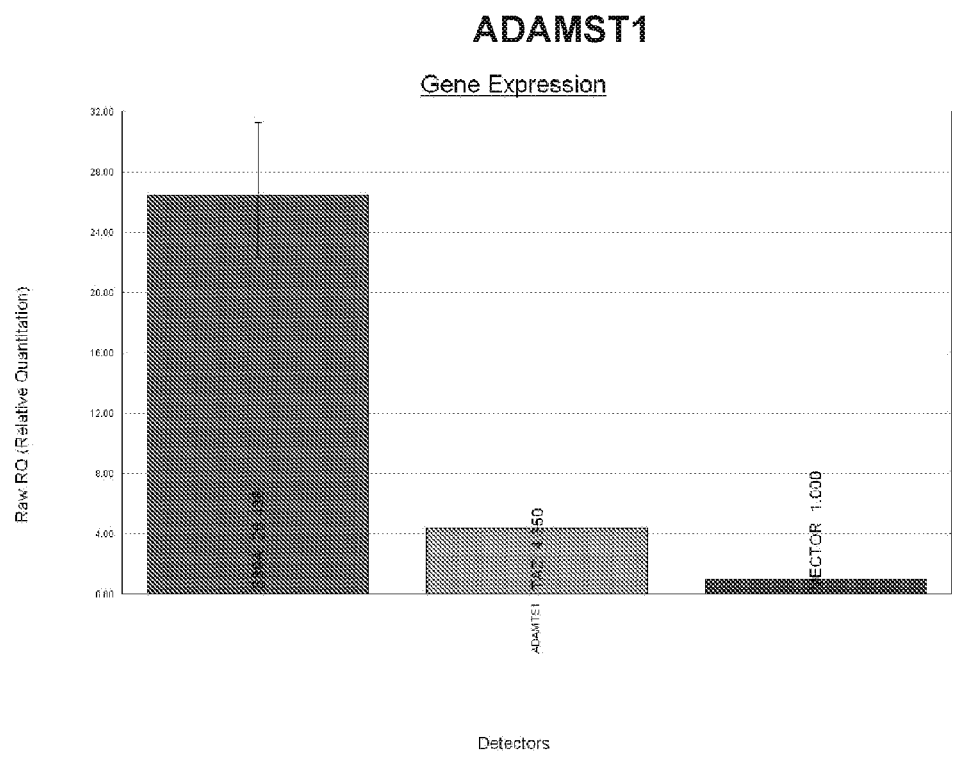
Figure 12:
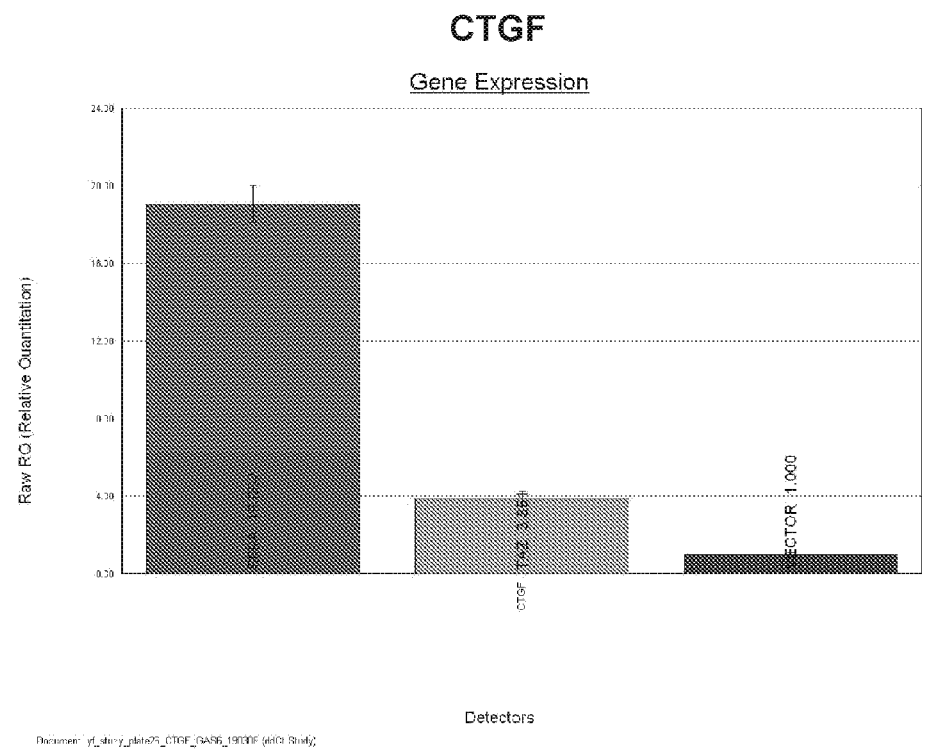
Figure 12:
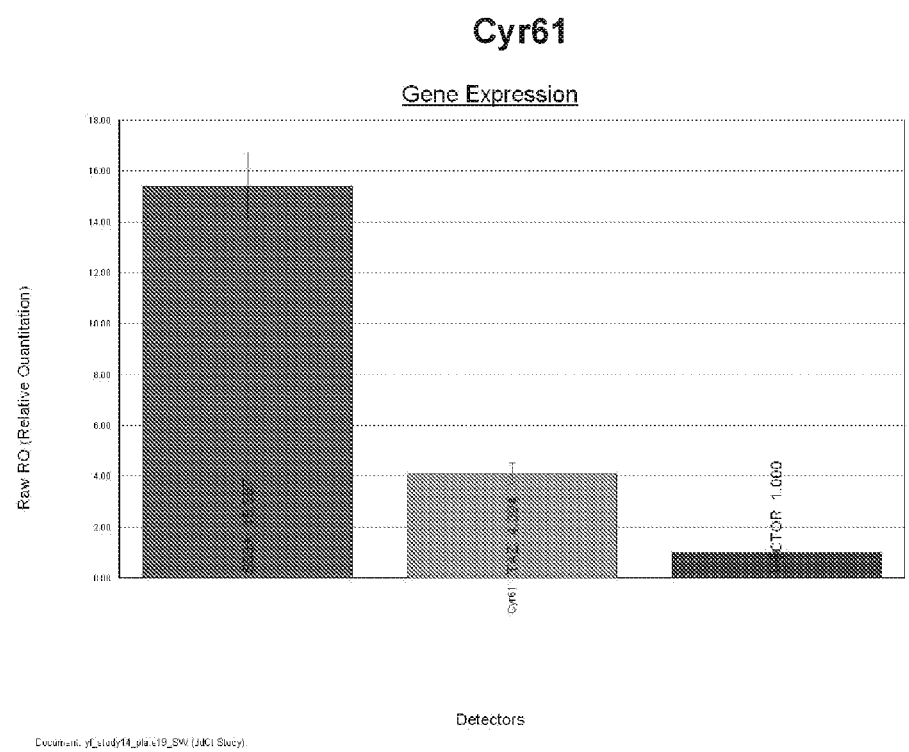
Figure 12:
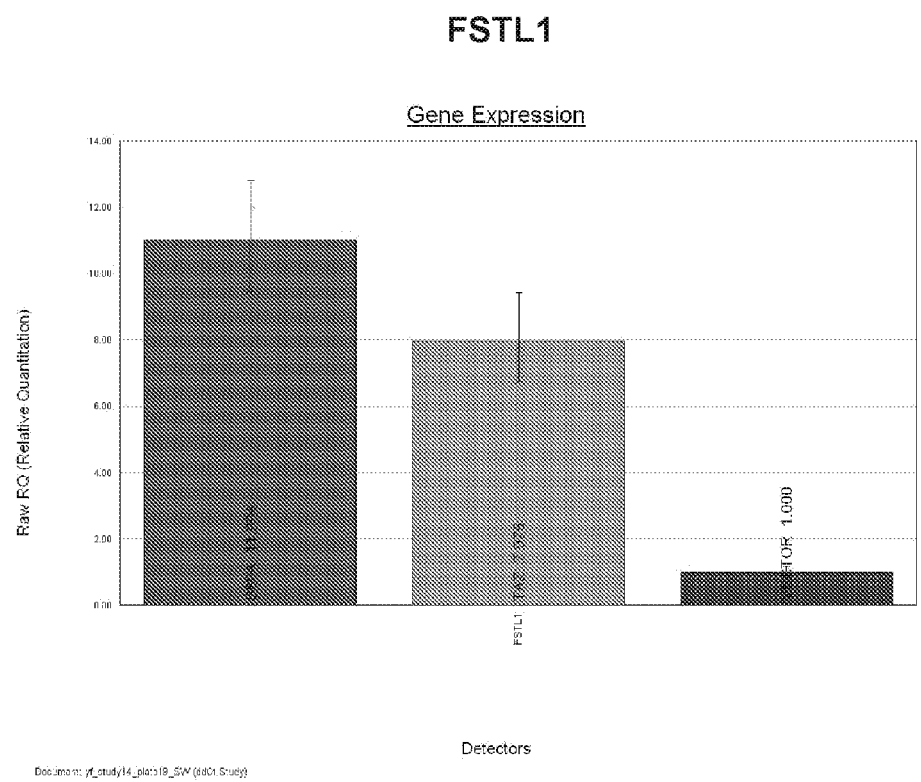
Figure 12:
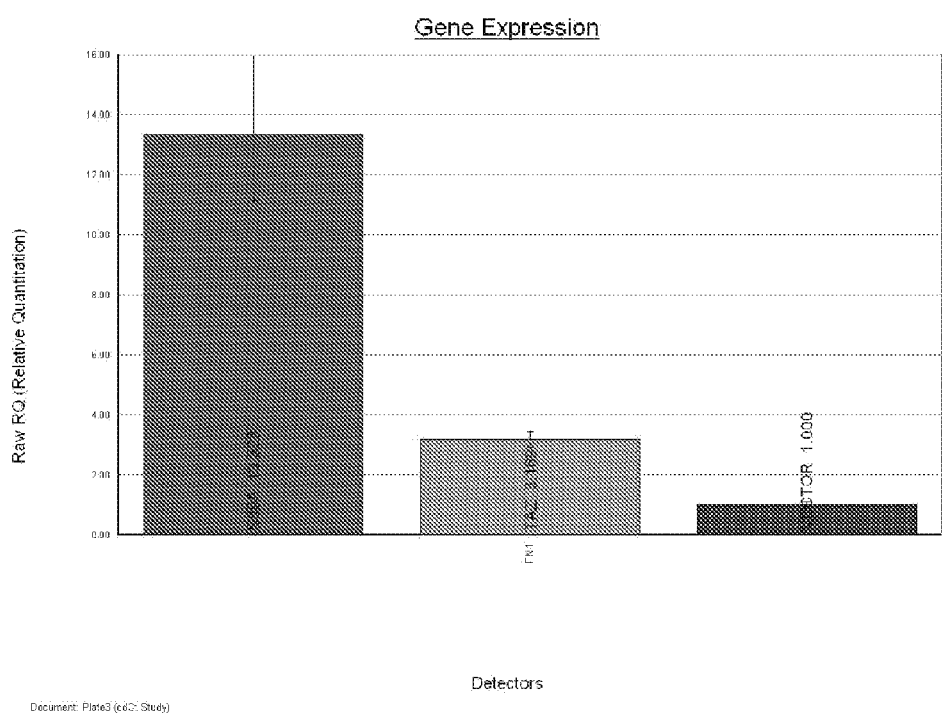
Figure 12:
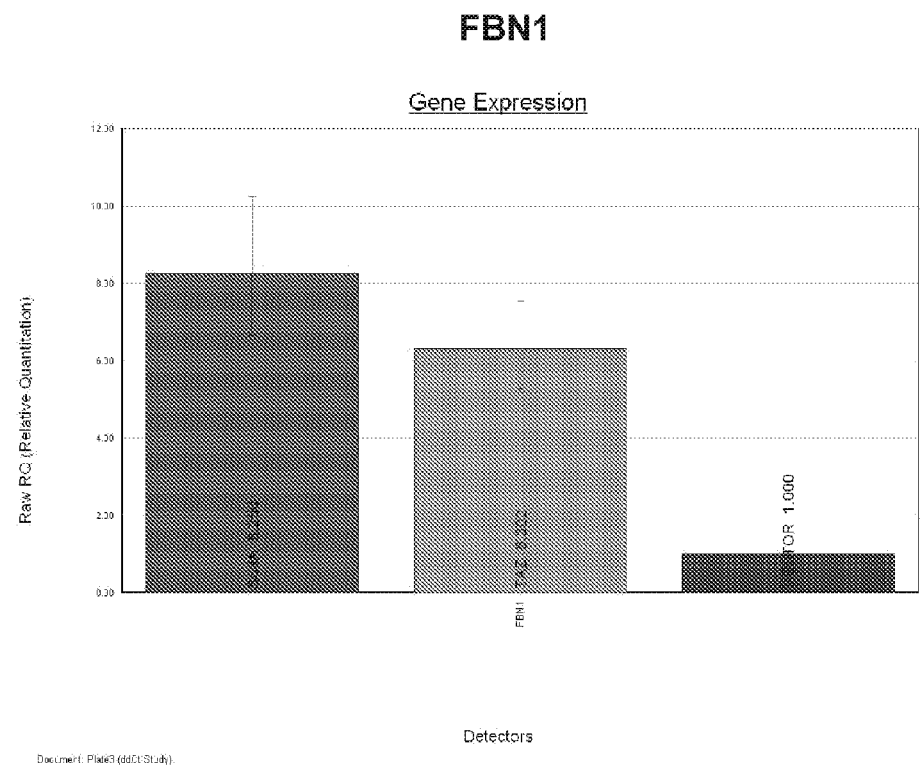
Figure 12:
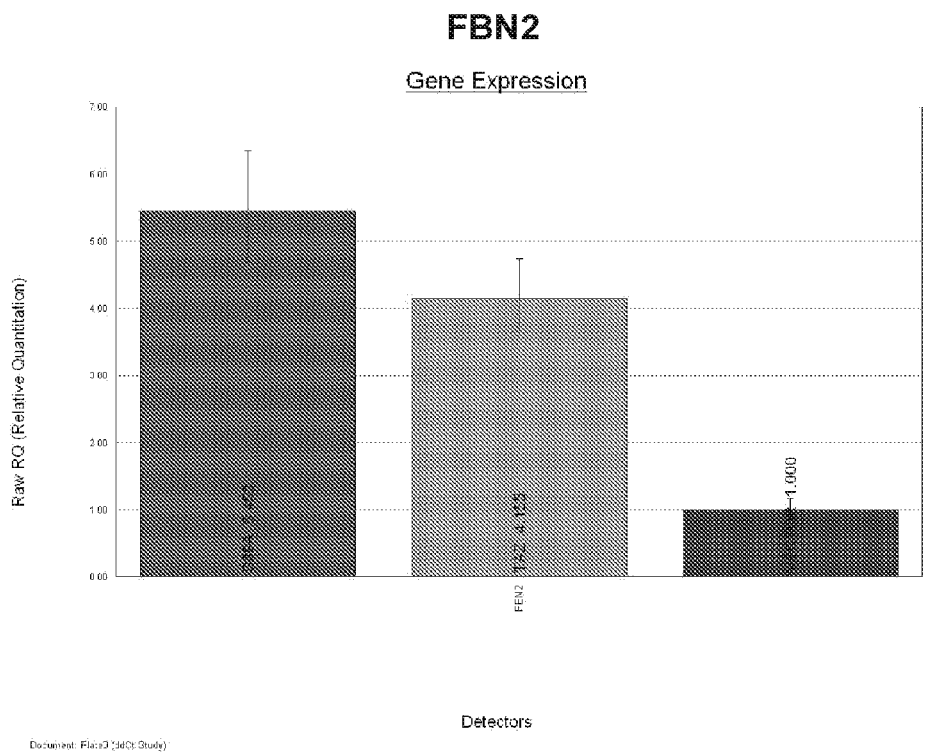
Figure 12:
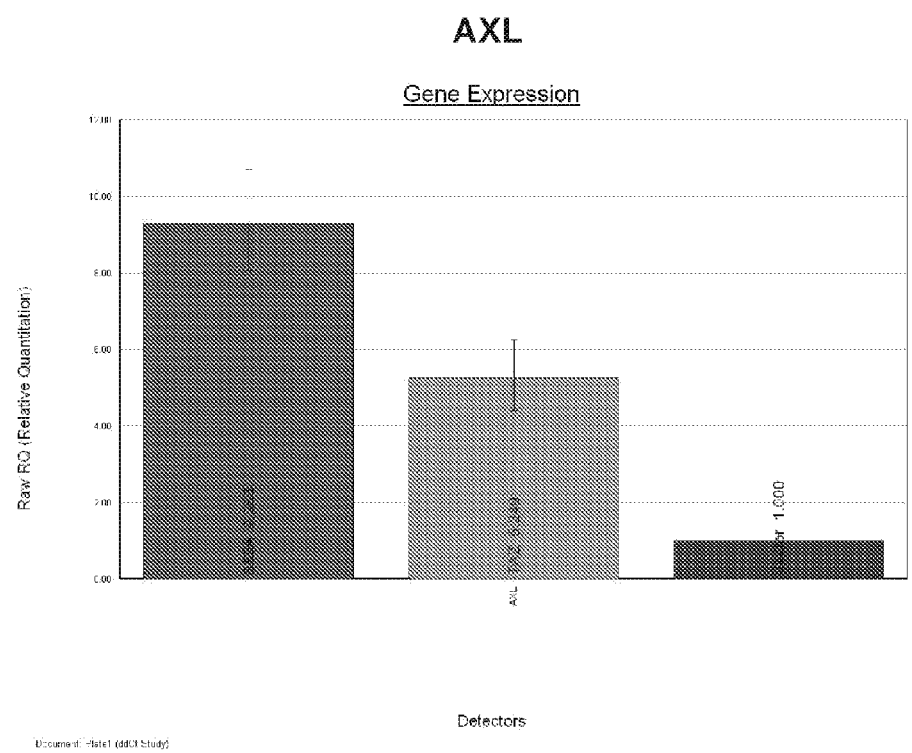
Figure 12:
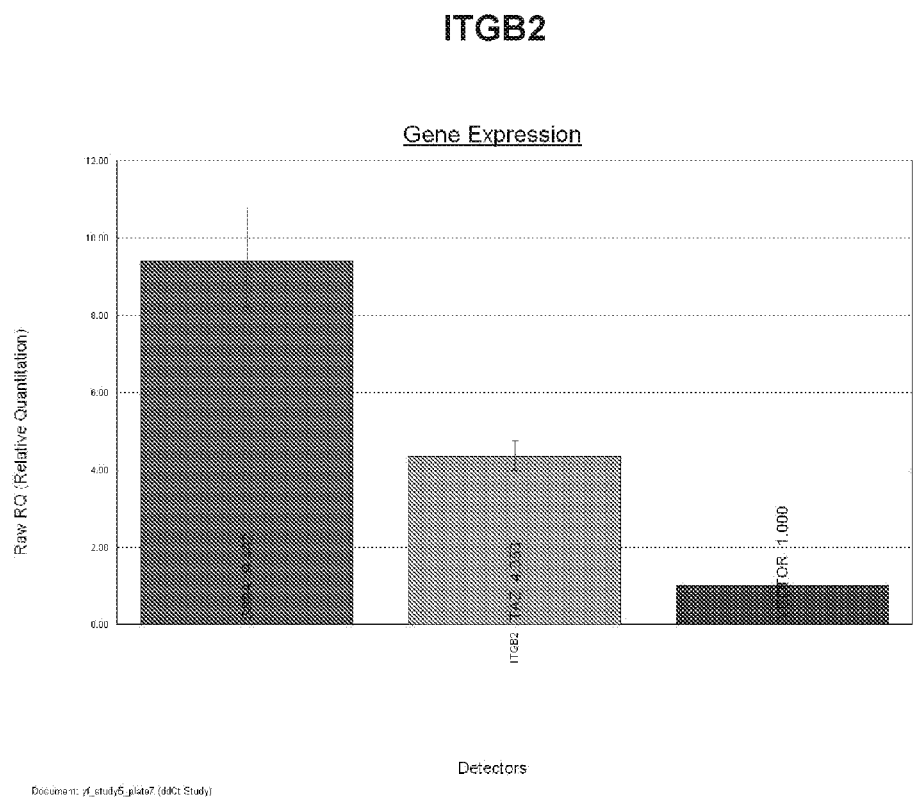
Figure 12:
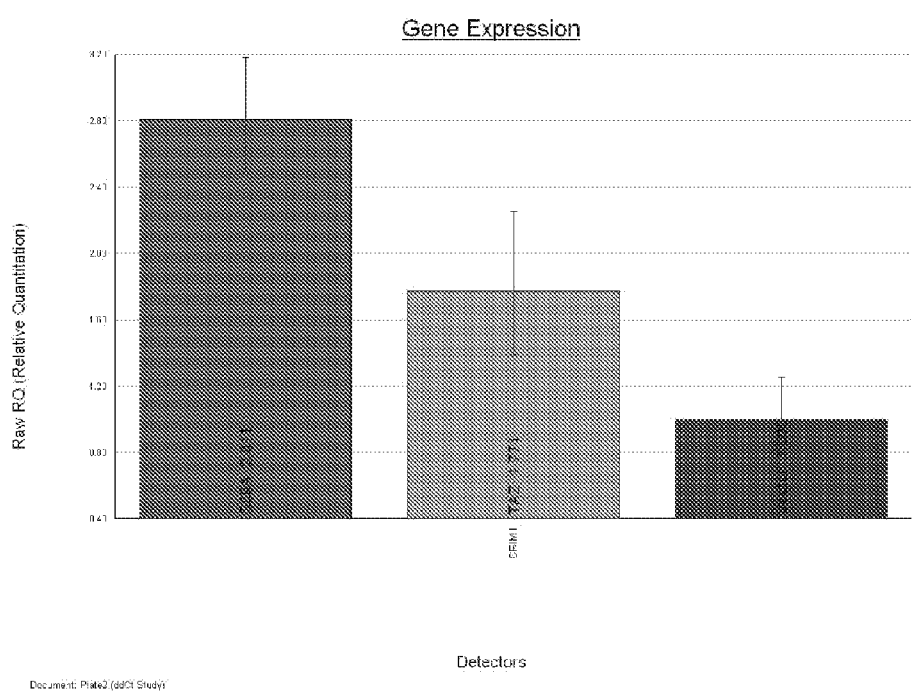
Figure 12:
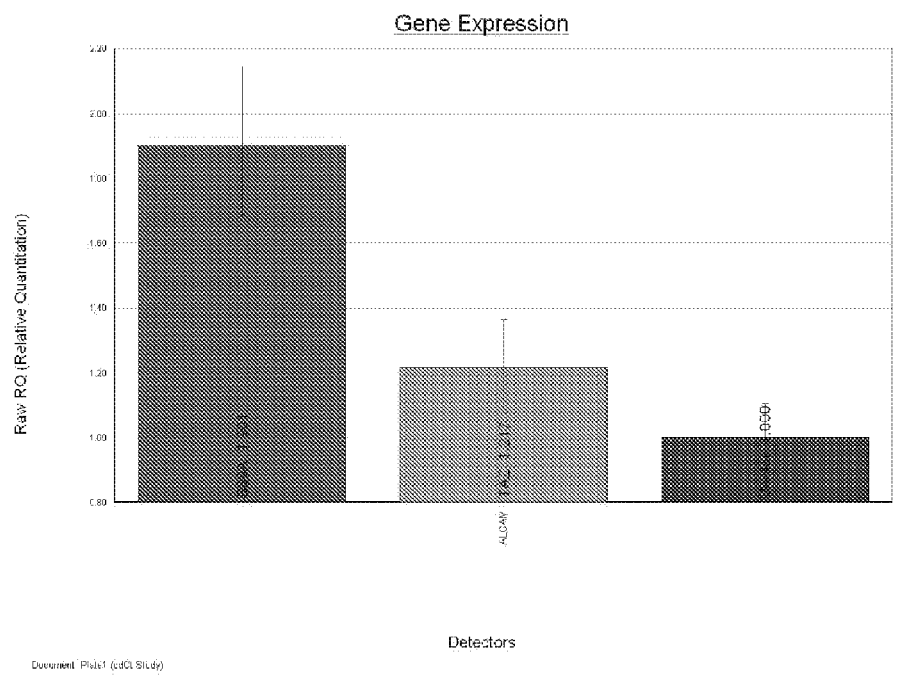

As shown in FIG. 12, TAZ up-regulates the expression of 8 secreted proteins (IGFBP3, ADAMTS1, CTGF, Cyr61, FSTL1, FN1, FBN1 and FBN2) as well as 4 surface membrane proteins (AXL, ITGB2, CRIM1, and Alcam).

These proteins (including combinations of these proteins) will offer new diagnostic biomarkers for breast and other cancers. Furthermore, the surface membrane proteins may offer candidates for antibody therapy.

Example 23

Discussion

In our ongoing proteomics analysis of proteins in human cancer cell lines, we have noticed the higher expression levels of TAZ in more invasive breast cancer cells. This observation prompted us to investigate the physiological/clinical relevance and the role of TAZ in tumorigenesis of breast cancer. TAZ is widely expressed in breast cancer cells. An important observation is that most highly invasive breast cancer cell lines express TAZ at levels that are about 4 times of those expressed by the majority of weakly invasive breast cancer cells, implying a role for TAZ in the invasiveness of breast cancer cells. The clinical relevance of this observation is supported by the finding that TAZ is overexpressed in a significant fraction of breast cancers (about 21.4% of 126 commercially available breast cancer samples examined). As invasiveness of cancer cells is dependent on increased migratory and invasive properties, we have tested the hypothesis that the mechanism of action of TAZ overexpression in breast cancers and cell lines is to promote the migration and invasiveness of breast cancer cells. Both gain of function (by overexpression) and loss of function (by shRNA-mediated knockdown) approaches are used to establish the critical role of TAZ in the migration and invasion of breast cancer cells. Overexpression of TAZ in MCF10A cells to a level about 2-3 fold of those detected in highly invasive cells caused a morphological change from an epithelial to a fibroblast-like appearance and dramatically increased the migratory and invasive properties of the cells. Furthermore, shRNA-mediated knockdown of TAZ expression in MCF7 and Hs578T cells reduced cell migration and invasion. The epithelial clusters of MCF7 cells became more densely-packed with cells when TAZ expression is knocked down. These results indicate that TAZ is a negative regulator of epithelial morphology/architecture as well as a positive regulator for invasive and migratory behavior. It is conceivable that TAZ overexpression in breast cancer may trigger the loss of epithelial property to promote the migratory property, an important event for ductal carcinoma in situ to progress into IDC. Finally, when TAZ expression is knocked down in MCF7 cells, their anchorage-independent growth in soft agar and tumorigenesis in nude mice are retarded, suggesting that TAZ overexpression is an important part of the process involved in breast cancer development and progression. We believe that our experiments have addressed directly the role of TAZ rather than off-target of shRNA. Firstly, we have employed several different shRNAs and observed a correlation between the extent of knockdown and the observed consequence on cellular behaviors. Secondly, results derived from overexpression in MCF10A cells lead to similar conclusions. Finally, re-introduction of RNAi-resistant mouse cDNA encoding Flag-tagged mouse TAZ (mTAZ) in MCF7-KD-652 (TAZ knocked-down) significantly restored the ability of the cells to form colonies in soft-agar and the results are shown as supplementary FIG. S2.

Although the molecular mechanism governing the function of TAZ is not fully clear, one of the mechanisms for TAZ action is to trigger a loss of epithelial morphology, to promote cell migration and invasion, and to support anchorage-independent growth, all of which are important for cancer initiation, progression and invasion. Although TAZ overexpression is not sufficient to enable MCF10A cells to grow in soft agar (unpublished observation), it is important for anchorage-independent growth of MCF7 cells. TAZ may thus play an critical role but not be solely sufficient for anchorage-independent growth of breast cancer cells. The morphological change of MCF10A cells due to TAZ overexpression is similar to the epithelial-mesenchymal transition (EMT) (21) characterized by loss of cell adhesion and increased cell mobility, whereas the altered morphology of MCF7 cells due to TAZ knockdown might be related to the mesenchymal-epithelial transition (MET). TAZ might also be part of the regulatory machinery governing the EMT/MET events in breast epithelial cells and its de-regulated expression will enhance EMT to facilitate the development of breast cancer and invasive property. Preliminary study suggests that the expression level of E-cadherin in MCF10A and MCF7 cells is not significantly altered by either overexpression or knockdown of TAZ, indicating that TAZ may regulate EMT/MET via mechanism different from those utilized by Twist, snail, and slug, which are known to promote EMT by down-regulating E-cadherin (22). Based on our current knowledge of TAZ as a co-activator of gene transcription, one possible mechanism for the action of TAZ is to interact with other transcriptional activators to enhance the transcription of genes that are involved in cell migration. Our preliminary microarray analysis seems to support this possibility as many genes that are potentially involved in cell migration and other cellular processes are up-regulated by TAZ. We are in the process of verifying these results to identify the genuine downstream targets of TAZ that are involved in cell migration. At the same time, TAZ may directly interact with proteins that are involved in cell migration via its PDZ domain, WW domain or coiled-coiled domain. Our preliminary analysis of cells expressing EGFP-tagged TAZ indicates that some EGFP-TAZ can be detected in the membrane ruffles. Further studies will be necessary to explore these possibilities.

YAP, a protein highly homologous to TAZ, is recently identified as a candidate oncogene on the chromosome 11q22 amplicon. Overexpression of human YAP in nontransformed mammary epithelial cells induces EMT, suppresses apoptosis, and promotes growth factor-independent proliferation and anchorage-independent growth in soft-agar (23). Hence, YAP and TAZ may share similar or overlapping functions. However, we did not observe obvious correlation of YAP expression levels with the invasiveness of breast cancer cells, whereas the expression of TAZ is much increased in more invasive breast cancer cell lines (FIG. 1). In conjunction with the observation that the expression of YAP is not affected by shRNA-mediated knockdown of TAZ, it seems that TAZ and YAP are independently-regulated. A few other studies suggest that YAP may have tumor-suppressing property by interacting with and stabilizing tumor suppressor p73 in the nucleus for proper execution of the cell death pathway (24). More future studies are needed to gain full understanding about these issues.

The finding that TAZ is overexpressed in breast cancers and cancer cell lines and its critical role in cell migration, invasion and tumorigenesis is of significance. Firstly, it might serve as a novel biomarker for breast cancers (especially IDCs) and our findings suggest that a comprehensive examination of TAZ expression in a large number of breast cancers in terms of the prevalence, clinical outcome, and response to various treatments is warranted. Secondly, our findings have laid down a novel and solid foundation for future studies aiming to reveal additional insights into the molecular mechanism governing its role in breast cancer cell migration, invasion and tumorigenesis and its interplay with other proteins involved in the development, progression and metastasis of breast cancers. Furthermore, TAZ might offer a novel target to treat breast cancers as its expression is preferentially increased in invasive breast cancer cells and the levels correlate with invasiveness. Because TAZ plays an important role in tumorigenesis of breast cancer cells, yet clearly not essential for mouse development and fertility, it might be an effective yet selective target for breast cancer therapy.

References

1. Hinestrosa M C, Dickersin K, Klein P et al. Shaping the future of biomarker research in breast cancer to ensure clinical relevance. Nat Rev Cancer 2007; 7:309-315.
2. Sjoblom T, Jones S, Wood L D et al. The consensus coding sequences of human breast and colorectal cancers. Science 2006; 314:268-274.
3. Allred D C, Brown P, Medina D. The origins of estrogen receptor alpha-positive and estrogen receptor alpha-negative human breast cancer. Breast Cancer Res 2004; 6:240-245.
4. Zajchowski D A, Bartholdi M F, Gong Y et al. Identification of gene expression profiles that predict the aggressive behavior of breast cancer cells. Cancer Res 2001; 61:5168-5178.
5. Thompson E W, Paik S, Brunner N et al. Association of increased basement membrane invasiveness with absence of estrogen receptor and expression of vimentin in human breast cancer cell lines. J Cell Physiol 1992; 150:534-544.
6. Sommers C L, Byers S W, Thompson E W, Torri J A, Gelmann E P. Differentiation state and invasiveness of human breast cancer cell lines. Breast Cancer Res Treat 1994; 31:325-335.
7. Price J E, Polyzos A, Zhang R D, Daniels L M. Tumorigenicity and metastasis of human breast carcinoma cell lines in nude mice. Cancer Res 1990; 50:717-721.
8. Neve R M, Chin K, Fridlyand J et al. A collection of breast cancer cell lines for the study of functionally distinct cancer subtypes. Cancer Cell 2006; 10:515-527.
9. Debnath J, Muthuswamy S K, Brugge J S. Morphogenesis and oncogenesis of MCF-10A mammary epithelial acini grown in three-dimensional basement membrane cultures. Methods 2003; 30:256-268.
10. Kanai F, Marignani P A, Sarbassova D et al. TAZ: a novel transcriptional co-activator regulated by interactions with 14-3-3 and PDZ domain proteins. EMBO J. 2000; 19:6778-6791.
11. Park K S, Whitsett J A, Di Palma T, Hong J H, Yaffe M B, Zannini M. TAZ interacts with TTF-1 and regulates expression of surfactant protein-C. J Biol Chem 2004; 279:17384-17390.

12. Cui C B, Cooper L F, Yang X, Karsenty G, Aukhil I. Transcriptional coactivation of bone-specific transcription factor Cbfal by TAZ. Mol Cell Biol 2003; 23:1004-1013.
13. Tian Y, Li D, Dahl J, You J, Benjamin T. Identification of TAZ as a binding partner of the polyomavirus T antigens. J Virol 2004; 78:12657-12664.
14. Mahoney W M, Jr., Hong J H, Yaffe M B, Farrance I K. The transcriptional co-activator TAZ interacts differentially with transcriptional enhancer factor-1 (TEF-1) family members. Biochem J 2005; 388:217-225.
15. Murakami M, Nakagawa M, Olson E N, Nakagawa O. A WW domain protein TAZ is a critical coactivator for TBX5, a transcription factor implicated in Holt-Oram syndrome. Proc Natl Acad Sci USA 2005; 102:18034-18039.
16. Murakami M, Tominaga J, Makita R et al. Transcriptional activity of Pax3 is co-activated by TAZ. Biochem Biophys Res Commun 2006; 339:533-539.
17. Hong J H, Hwang E S, McManus M T et al. TAZ, a transcriptional modulator of mesenchymal stem cell differentiation. Science 2005; 309:1074-1078.
18. Hong J H, Yaffe M B. TAZ: a beta-catenin-like molecule that regulates mesenchymal stem cell differentiation. Cell Cycle 2006; 5:176-179.
19. Hossain Z, Ali S M, Ko H L et al. Glomerulocystic kidney disease in mice with a targeted inactivation of Wwtrl. Proc Natl Acad Sci USA 2007; 104:1631-1636.
20. Tian Y, Kolb R, Hong J H et al. TAZ promotes PC2 degradation through a SCFbeta-Trcp E3 ligase complex. Mol Cell Biol 2007; 27:6383-6395.
21. Maeda M, Johnson K R, Wheelock M J. Cadherin switching: essential for behavioral but not morphological changes during an epithelium-to-mesenchyme transition. J Cell Sci 2005; 118:873-887.
22. Peinado H, Olmeda D, Cano A. Snail, Zeb and bHLH factors in tumour progression: an alliance against the epithelial phenotype? Nat Rev Cancer 2007; 7:415-428.
23. Overholtzer M, Zhang J, Smolen G A et al. Transforming properties of YAP, a candidate oncogene on the chromosome 11q22 amplicon. Proc Natl Acad Sci USA 2006; 103:12405-12410.
24. Strano S, Blandino G. YAP1 meets tumor suppression. Mol Cell 2007; 27:863-864.
25. Hong, J.-H.; Hwang, E. S.; McManus, M. T.; Amsterdam, A.; Tian, Y.; Kalmukova, R.; Mueller, E.; Benjamin, T.; Spiegelman, B. M.; Sharp, P. A.; Hopkins, N.; Yaffe, M. B.: TAZ, a transcriptional modulator of mesenchymal stem cell differentiation. Science 309: 1074-1078, 2005. PubMed ID: 16099986
26. Kanai, F.; Marignani, P. A.; Sarbassova, D.; Yagi, R.; Hall, R. A.; Donowitz, M.; Hisaminato, A.; Fujiwara, T.; Ito, Y.; Cantley, L. C.; Yaffe, M. B.: TAZ: a novel transcriptional co-activator regulated by interactions with 14-3-3 and PDZ domain proteins. EMBO J. 19: 6778-6791, 2000. PubMed ID: 11118213
27. Murakami, M.; Nakagawa, M.; Olson, E. N.; Nakagawa, O.: A WW domain protein TAZ is a critical coactivator for TBX5, a transcription factor implicated in Holt-Oram syndrome. Proc. Nat. Acad. Sci. 102: 18034-18039, 2005. PubMed ID: 16332960
28. Polyak K. On the birth of breast cancer. Biochim Biophys Acta. 2001 1552(1):1-13. Review
29. Singapore Cancer Registry Report No. 5 "Cancer Incidence in Singapore, 1993-1997" published in the Yr 2000
30. Neve et al (2006). A collection of breast cancer cell lines for the study of functionally distinct cancer subtypes. Cancer Cell 10, 515-527.
31. Sudol M, Bork P, Einbond A, Kastury K, Druck T, Negrini M, Huebner K, Lehman D. (1995). Characterization of the mammalian YAP (Yes-associated protein) gene and its role in defining a novel protein module, the WW domain. J Biol. Chem. 1995 Jun. 16; 270(24): 14733-41.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A method for treating cancer, comprising:
   detecting upregulation of expression, amount or activity of TAZ/WWTR1 in a cancer cell obtained from a subject as compared to the expression, amount or activity of TAZ/WWTR1 in a control cell known to be non-cancerous, wherein said detecting comprises contacting said cell with an antibody or antigen-binding fragment thereof that specifically binds TAZ/WWTR1; and
   administering an anti-TAZ antibody agent to the subject that inhibits TAZ/WWTR1 expression or activity.

* * * * *